(12) United States Patent
Sabatini et al.

(10) Patent No.: US 11,453,858 B2
(45) Date of Patent: Sep. 27, 2022

(54) HUMAN PLASMA-LIKE MEDIUM

(71) Applicant: Whitehead Institute for Biomedical Research, Cambridge, MA (US)

(72) Inventors: David M. Sabatini, Cambridge, MA (US); Jason Cantor, Madison, WI (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 505 days.

(21) Appl. No.: 16/348,402

(22) PCT Filed: Nov. 13, 2017

(86) PCT No.: PCT/US2017/061377
§ 371 (c)(1),
(2) Date: May 8, 2019

(87) PCT Pub. No.: WO2018/089928
PCT Pub. Date: May 17, 2018

(65) Prior Publication Data
US 2019/0352598 A1    Nov. 21, 2019

Related U.S. Application Data

(60) Provisional application No. 62/421,074, filed on Nov. 11, 2016.

(51) Int. Cl.
*C12N 5/00* (2006.01)
*C12M 1/34* (2006.01)

(52) U.S. Cl.
CPC ........... *C12N 5/0018* (2013.01); *C12M 41/32* (2013.01); *C12N 2500/32* (2013.01); *C12N 2500/34* (2013.01); *C12N 2500/38* (2013.01)

(58) Field of Classification Search
CPC .................................................. C12N 5/0018
See application file for complete search history.

(56) References Cited

U.S. PATENT DOCUMENTS

| | | | |
|---|---|---|---|
| 2007/0004036 A1 | 1/2007 | Faudoa et al. | |
| 2010/0160351 A1 | 6/2010 | Jenkins et al. | |
| 2012/0258439 A1 | 10/2012 | Ali bin M. Abdullah | |
| 2013/0029368 A1 | 1/2013 | Kattman et al. | |
| 2015/0259425 A1 | 9/2015 | Varma et al. | |

FOREIGN PATENT DOCUMENTS

| | | |
|---|---|---|
| JP | S62278980 A | 12/1987 |
| WO | WO-2012/101263 A1 | 8/2012 |
| WO | WO-2018/089928 A1 | 5/2018 |

OTHER PUBLICATIONS

Imamura et al., Oncology Reports, 2015, 33:1837-1843.*
International Search Report and Written Opinion for International Application No. PCT/US2017/061377 dated Mar. 16, 2018.
Peixoto et al., "Acute gout episodes during treatment with capecitabine: a case report," Gastrointest Cancer Res, 7(2):59-60 (2014).
Tseng et al., "Tumor lysis syndrome in a patient with metastatic colon cancer after treatment with oxaliplatin and 5-Fu," J Cancer Res, 46(2):124-127 (2014).
Cantor et al., "Physiologic Medium Rewires Cellular Metabolism and Reveals Uric Acid as an Endogenous Inhibitor of UMP Synthase," Cell, 169:258-272 (2017).
Extended European Search Report for EP Application No. EP 17869135 dated May 13, 2020.
Nishida et al., "Effect of Free Radicals on Lymphocyte Response to Mitogens and Rosette Formation," Clinical Immunology and Immunopathology, 19:319-324 (1981).
Psychogios et al., "The Human Serum Metabolome," PLOS One, 6(2):e16957 (2011).
Sangkop et al., "Uric acid: a modulator of prostate cells and activin sensitivity," Mol Cell Biochem, 414:187-199 (2016).
Voorde et al., "Improving the metabolic fidelity of cancer models with a physiological cell culture medium," Science Advances, 5(1):eaau7314 (2019).

* cited by examiner

*Primary Examiner* — Bin Shen
(74) *Attorney, Agent, or Firm* — Foley Hoag LLP; David P. Halstead

(57) ABSTRACT

In some aspects, described herein are cell culture media that are useful for in vitro culture of mammalian cells. The culture media contain a variety of small organic compounds that are found in normal adult human blood. Also described are methods of using the culture media for a variety of purposes. Also described are methods of treating cancer.

26 Claims, 28 Drawing Sheets
Specification includes a Sequence Listing.

Human plasma-like medium (HPLM) components

| 2-hydroxybutyrate | Citrate | Hypoxanthine |
| 3-hydroxybutyrate | Citrulline | Lactate |
| 4-hydroxyproline | Creatine | Malonate |
| Acetate | Creatinine | Ornithine |
| Acetone | Formate | Pyruvate |
| Acetylglycine | Fructose | Succinate |
| Alpha-aminobutyrate | Galactose | Taurine |
| Betaine | Glutathione | Urea |
| Carnitine | Glycerol | Uric acid |

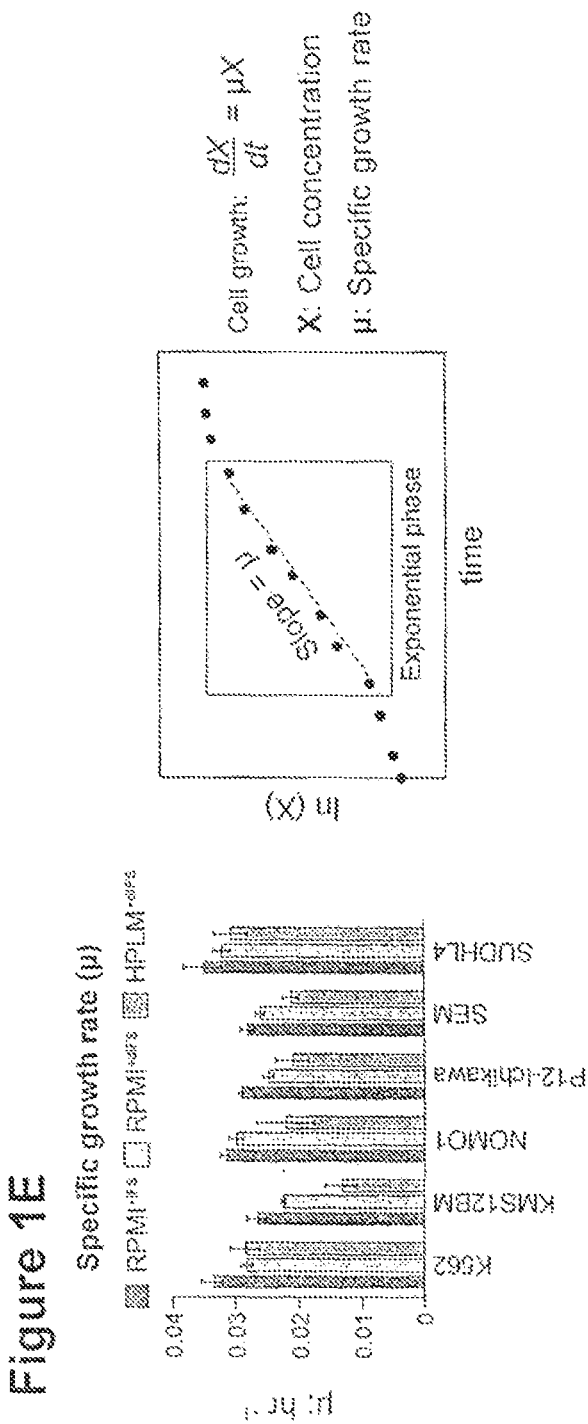

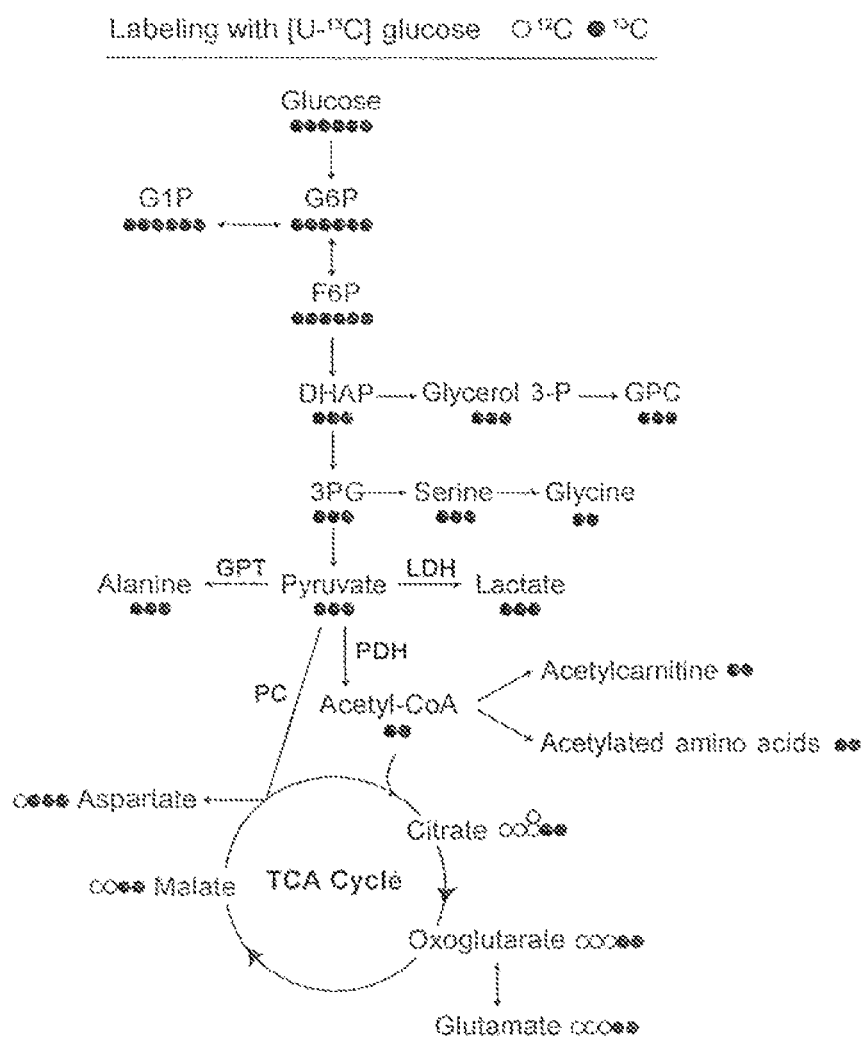

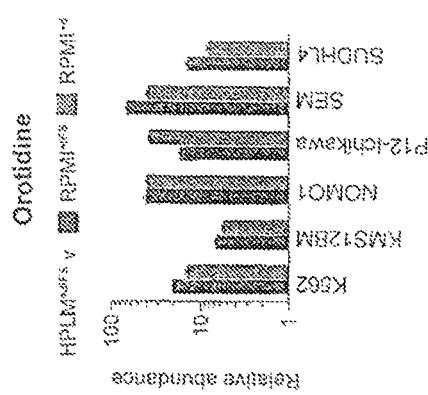
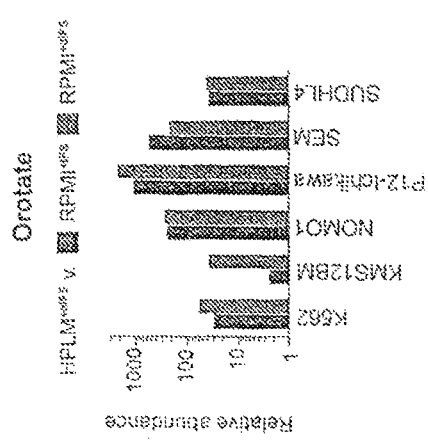
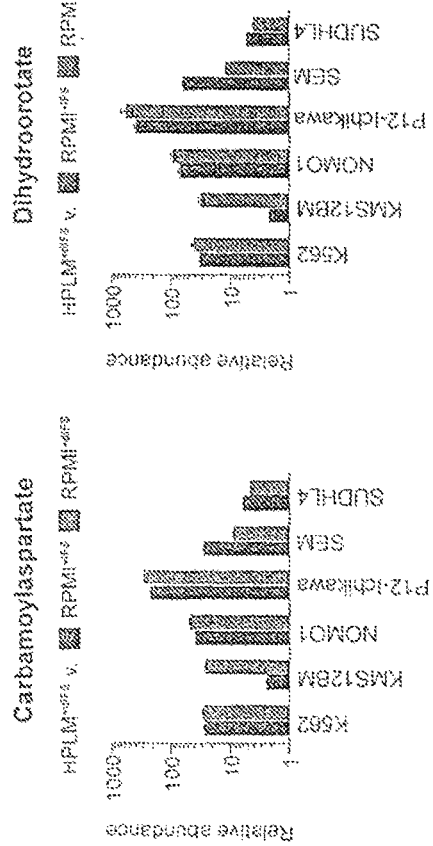

| Culture medium | Uric acid (μM) |
|---|---|
| RPMI$^{+IFS}$ | 7.8 ± 2.4 |
| RPMI$^{+dIFS}$ | < 0.5 |
| HPLM$^{+dIFS}$ | 340 ± 19 |

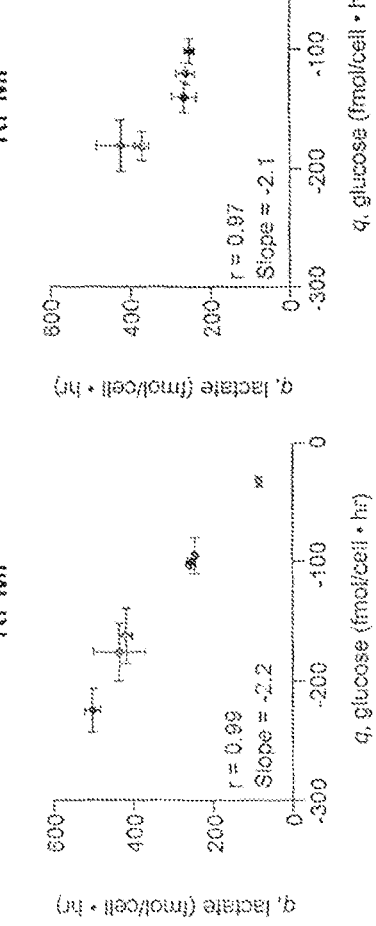

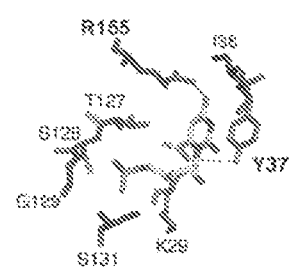 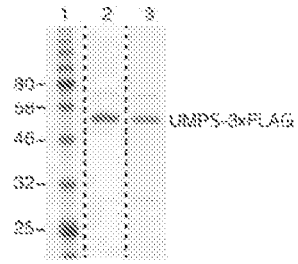
Figure 12A
Figure 12B

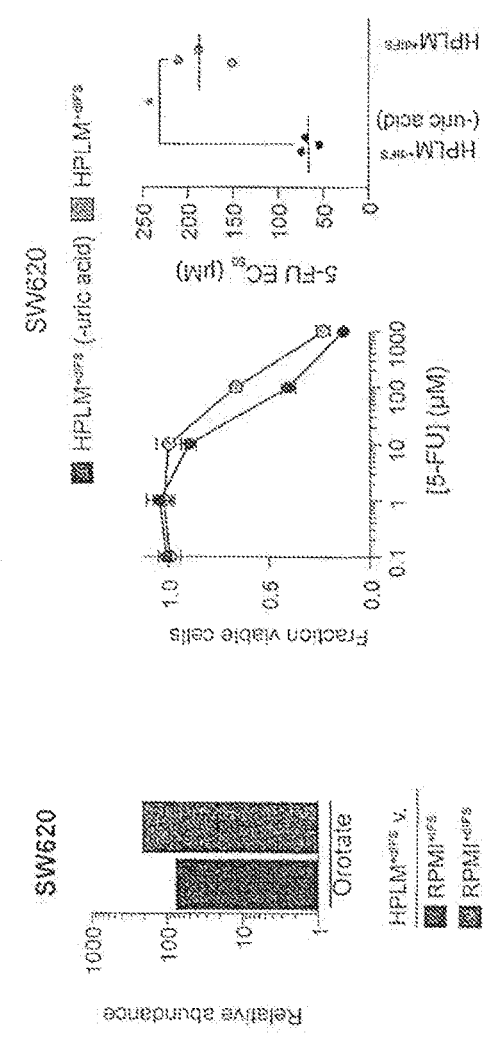
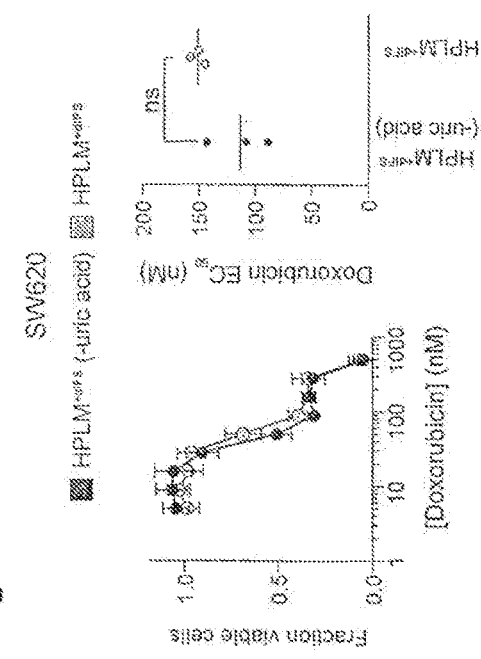
Figure 13A
Figure 13B
Figure 13C

HUMAN PLASMA-LIKE MEDIUM

CROSS-REFERENCE TO RELATED APPLICATIONS

This application is a § 371 national-stage application based on Patent Cooperation Treaty Application serial number PCT/US2017/061377, filed Nov. 13, 2017; which claims the benefit of priority to U.S. Provisional Application Ser. No. 62/421,074, filed on Nov. 11, 2016, which is hereby incorporated by reference herein in its entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: the text file named "WHH-00901 Sequence Listing.txt", which was created on Dec. 27, 2017 and is 4,415 bytes in size.

CROSS-REFERENCE TO RELATED APPLICATION

This application claims the benefit of priority to U.S. Provisional Patent Application Ser. No. 62/421,074, filed Nov. 11, 2016, which is hereby incorporated by reference herein in its entirety.

BACKGROUND

Traditional synthetic cell culture media were developed to address the need for large amounts of medium with less inherent variability than natural media such as biological fluids and tissue extracts (Freshney, 2010). Upon defining the minimum nutritional requirements of two cell types (Eagle, 1955a; 1955b), Eagle formulated one of the first standardized synthetic media, Basal Medium Eagle (BME), over half a century ago (Eagle, 1955c). Soon after, Eagle developed Minimal Essential Medium (MEM) (Eagle, 1959), and within the ensuing decade, Dulbecco and Freeman formulated DMEM (Dulbecco's Modified Eagle Medium) originally for the culture of mouse embryonic cells (Dulbecco and Freeman, 1959), and Moore and colleagues developed RPMI 1640 for that of blood cells (Moore et al., 1967).

SUMMARY

In some aspects, the disclosure provides cell culture media useful for culturing mammalian cells. In some embodiments, described herein are a basal culture medium, comprising: (a) at least 9 proteinogenic amino acids; (b) one or more vitamins; (c) one or more inorganic ions; (d) glucose; and (e) at least 10 small organic compounds selected from 4-hydroxyproline, acetylglycine, alpha-aminobutyrate, betaine, carnitine, citrulline, ornithine, taurine, 2-hydroxybutyrate, 3-hydroxybutyrate, acetate, citrate, formate, lactate, malonate, pyruvate, succinate, acetone, creatine, creatinine, glutathione, glycerol, urea, galactose, fructose, hypoxanthine, and uric acid. In some embodiments, the at least 10 small organic compounds comprise: at least 4 amino acids or amino acid derivatives selected from 4-hydroxyproline, acetylglycine, alpha-aminobutyrate, betaine, carnitine, citrulline, ornithine, and taurine; and at least 6 small organic compounds selected from 2-hydroxybutyrate, 3-hydroxybutyrate, acetate, citrate, formate, lactate, malonate, pyruvate, and succinate. In some embodiments, the at least 10 small organic compounds comprise at least 6 amino acids or amino acid derivatives selected from 4-hydroxyproline, acetylglycine, alpha-aminobutyrate, betaine, carnitine, citrulline, ornithine, and taurine, and, in some embodiments, also comprise at least 4 small organic compounds selected from 2-hydroxybutyrate, 3-hydroxybutyrate, acetate, citrate, formate, lactate, malonate, pyruvate, and succinate. In some embodiments, the at least 10 small organic compounds comprise 4-hydroxyproline, acetylglycine, alpha-aminobutyrate, betaine, carnitine, citrulline, ornithine, and taurine, and, in some embodiments, also comprise at least 6 small organic compounds selected from 2-hydroxybutyrate, 3-hydroxybutyrate, acetate, citrate, formate, lactate, malonate, pyruvate, and succinate. In some embodiments, the at least 10 small organic compounds comprise at least 8 small organic compounds selected from 2-hydroxybutyrate, 3-hydroxybutyrate, acetate, citrate, formate, lactate, malonate, pyruvate, and succinate, and in some embodiments, also comprise at least 4 (or at least 6) amino acids or amino acid derivatives selected from 4-hydroxyproline, acetylglycine, alpha-aminobutyrate, betaine, carnitine, citrulline, ornithine, and taurine. In some embodiments, the at least 10 small organic compounds comprise at least 3, 4, 5, or 6 small organic compounds selected from acetone, creatine, creatinine, glutathione, glycerol, and urea, and, in some embodiments, also comprise any of the aforementioned combinations of components.

In some embodiments, the at least 10 small organic compounds comprise hypoxanthine, uric acid, or both, and, in some embodiments, also comprise any of the aforementioned combinations of components.

In some embodiments, the at least 10 small organic compounds comprise galactose, fructose, or both, and, in some embodiments, also comprise any of the afore-mentioned combinations of components.

In some embodiments, the at least 10 small organic compounds comprise 2-hydroxybutyrate, 3-hydroxybutyrate, 4-hydroxyproline, acetate, acetone, acetylglycine, alpha-aminobutyrate, betaine, carnitine, citrate, citrulline, creatine, creatinine, formate, fructose, galactose, glutathione, glycerol, hypoxanthine, lactate, malonate, ornithine, pyruvate, succinate, taurine, urea, and uric acid.

In some embodiments, the at least 9 proteinogenic amino acids comprise glycine, L-alanine, L-arginine, L-asparagine, L-aspartate, L-cysteine, L-glutamate, L-glutamine, L-histidine, L-isoleucine, L-leucine, L-lysine, L-methionine, L-phenylalanine, L-proline, L-serine, L-threonine, L-tryptophan, L-tyrosine, L-valine, and L-cystine.

In some embodiments, the one or more vitamins comprise at least 8, 9, 10, or 11 of the following vitamins: D-biotin, choline, folic acid, myo-inositol, niacinamide, p-aminobenzoic acid, D-pantothenic acid, vitamin B6, riboflavin, thiamine, and vitamin B12.

In some embodiments, the one or more inorganic ions comprise at least 8, 9, or 10 of the following ions: $Na^+$, $K^+$, $Ca^{2+}$, $Mg^{2+}$, $NH_4^+$, $Cl^-$, $HCO_3^-$, $PO_4^{3-}$, $SO_4^{2-}$, $NO_3^-$. In some embodiments, the concentration of each of said ions that are present in the medium is within about ±50% of the concentration listed for that ion in Table 1. In some embodiments, the concentration of each of said ions that are present in the medium is within about ±25% of the concentration listed for that ion in Table 1. In some embodiments, the concentration of each of said ions that are present in the medium is within about ±10% of the concentration listed for that ion in Table 1. In some embodiments, the concentration of each of said ions that are present in the medium is within about ±0.1% the concentration listed for that ion in Table 1. In some embodiments, each of said ions is present in the medium.

In some embodiments, the one or more inorganic salts comprise at least 6, 7, 8, or 9 inorganic salts selected from: $CaCl_2$), KCl, $MgCl_2$, $MgSO_4$, NaCl, $NaHCO_3$, $Na_2HPO_4$, $Ca(NO_3)_2.4H_2O$, and $NH_4Cl$.

In some embodiments, the concentration of each of the components listed in Table 2 that are present in the medium is within about ±50% of the concentration listed for that component in Table 2. In some embodiments, the concentration of each of the components listed in Table 2 that are present in the medium is within about ±25% of the concentration listed for that component in Table 2. In some embodiments, the concentration of each of the components listed in Table 2 that is present in the medium is within about ±10% of the concentration listed for that component in Table 2. In some embodiments, the concentration of each of the components listed in Table 2 that are present in the medium is within about ±0.1% the concentration listed for that component in Table 2. In some embodiments, each of the components listed in Table 2 is present in the medium.

In some embodiments, the culture media comprises one or more antibiotics, pH indicators, or both.

In some aspects, described herein are culture media comprising any of the combinations of defined components described herein, wherein the culture medium further comprises serum or a serum substitute. In some embodiments, the culture medium comprises from about 1% to about 20% serum. In some embodiments, the culture medium comprises from about 1% to about 5% serum or from about 5% to about 10% serum or from about 10% to about 20% serum. In some embodiments, the culture medium comprises approximately about 10% serum. In some embodiments, the serum is fetal bovine serum. In some embodiments, the serum is dialyzed serum. In some embodiments, the serum is heat inactivated serum.

In some aspects, described herein is a kit comprising one or more containers that collectively contain the components of the culture medium. In some embodiments, the kit comprises at least two containers, each containing a plurality of mutually compatible components of the culture medium. In some embodiments, the kit further comprises instructions for preparing the culture medium, instructions for culturing cells in the culture medium, or both.

In some aspects, described herein is a method of preparing a culture medium as described herein, comprising combining the respective components thereof.

In some aspects, described herein is composition comprising a culture medium described herein and one or more mammalian cells. In some embodiments, the mammalian cells comprise human cells. In some embodiments, the cells comprise blood cells. In some embodiments, the cells comprise cancer cells.

In some aspects, a culture medium or composition described herein further comprises a test agent. In some embodiments, the test agent is a small molecule. In some embodiments, the test agent is a chemotherapeutic agent.

In some aspects, the disclosure provides methods of culturing cells using culture media disclosed herein. For example, described herein is a method of culturing one or more mammalian cells comprising providing a culture medium or composition described herein and culturing one or more mammalian cells in the culture medium. In some embodiments, the one or more mammalian cells comprise human cells. In some embodiments, the one or more mammalian cells comprise blood cells. In some embodiments, the one or more mammalian cells comprise cancer cells. In some embodiments, the method further comprises adding a test agent to the culture medium.

In some aspects, described herein is a method of characterizing a mammalian cell population or cell line comprising: (a) culturing one or more cells of a mammalian cell population or cell line in a culture medium described herein; and (b) detecting a phenotype of the cells cultured in the culture medium or obtaining results of an assay performed with the cells cultured in the culture medium. In some embodiments, the method further comprises (c) culturing one or more cells from the same population or cell line in a second culture medium; (d) detecting a phenotype of the cells cultured in the second culture medium or obtaining results of an assay performed with the cells cultured in the second culture medium; and (e) comparing the phenotype detected in step (b) with the phenotype of one or more cells from the same population or cell line that have been cultured in a second culture medium or comparing results of the assay with results of the same assay performed with one or more cells from the same population or cell line that have been cultured in a second culture medium. In some embodiments, the method comprises detecting a difference between the phenotype or assay results obtained from cells cultured in the first culture medium and the phenotype or assay results obtained from cells cultured in the second culture medium. In some embodiments, the method comprises contacting the cells with a test agent during part or all of the period during which they are cultured in the culture medium. In some embodiments, the method comprises comparing the phenotype of cells cultured in the culture medium in the presence of the test agent with the phenotype of cells from the same population or cell line that have been cultured in the second culture medium in the presence of the test agent or comparing results of the assay performed with cells cultured in the culture medium in the presence of the test agent with results of the same assay performed with cells from the same population or cell line that have been cultured in the second culture medium in the presence of the test agent. In some embodiments, the second culture medium is a standard culture medium. In some embodiments, the assay is a viability assay, proliferation assay, apoptosis assay, autophagy assay, reporter assay, or cytotoxicity assay.

In some aspects, described herein is a method of characterizing a test agent comprising: (a) culturing one or more mammalian cells in a culture medium as described herein in the presence of the test agent; and (b) obtaining results of an assay performed with the cells. In some embodiments, the method further comprises (c) culturing one or more cells from the same population or cell line in a second culture medium in the presence of the test agent and (d) obtaining results of an assay performed with the cells cultured in the second culture medium. In some embodiments, the method further comprises comparing results of the assay with results of the same assay performed with one or more cells from the same population or cell line that have been cultured in a second culture medium in the presence of the test agent. In some embodiments, the method further comprises contacting the cells with the test agent for at least about 24 hours. In some embodiments, the second culture medium is a standard culture medium. In some embodiments, the method comprises detecting a difference between the assay results obtained from cells cultured in the first culture medium in the presence of the test agent and the assay results obtained from cells cultured in the second culture medium in the presence of the test agent. In some embodiments, the one or more cells comprise human cells. In some embodiments, the one or more cells comprise blood cells. In some embodiments, the one or more cells comprise cancer cells. In some embodiments, the assay is a viability assay, proliferation assay, apoptosis assay, autophagy assay, reporter assay, or cytotoxicity assay. In some embodiments, the test agent is a small molecule. In some embodiments, the test agent is a chemotherapeutic agent.

In some aspects, the disclosure provides methods of identifying substances, e.g., metabolites, that may affect the efficacy of therapeutic agents.

In some aspects, the disclosure provides methods of modulating the activity of UMP synthase (LIMPS) in a mammalian cell, the methods comprising contacting the cell with an agent that modulates uric acid levels. In some embodiments, the agent increases uric acid levels, thereby reducing the activity of LIMPS. In some embodiments, the agent lowers uric acid levels, thereby increasing the activity of UPMS. In some embodiments, the uric acid modulating agent is administered to a mammalian subject.

In some aspects, described herein is a method of treating cancer in a subject in need thereof comprising administering to the subject one or both of: (a) 5-fluorouracil (5-FU) or a 5-FU prodrug; and (b) a uric acid lowering agent, so that the subject is exposed to both 5-FU and the uric acid lowering agent, e.g., so that the 5-FU or 5-FU prodrug and the uric acid lowering agent overlap in activity and/or effect. In some embodiments, the uric acid lowering agent is uricase. In some embodiments, the uric acid lowering agent is a uricosuric agent, optionally probenecid, benzbromarone or sulfinpyrazone. In some embodiments, the uric acid lowering agent is amplodipine, atorvastatin, fenofibrate, guaifenesin, or lesinurad. In some embodiments, the 5-FU prodrug is tegafur or capecitabine. In some embodiments, the method comprises administering 5-FU or a 5-FU prodrug to a subject to whom a uric acid lowering agent has been administered.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1E depicts specific growth rates of six hematological cancer cell lines cultured in RPMI$^{+IFS}$ (dark gray), RPMI$^{+dIFS}$ (light gray), or HPLM$^{+dIFS}$ (green) (mean±SD, n=3) (left). Specific growth rates (μ) were calculated using natural log-transformed growth curves (right). Cell lines represent the following hematological cancers: K562 (chronic myeloid leukemia), KMS12BM (multiple myeloma), NOMO1 (acute myeloid leukemia), P12-Ichikawa (T-cell acute lymphoblastic leukemia), SEM (B-cell acute lymphoblastic leukemia), SUDHL4 (B-cell lymphoma).

FIG. 3A is a schematic depicting the incorporation of $^{13}$C from glucose into pathways branching from glycolysis and into pyruvate, and various fates of glucose-derived carbon from pyruvate and Acetyl-CoA, including into the TCA cycle. G1P: glucose 1-phosphate. G6P: glucose 6-phosphate. F6P: fructose 6-phosphate. DHAP: dihydroxyacetone phosphate. GPC: glycerophosphocholine. PDH: pyruvate dehydrogenase. LDH: lactate dehydrogenase. GPT: alanine aminotransferase. FIG. 3D depicts the fraction of F6P/G1P labeled with six $^{13}$C (M6) following culture of cells in RPMI$^{+IFS}$ (dark gray) or HPLM$^{+IFS}$ (green) (mean±SD, n=3; *p<0.0001). FIG. 3E depicts the fraction of alanine labeled with three $^{13}$C (M3) following culture of cells in RPMI$^{+IFS}$ (dark gray) or HPLM$^{+IFS}$ (green) (mean±SD, n=3; *p<0.0001). FIG. 3F depicts the fraction of GPC labeled with three $^{13}$C (M3) following culture of cells in RPMI$^{+IFS}$ (dark gray) or HPLM$^{+IFS}$ (green) (mean±SD, n=3; *p<0.0001).

The following figures show the relative intracellular abundances of carbamoylaspartate (FIG. 4A), dihydroorotate (FIG. 4B), orotate (FIG. 4C), and orotidine (FIG. 4D) following culture of cells in HPLM$^{+dIFS}$ compared to that in RPMI$^{+IFS}$ (blue) or RPMI$^{+dIFS}$ (red) (mean±SD, n=3; p<0.0001 for all bars).

Net consumption rates of glucose (q, glucose) versus net secretion rates of lactate (q, lactate) for cells cultured in RPMI$^{+IFS}$ (FIG. 8A), RPMI$^{+dIFS}$ (FIG. 8B), and HPLM$^{+dIFS}$ (FIG. 8C) (mean±SEM for both axes, n=3). See Methods in the Examples section for the equation used to calculate net exchange rates. Points were plotted in GraphPad Prism and fit using a linear regression equation.

Figure 9A:
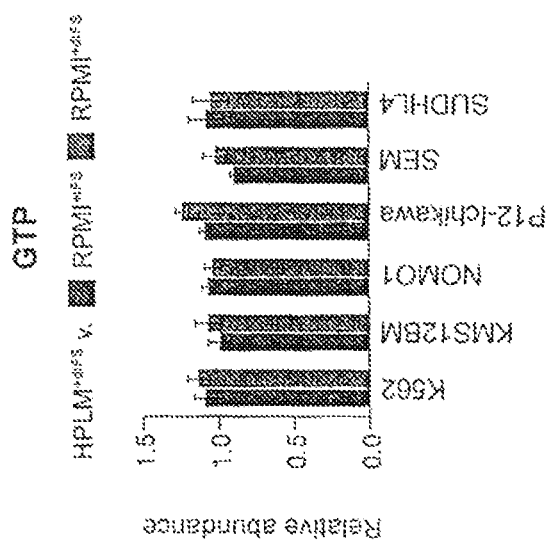
Figure 9B:
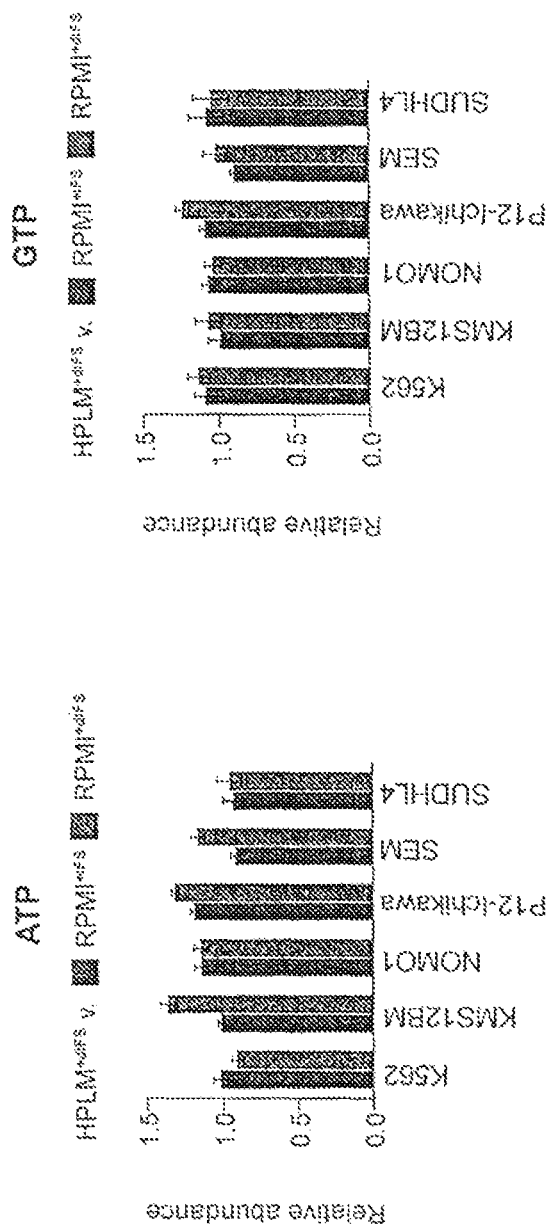

Relative intracellular abundances of ATP (FIG. 9A) and GTP (FIG. 9B) following culture of cells in HPLM$^{+dIFS}$ compared to that in RPMI$^{+IFS}$ (blue) or RPMI$^{+dIFS}$ (red) (mean±SD, n=3).

Figure 10A:
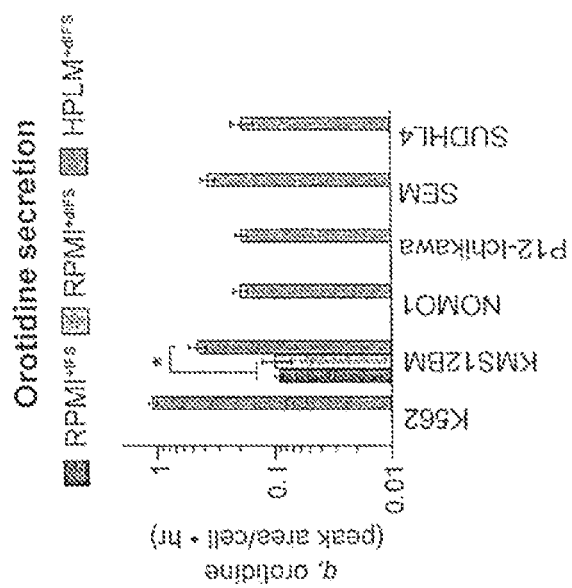
Figure 10B:
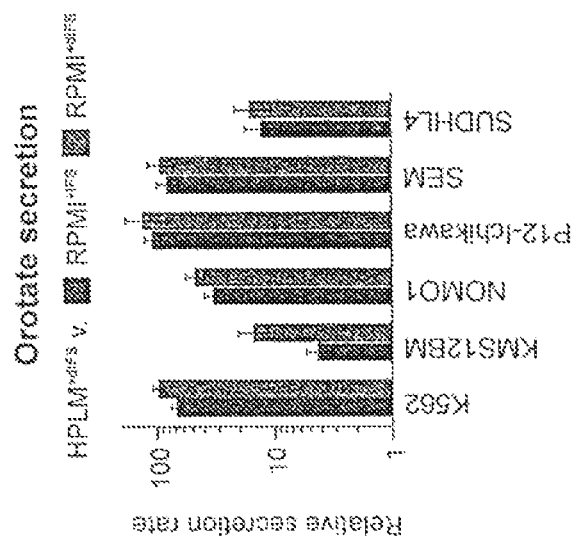

FIG. 10A depicts the relative net secretion rates of orotate during culture of cells in HPLM$^{+dIFS}$ compared to that in RPMI$^{+IFS}$ (blue) or RPMI$^{+dIFS}$ (red) (mean±SEM, n=3; p<0.05 for all bars). See Methods in the Examples section for the equation used to calculate net exchange rates. FIG. 10B depicts the net secretion rates of orotidine (q) during culture of cells in RPMI$^{+IFS}$ (dark gray), RPMI$^{+dIFS}$ (light gray), or HPLM$^{+dIFS}$ (green) (mean±SEM, n=3; *p<0.05). For indicated cell lines other than KMS12BM, net secretion of orotidine was not readily detected in one or more biological replicates during culture of cells in RPMI$^{+IFS}$ or RPMI$^{+dIFS}$. See Methods in the Examples section for the equation used to calculate net exchange rates.

Figure 11A:
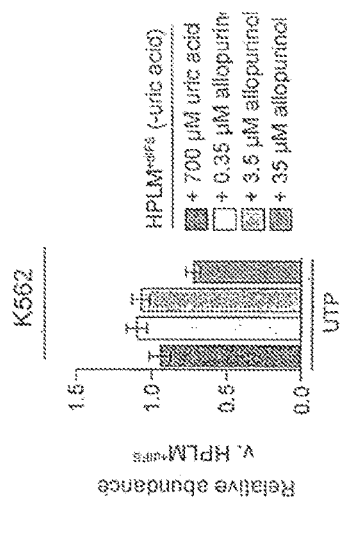
Figure 11B:
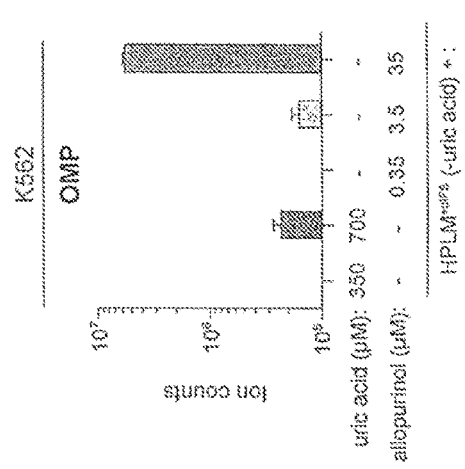
Figure 11C:
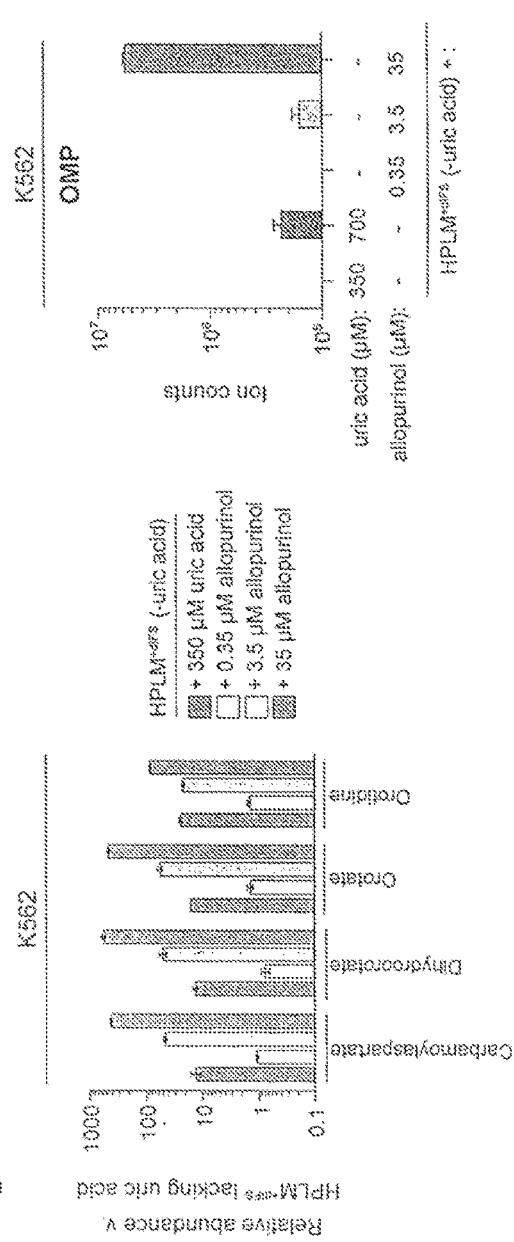
Figure 11D:
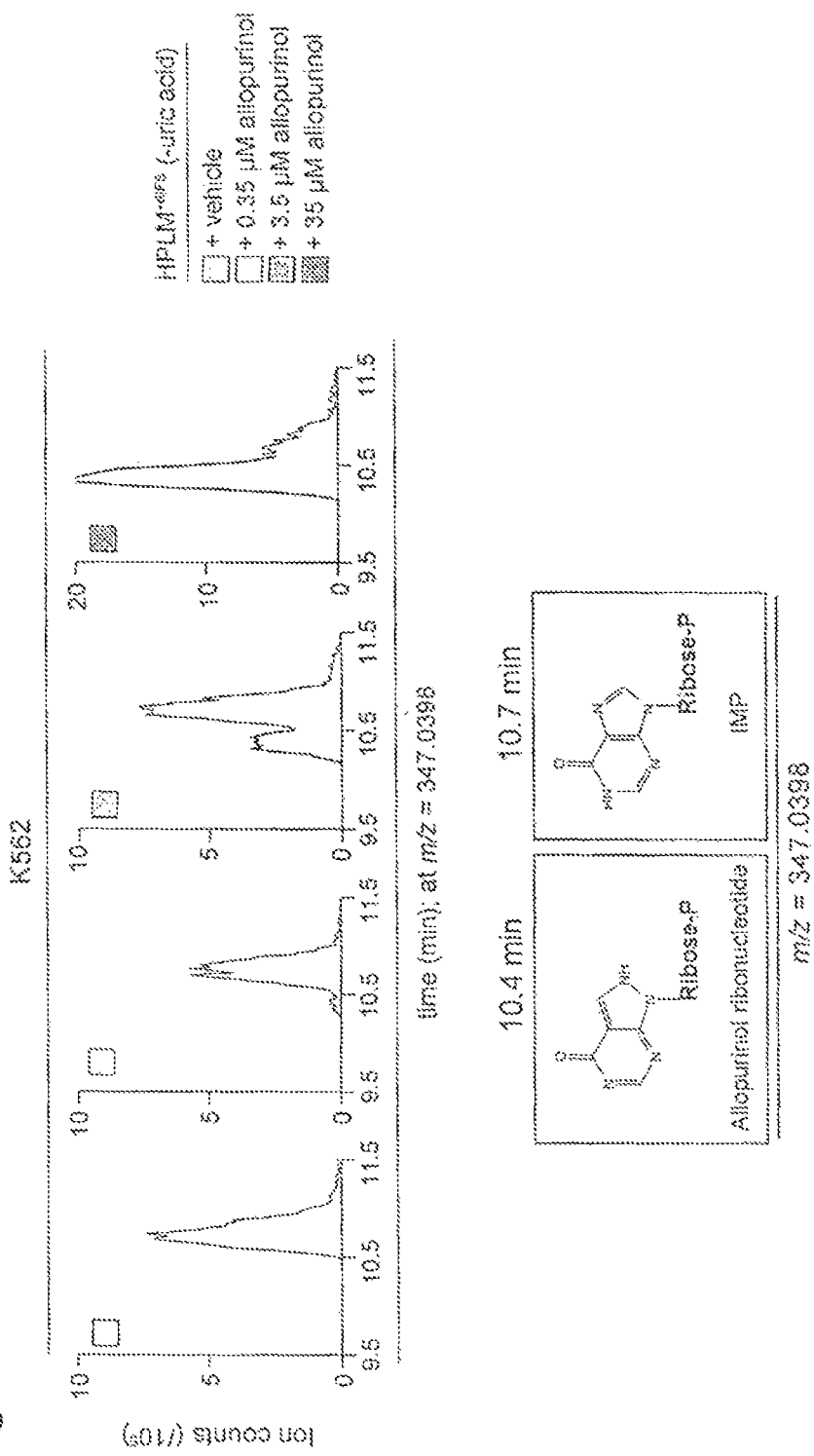

FIG. 11A depicts the relative intracellular abundances of carbamoylaspartate, dihydroorotate, orotate, and orotidine following culture of K562 cells in HPLM$^{+dIFS}$ (green) or in HPLM$^{+dIFS}$ lacking uric acid and containing increasing concentrations of allopurinol (orange) compared to that in HPLM$^{+dIFS}$ lacking uric acid (mean±SD, n=3). FIG. 11B depicts the intracellular abundances of OMP following culture of K562 cells in HPLM$^{+dIFS}$ containing increasing concentrations of uric acid or in HPLM$^{+dIFS}$ lacking uric acid and containing increasing concentrations of allopurinol (mean±SD, n=3). FIG. 11C depicts the relative intracellular abundances of UTP following culture of K562 cells in HPLM$^{+dIFS}$ containing 700 uric acid µM or in HPLM$^{+dIFS}$ lacking uric acid and containing increasing concentrations of allopurinol compared to that in standard HPLM$^{+dIFS}$, which contains 350 µM uric acid (mean±SD, n=3). FIG. 11D depicts the extracted ion chromatograms showing peaks at a mass-to-charge ratio (m/z) of 347.0398 (negative ionization mode) between the indicated retention times from representative K562 samples following culture in HPLM$^{+dIFS}$ lacking uric acid and containing increasing concentrations of allopurinol. Peaks correspond to IMP (black outline) and the putative allopurinol ribonucleotide (red outline) (top). Chemical structures for allopurinol ribonucleotide (red box) and IMP (black box), which share an identical m/z, but differ in retention time (bottom).

FIG. 12A depicts the active site of the OPRT domain of human LIMPS in complex with OMP (yellow) (Protein Data Bank entry 2WNS, chains A and B); the displayed residues comprise the active site as reported elsewhere (Zhang et al., 2013). Residues mutated to alanine in the engineered LIMPS variant (bold type). FIG. 12B depicts 1: M.W. standards; 2: Wild-type UMPS-3×FLAG; 3: LIMPS (Y37A, R155A)-3×FLAG.

FIG. 13A depicts relative intracellular abundances of orotate following culture of SW620 cells in HPLM$^{+dIFS}$ compared to that in RPMI$^{+IFS}$ (blue) or RPMI$^{+dIFS}$ (red) (mean±SD, n=3; p<0.0001 for both bars). Dose-response of SW620 cells to 5-FU (FIG. 13B) or doxorubicin (FIG. 13C) when cultured in HPLM$^{+IFS}$ (green) or HPLM$^{+dIFS}$ lacking uric acid (blue) (mean±SD, n=9). Data points are the average of three independent biological experiments that each consisted of three technical replicates (left). EC$_{50}$ of 5-FU or doxorubicin in SW620 cells when cultured in HPLM$^{+IFS}$ (green) or HPLM$^{+dIFS}$ lacking uric acid (blue). Horizontal bar indicates the mean of three independent biological experiments; * p<0.005; ns: not significant (right plot).

DETAILED DESCRIPTION

I. Culture Media Formulations

In some aspects, the disclosure relates to the recognition that the composition of widely used mammalian cell culture media, while designed to provide the nutrients necessary for survival and proliferation of mammalian cells outside the body, only poorly reflects in vivo nutrient conditions. In some aspects, the disclosure relates to the presence in culture medium of certain metabolites that are found in human blood having a profound effect on mammalian cell phenotype and on the behavior of mammalian cells in assays. For example, the presence of such metabolites in culture media can significantly alter the response of cells to exogenous substances, such as known or potential therapeutic agents.

In some aspects, the disclosure provides cell culture media that support the survival and proliferation of human cells in culture and provide an environment that more closely reflects conditions to which cells would be exposed in vivo than do conventional culture media. Culture media described herein comprise a variety of metabolites that are normally present in human blood. Such metabolites are also present in the liquid portion of blood (plasma) and the liquid portion of blood that remains after blood is allowed to clot (serum). In some embodiments, the concentrations of metabolites may be the same or approximately the same in plasma and serum. In some embodiments, the concentrations of one or more metabolites may differ between plasma and serum. In some embodiments, concentrations of metabolites in blood, plasma, and serum are considered equivalent and used interchangeably. "Metabolite", as used herein, refers to the intermediates and products of metabolism. In some embodiments, the culture media comprises one or more metabolites that are not found in conventional culture media. "Conventional culture media" refers to those culture media that are or have been widely used in cell culture, including at least those cell culture media that are commercially available. Examples of conventional culture media include, e.g., Basal Medium Eagle (BME) (Eagle, 1955c), Minimal Essential Medium (MEM) (Eagle, 1959), Dulbecco's Modified Eagle Medium (DMEM), Iscove's Modified Dulbecco's Medium (IMDM), Roswell Park Memorial Institute (RPMI) 1640, Ham's nutrient mixtures (e.g., F10, F12), Medium 199, McCoy's 5a, and mixtures thereof, e.g., DMEM/F10, DMEM/F12. See, e.g., Freshney, 2010. Such culture media are typically supplemented with animal serum to provide additional supportive substances such as growth factors and hormones. Those of ordinary skill in the art will appreciate that there are a number of variations of such conventional culture media known in the art that are also considered conventional. For example, conventional culture media also include modified versions of any of the afore-mentioned media that permit the culture of mammalian cells with reduced serum supplementation (e.g., reduced by about 50%-90%) as compared with the regular formulation, such as Advanced RPMI and Advanced DMEM (ThermoFisher). Mixtures of conventional culture medium may comprise from about 10% to about 90% of a first medium, with the remainder being composed of a second medium. In some embodiments, a mixture is about a 50:50 mixture.

The cell culture media described herein are aqueous-based, i.e., the media comprise a number of ingredients in water, e.g., deionized, distilled water. In certain embodiments, the media can be reconstituted from dry powder and/or frozen components.

The term "ingredient" refers to any compound, whether of chemical or biological origin, that can be used in cell culture media to maintain or promote the survival or proliferation of cells or is at least not inconsistent with the survival and, typically, proliferation, of cells in the amounts present. The terms "component" and "ingredient" are used interchangeably and are all meant to refer to such compounds. Where the present disclosure describes particular ingredients or groups of ingredients, it should be understood that such ingredients or groups of ingredients may in certain embodiments be present in the medium together with any other ingredient or combination of ingredients described herein, unless otherwise indicated or clearly evident from the context.

By "cell culture" or "culture" is meant the maintenance of cells in an artificial, in vitro environment. It is to be understood, however, that the term "cell culture" is a generic term and may be used to encompass the cultivation not only of individual cells, but also of tissues, organoids, organs, or organ systems, for which the terms "tissue culture", "organoid culture", "organ culture", "organ system culture" or "organotypic culture" may also be used.

In some aspects, described herein is a basal culture medium, comprising: (a) at least 9 proteinogenic amino acids; (b) one or more vitamins; (c) one or more inorganic salts; (d) glucose; and (e) at least 10 small organic compounds selected from 4-hydroxyproline, acetylglycine, alpha-aminobutyrate, betaine, carnitine, citrulline, ornithine, taurine, 2-hydroxybutyrate, 3-hydroxybutyrate, acetate, citrate, formate, lactate, malonate, pyruvate, succinate, acetone, creatine, creatinine, glutathione, glycerol, urea, galactose, fructose, hypoxanthine, and uric acid. In some embodiments, the culture medium comprises at least 5 small organic compounds selected from the afore-mentioned group.

As used herein, the term "basal culture medium" or "basal medium" refers to a cell culture medium that contains proteinogenic amino acids, sugar(s) (typically glucose), water-soluble vitamins, and ions, but lacks growth factors and hormones and is typically supplemented with serum or other sources of such supportive substances to produce a complete culture medium that supports viability and proliferation of a wide variety of mammalian cells. Where the present disclosure refers to a culture medium or media, it should be understood that the culture medium or media may be a basal culture medium unless otherwise indicated or clearly evident from the context.

The culture media comprise amino acids that can serve as protein synthesis precursors ("proteinogenic amino acids"). Unless otherwise indicated, amino acids referred to herein that can exist as L- or D-amino acids are understood to be L-amino acids. In certain embodiments, the proteinogenic amino acids that may be included in the culture media include L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, and L-valine. In some embodiments, all of these amino acids are present in the culture medium. In some embodiments, all of these amino acids plus cystine are present in the culture medium. Alternatively, in some embodiments, only essential amino acids are included in the culture medium. Certain mammalian cells, such as human cells, must have adequate amounts of 9 amino acids to survive. These so called "essential" amino acids cannot be synthesized from other precursors by these cells. However, cysteine can partially meet the need for methionine (they both contain sulfur), and tyrosine can partially substitute for phenylalanine. Such essential amino acids include: histidine, isoleucine, leucine, lysine, methionine (and/or cysteine), phenylalanine (and/or tyrosine), threonine, tryptophan, and valine. In some embodiments, histidine, isoleucine, leucine, lysine, methionine (and/or cysteine), phenylalanine (and/or tyrosine), threonine, tryptophan, and valine and one or more additional proteinogenic amino acids (e.g., 1, 2, 3, 4, 5, 6, 7, 8, 9, 10, or 11) of the non-essential proteinogenic amino acids) are present in the culture medium. In some embodiments, the media comprises cystine in addition to at least the essential amino acids. Cystine is the oxidized dimer form of cysteine and has the formula $(SCH_2CH(NH_2)CO_2H)_2$. It can be readily reduced to cysteine and is considered a proteinogenic amino acid for purposes of the present disclosure.

In certain embodiments, one or more amino acids may be provided at least in part as a peptide (e.g., a dipeptide or tripeptide). For example, in some embodiments, glutamine may be provided at least in part as L-alanyl-L-glutamine (sold as GlutaMAX™-I by Life Technologies). In certain embodiments, a culture media of the present disclosure does not contain a dipeptide or tripeptide as a component.

In certain embodiments, the culture medium comprises one or more vitamins selected from: biotin (e.g., D-biotin), choline, folic acid, myo-inositol, niacinamide, p-aminobenzoic acid, D-pantothenic acid, vitamin B6, riboflavin, thiamine, and vitamin B12. In certain embodiments the culture medium comprises at least 6, 7, 8, 9, 10, or all 11 of said vitamins. In certain embodiments, the culture medium comprises at least choline, folic acid, myo-inositol, niacinamde, vitamin B6, riboflavin, and thiamine. In certain embodiments, the culture medium comprises biotin (e.g., D-biotin), choline, folic acid, myo-inositol, niacinamide, p-aminobenzoic acid, D-pantothenic acid, pyridoxine, pyridoxal riboflavin, thiamine, and vitamin B12.

Vitamin B6 refers to a group of chemically similar compounds which can be interconverted in biological systems. These include pyridoxine (PN), pyridoxine 5'-phosphate (PNP), pyridoxal (PL), pyridoxal 5'-phosphate (PLP), pyridoxamine (PM), and pyridoxamine 5'-phosphate (PMP). In certain embodiments, the vitamin B6 in the culture medium may be any of these compounds or combinations thereof. For example, in certain embodiments, the vitamin B6 is pyridoxine. In certain embodiments, the vitamin B6 is pyridoxal. In certain embodiments, the medium contains both pyridoxine and pyridoxal. Vitamin B12 refers to a class of chemically similar compounds that contain cobalt positioned in the center of a planar tetra-pyrrole ring called a corrin ring. These include cyanocobalamin, hydroxocobalamin, methylcobalamin, and adenosylcobalamin. The vitamin B12 may be provided as any of these compounds or mixtures thereof.

The culture medium may comprise any of a variety of inorganic or organic ions. In some embodiments the culture medium comprises at least 7 (i.e., 7, 8, 9, or all 10) of the following ions: $Na^+$, $K^+$, $Ca^{2+}$, $Mg^{2+}$, $NH_4^+$, $Cl^-$, $HCO_3^-$, $PO_4^{3-}$, $SO_4^{2-}$, $NO_3^-$. The ions may be supplied in the form of salts. Exemplary salts that may be used as ingredients are described herein. In some embodiments, one or more of the ion(s) are supplied at least in part as salts wherein the counterion is an inorganic ion. For example, in some embodiments, all of the $Mg^{2+}$ is supplied as $MgCl_2$ and $MgSO_4$. In some embodiments, one or more of the ion(s) are supplied at least in part as salts wherein the counterion is a small organic molecule. For example, in some embodiments some of the $Na^+$ ions are supplied as inorganic sodium salts (e.g., NaCl) and some of the $Na^+$ ions are supplied as sodium acetate.

In certain embodiments, the components of the culture medium are selected so as to provide concentrations of any one or more of the afore-mentioned ions (i.e., $Na^+$, $K^+$, $Ca^{2+}$, $Mg^{2+}$, $NH_4^+$, $Cl^-$, $HCO_3^-$, $PO_4^{3-}$, $SO_4^{2-}$, $NO_3^-$) that are between 0.3 and 3 times the concentration(s) listed for such ion(s) in Table 1, e.g., from about 0.5 to about 2 times the concentrations listed for such ion(s) in Table 1, e.g., from about 0.67 to about 1.5 times the concentration(s) listed for such ion(s) in Table 1, within about ±30% of the concentration(s) listed for such ion(s) in Table 1, within about ±20% of the concentration(s) listed for such ion(s) in Table 1, within about ±10% of the concentration(s) listed for such ion(s) in Table 1, within ±about 5% of the concentration(s) listed for such ion(s) in Table 1, within about ±2% of the concentration(s) listed for such ion(s) in Table 1, or within about ±1% of the concentration(s) listed for such ion(s) in Table 1. In certain embodiments, the components of the culture medium are selected so as to provide concentrations of any one or more of said ions that are present in the medium that is/are as listed for such ion(s) in Table 1.

In certain embodiments, the components of the culture medium are selected so as to provide concentrations of each of said ions that are present in the medium that are from about 0.3 to about 3 times the concentration(s) listed for such ion(s) in Table 1, e.g., from about 0.5 to about 2 times the concentrations listed for such ion(s) in Table 1, e.g., from about 0.67 to about 1.5 times the concentration(s) listed for such ion(s) in Table 1, within about ±30% of the concentration(s) listed for such ion(s) in Table 1, within about ±20% of the concentration(s) listed for such ion(s) in Table 1, within about ±10% of the concentration(s) listed for such ion(s) in Table 1, within about ±5% of the concentration(s) listed for such ion(s) in Table 1, within about ±2% of the concentration(s) listed for such ion(s) in Table 1, or within about ±1% of the concentration(s) listed for such ion(s) in Table 1. In certain embodiments the components of the culture medium are selected so as to provide concentrations of each of said ions that are present in the medium that is/are as listed for such ion(s) in Table 1.

TABLE 1

Salt ions and ion concentrations (in micromolar)

| Ion | Concentration |
|---|---|
| $Na^+$ | 132271 |
| $K^+$ | 4142 |
| $Ca^{2+}$ | 2390 |
| $Mg^{2+}$ | 830 |
| $NH_4^+$ | 40 |
| $Cl^-$ | 116196 |
| $HCO_3^-$ | 24000 |
| $PO_4^{3-}$ | 966 |
| $SO_4^{2-}$ | 350 |
| $NO_3^-$ | 80 |

Inorganic salt ingredients that may be included in the culture media to provide the inorganic ions include, but are not limited to, calcium salts (e.g., $CaCl_2$, $Ca(NO_3)_2 \cdot 4H_2O$), potassium salts (e.g., $KCl$, $K_2SO_4$), magnesium salts (e.g., $MgCl_2$, $MgSO_4$), sodium salts (e.g., $NaCl$, $NaHCO_3$, $Na_2HPO_4$, $Na_2SO_4$), ammonium salts (e.g., $NH_4Cl$, $NH_4HCO_3$, $(NH_4)_2SO_4$). In some embodiments, the culture medium comprises at least one calcium salt, at least one potassium salt, at least one magnesium salt, at least one sodium salt, and at least one ammonium salt. In some embodiments, the culture medium comprises at least 6, at least 7, at least 8, or 9 salts selected from $CaCl_2$, $KCl$, $MgCl_2$, $MgSO_4$, $NaCl$, $NaHCO_3$, $Na_2HPO_4$, $Ca(NO_3)_2 \cdot 4H_2O$, and $NH_4Cl$.

In some embodiments, the culture medium comprises one or more of the small polar compounds listed in Table 2. Such compounds may be referred to as "polar metabolites" or "small polar metabolites". For example, in some embodiments, the culture medium comprises at least 5, e.g., 10, 11, 12, 13, 14, 15, 16, 17, 18, 19, 20, 21, 22, 23, 24, 25, 26, or 27 of the small polar compounds listed in Table 2. Small polar compounds that may be present in the culture medium include a variety of non-proteinogenic amino acids, amino acid derivatives, water soluble acids, sugars, purine metabolites, and among others.

Non-proteinogenic amino acids that may be present in the culture medium include 4-hydroxyproline, acetylglycine, alpha-aminobutyrate, citrulline, and ornithine. In some embodiments, at least 3, i.e., 3, 4, or 5 of the afore-mentioned non-proteinogenic amino acids are present in the culture medium. The at least 3 non-proteinogenic amino acids may be present in any combination.

Amino acid derivatives that may be present in the culture medium include betaine (trimethylglycine), carnitine, and taurine. In some embodiments, at least 1, i.e., 1, 2 or 3, of the afore-mentioned amino acid derivatives are present in the culture medium. When two or more amino acid derivatives are present, they may be present in any combination.

In some embodiments, the culture medium comprises at least 4, i.e., 4, 5, 6, 7, or 8 non-proteinogenic amino acids or amino acid derivatives selected from 4-hydroxyproline, acetylglycine, alpha-aminobutyrate, betaine, carnitine, citrulline, ornithine, and taurine. The at least 4 non-proteinogenic amino acids or amino acid derivatives may be present in any combination.

In some embodiments, the culture medium comprises at least 6 (i.e., 6, 7, 8, or 9) small polar compounds selected from 2-hydroxybutyrate, 3-hydroxybutyrate, acetate, citrate, formate, lactate, malonate, pyruvate, and succinate. For purposes of the present disclosure, 2-hydroxybutyrate, 3-hydroxybutyrate, acetate, citrate, formate, lactate, malonate, pyruvate, and succinate may be referred to as "Group 1 small polar metabolites". The at least 6 Group 1 small polar metabolites may be present in any combination. In some embodiments, all of said Group 1 small polar metabolites are present. In some embodiments, any one or more of said Group 1 small polar metabolites may be provided as a salt, e.g., as a sodium salt.

In some embodiments, the culture medium comprises one or more, e.g., at least 3 (i.e., 3, 4, 5, or 6) small polar compounds selected from the group consisting of: acetone, creatine, creatinine, glutathione, glycerol, and urea. For purposes of the present disclosure, acetone, creatine, creatinine, glutathione, glycerol, and urea may be referred to as "Group 2 small polar compounds". The at least 3 Group 2 small polar compounds may be present in any combination. In some embodiments, all of said Group 2 small polar compounds are present.

In some embodiments, the culture medium comprises at least 4 (i.e., 4, 5, or 6) of said Group 2 small polar compounds in addition to the at least 7 Group 1 small polar metabolites. In some embodiments, the culture medium comprises at least 4 Group 2 small polar metabolites and/or at least 7 Group 1 small polar metabolites in addition to the at least 3 non-proteinogenic amino acids and/or in addition to the at least 1 amino acid derivative. In some embodiments, for example, the culture medium comprises at least 7 Group 1 small polar metabolites, at least 4 Group 2 small polar metabolites, and at least 4 (i.e., 4, 5, 6, 7, or 8) non-proteinogenic amino acids or amino acid derivatives selected from 4-hydroxyproline, acetylglycine, alpha-aminobutyrate, betaine, carnitine, citrulline, ornithine, and taurine. In some embodiments, the culture medium comprises at least 8 Group 1 small polar metabolites, at least 5 Group 2 small polar metabolites, and at least 4 (i.e., 4, 5, 6, 7, or 8) non-proteinogenic amino acids or amino acid derivatives selected from the group consisting of 4-hydroxyproline, acetylglycine, alpha-aminobutyrate, betaine, carnitine, citrulline, ornithine, and taurine. In some embodiments, the culture medium comprises 8 or 9 Group 1 small polar metabolites, 5 or 6 Group 2 small polar metabolites, and 7 or 8 non-proteinogenic amino acids or amino acid derivatives selected from 4-hydroxyproline, acetylglycine, alpha-aminobutyrate, betaine, carnitine, citrulline, ornithine, and taurine.

In some embodiments, the culture medium comprises at least one purine metabolite. In some embodiments, the purine metabolite(s) are selected from hypoxanthine and uric acid. In some embodiments, the medium comprises both hypoxanthine and uric acid. Such purine metabolite(s) may be present in addition to any of the combinations of proteinogenic amino acids, vitamins, non-proteinogenic amino acid(s), amino acid derivatives, ions, salts, Group 1 small polar metabolites, Group 2 small polar metabolites, sugars, and other ingredients described herein.

In certain embodiments, the culture medium comprises glucose. In certain embodiments, the concentration of glucose in the culture medium is from about 3 mM to about 20 mM, e.g., from about 5 mM to about 10 mM, e.g., about 5 mM.

In certain embodiments, the culture medium comprises glucose and one or more additional sugars such as galactose, fructose, or both. In certain embodiments, the culture medium comprises glucose and galactose. In certain embodiments, the culture medium comprises glucose and fructose. In certain embodiments, the culture medium comprises glucose, galactose, and fructose. In certain embodiments, the concentration of galactose in the culture medium is from about 30 μm to about 120 μm, e.g., from about 50 μm to about 80 μm, e.g., about 60 μm, e.g., between 55 μm and 65 μm, e.g., 60 μm. In certain embodiments, the concentration of fructose in the culture medium is from about 20 μm to about 80 μm, e.g., from about 30 μm to about 60 μm, e.g., from about 35 μm to about 45 μm, e.g., about 40 μm.

The sugar(s) may be present in addition to any of the combinations of proteinogenic amino acids, vitamins, non-proteinogenic amino acid(s), amino acid derivatives, ions, salts, Group 1 small polar metabolites, Group 2 small polar metabolites, purine metabolites, and other ingredients described herein.

In some embodiments, the culture medium comprises at least 20, 21, 22, 23, 24, 25, 26, or 27 small organic compounds selected from 2-hydroxybutyrate, 3-hydroxybutyrate, 4-hydroxyproline, acetate, acetone, acetylglycine, alpha-aminobutyrate, betaine, carnitine, citrate, citrulline, creatine, creatinine, formate, fructose, galactose, glutathione, glycerol, hypoxanthine, lactate, malonate, ornithine, pyruvate, succinate, taurine, urea, and uric acid, in addition to glucose and any of the combinations of proteinogenic amino acids, vitamins, non-proteinogenic amino acid(s), amino acid derivatives, ions, salts, sugar(s), and other ingredients described herein.

In certain embodiments, the culture medium has concentrations of any one or more metabolite(s) that are from about 0.3 to about 3 times the concentration(s) listed for such metabolite(s) in Table 2, e.g., from about 0.5 to about 2 times the concentrations listed for such metabolite(s) in Table 2, e.g., from about 0.67 to about 1.5 times the concentration(s) listed for such metabolite(s) in Table 2, within about ±30% of the concentration(s) listed for such metabolite(s) in Table 2, within about ±20% of the concentration(s) listed for such metabolite(s) in Table 2, within about ±10% of the concentration(s) listed for such metabolite(s) in Table 2, within about ±5% of the concentration(s) listed for such metabolite(s) in Table 2, within about ±2% of the concentration(s) listed for such metabolite(s) in Table 2, or within about ±1% of the concentration(s) listed for such metabolite(s) in Table 2, or about equal to the concentration(s) listed for such metabolite(s) in Table 2. In some embodiments, any such metabolite may be present in a concentration up to about 0.25, about 0.5, about 0.75, about 1, about 1.25, about 1.5, about 2, about 2.5, or about 3 times the concentration of such metabolite in normal adult human plasma.

In certain embodiments, the culture medium has concentrations of each metabolite listed in Table 2 that is present in the medium that are from about 0.3 to about 3 times the concentration(s) listed for such metabolite(s) in Table 2, e.g., from about 0.5 to about 2 times the concentrations listed for such metabolite(s) in Table 2, e.g., from about 0.67 to about 1.5 times the concentration(s) listed for such metabolite(s) in Table 2, within about ±30% of the concentration(s) listed for such metabolite(s) in Table 2, within about ±20% of the concentration(s) listed for such metabolite(s) in Table 2, within about ±10% of the concentration(s) listed for such metabolite(s) in Table 2, within about ±5% of the concentration(s) listed for such metabolite(s) in Table 2, within about ±2% of the concentration(s) listed for such metabolite (s) in Table 2, within about ±1% of the concentration(s) listed for such metabolite(s) in Table 2, or about equal to the concentration(s) listed for such metabolite(s) in Table 2. In some embodiments the culture medium has concentrations of each metabolite listed in Table 2 that is present in the medium that are up to about 0.25, about 0.5, about 0.75, about 1, about 1.25, about 1.5, about 2, about 2.5, or about 3 times the concentration of such component in normal adult human plasma.

In certain embodiments, the osmolality of the culture medium is from about 260 mOsm/kg to about 320 mOsm/kg. In certain embodiments, the osmolality of the medium is at least about 275 mOsm/kg, at least about 280 mOsm/kg, at least about 285 mOsm/kg, at least about 290 mOsm/kg, or at least about 295 mOsm/kg, or up to about 320 mOsm/kg. In certain embodiments, the osmolality is from about 285 mOsm/kg to 305 mOsm/kg. In certain embodiments, the osmolality is from about 290 mOsm/kg to about 300 mOsm/kg, e.g., about 295 mOsm/kg.

In some embodiments the culture medium may comprise one or more pH indicators, such as phenol red. In some embodiments phenol red is present in the medium at from about 0.3 to about 3 times the concentration(s) listed in Table 2, e.g., between from about 0.5 to about 2 times the concentrations listed in Table 2, e.g., from about 0.67 to 1.5 times the concentration listed in Table 2, or within about ±30%, about ±20%, about ±10%, about ±5%, about ±2%, about ±1% of the concentration listed in Table 2, or about equal to the concentration(s) listed in Table 2. In some embodiments, phenol red may be present in a concentration up to about 0.25, about 0.5, about 0.75, about 1, about 1.25, about 1.5, about 2, about 2.5, or about 3 times the concentration of listed in Table 2. In some embodiments, the medium does not comprise phenol red.

In some embodiments, the culture medium may comprise one or more buffering agents, to help maintain a desired pH during culture. Frequent, constant or continuous change of culture medium may also help to restore medium pH in fast growing cells. In certain embodiments, the buffering agent is a bicarbonate salt or 2-[4-(2-hydroxyethyl)piperazin-1-yl] ethanesulfonic acid (HEPES).

In certain embodiments, some or all of the above ingredients, when mixed together in solution, form a basal medium. For example, in some embodiments, the culture medium comprises the components disclosed in Table 2 at the concentrations listed in Table 2. Table 2 also lists commercial suppliers of the various components. It should be understood that the components can be obtained from any source.

TABLE 2

Exemplary basal medium components and concentrations (in micromolar)

| Component | Concentration (micromolar) | Exemplary Vender | Product # |
|---|---|---|---|
| Glucose | 5000 | Thermo Fisher Scientific | 15023-21 |
| Proteinogenic Amino acids | | | |
| Alanine | 430 | Sigma | A7627 |
| Arginine | 110 | Sigma | A5131 |
| Asparagine | 50 | Sigma | A0884 |
| Aspartate | 20 | Sigma | A9256 |
| Cysteine | 40 | Sigma | C1276 |
| Cystine | 100 | Sigma | C8755 |
| Glutamate | 80 | Sigma | G1251 |
| Glutamine | 550 | Sigma | G3126 |
| Glycine | 300 | Sigma | G7126 |
| Histidine | 110 | Sigma | H5659 |
| Isoleucine | 70 | Sigma | I2752 |
| Leucine | 160 | Sigma | L8000 |
| Lysine | 200 | Sigma | L5626 |
| Methionine | 30 | Sigma | M9625 |
| Phenylalanine | 80 | Sigma | P2126 |
| Proline | 200 | Sigma | P0380 |
| Serine | 150 | Sigma | S4500 |
| Threonine | 140 | Sigma | T8625 |
| Tryptophan | 60 | Sigma | T0254 |
| Tyrosine | 80 | Sigma | T3754 |
| Valine | 220 | Sigma | V0500 |
| Vitamins | | | |
| Biotin | 0.82 | | |
| Choline | 21.49 | | |
| Folate | 2.27 | | |
| myo-Inositol | 194.27 | | |
| Niacinamide | 8.19 | Sigma R7256 | |
| p-Aminobenzoate | 7.29 | | |
| Pantothenate | 1.05 | | |
| Pyridoxine | 4.86 | | |
| Riboflavin | 0.53 | | |
| Thiamine | 2.96 | | |
| Vitamin B-12 | 0.0037 | | |
| Salts | | | |
| $CaCl_2$ | 2350 | Sigma | C5670 |
| KCl | 4100 | Sigma | P5405 |
| $MgCl_2$ | 480 | Sigma | M8266 |
| $MgSO_4$ | 350 | Sigma | M2643 |
| NaCl | 105000 | Sigma | S7653 |
| $NaHCO_3$ | 24000 | Sigma | S5761 |
| $Na_2HPO_4$ | 870 | Sigma | S9390 |
| $Ca(NO_3)_2 \cdot 4H_2O$ | 40 | Sigma | C1396 |
| $NH_4Cl$ | 40 | Sigma | A9434 |
| Additional polar metabolites | | | |
| 2-hydroxybutyrate | 50 | Sigma | 220116 |
| 3-hydroxybutyrate | 50 | Sigma | 298360 |
| 4-hydroxyproline | 20 | Sigma | H5534 |
| Acetate | 40 | Sigma | S5636 |
| Acetone | 60 | EMD Millipore | AX0120 |
| Acetylglycine | 90 | Sigma | A16300 |
| Alpha-aminobutyrate | 20 | Sigma | A2536 |
| Betaine | 70 | Sigma | 61962 |
| Carnitine | 40 | Sigma | C0283 |
| Citrate | 130 | Sigma | 251275 |
| Citrulline | 40 | Sigma | C7629 |
| Creatine | 40 | Sigma | C0780 |

TABLE 2-continued

Exemplary basal medium components and concentrations (in micromolar)

| Component | Concentration (micromolar) | Exemplary Vender | Product # |
|---|---|---|---|
| Creatinine | 75 | Sigma | C4255 |
| Formate | 50 | Sigma | 94318 |
| Fructose | 40 | Sigma | F3510 |
| Galactose | 60 | Sigma | G5388 |
| Glutathione | 25 | Sigma | G6013 |
| Glycerol | 120 | Sigma | G2025 |
| Hypoxanthine | 10 | Sigma | H9377 |
| Lactate | 1600 | Sigma | L7022 |
| Malonate | 10 | Sigma | M1296 |
| Ornithine | 70 | Sigma | O2375 |
| Pyruvate | 50 | Sigma | P2256 |
| Succinate | 20 | Sigma | S3674 |
| Taurine | 90 | Sigma | T0625 |
| Urea | 5000 | Sigma | U5378 |
| Uric acid | 350 | Sigma | U2625 |
| Other components | | | |
| Phenol red | 14 | Sigma | P5530 |

In some aspects, a cell culture medium described herein is a chemically defined basal medium. "Chemically defined" means that the structures, chemical formulae, and the percentage of the various individual components within a chemical composition are known or can be defined. Serum and tissue extracts are not chemically defined, at least partly because not all individual components are known. For those known components, the amount and the relative percentages of the various components may (and usually do) vary from one batch to another.

In certain embodiments, a basal medium of the present disclosure supports proliferation of a wide range of mammalian cells when supplemented by serum, which serves as a source of supportive substances such as growth factors, hormones, and lipids. In some embodiments, bovine serum, e.g., fetal bovine serum or calf serum, may be used. Other serum sources include horse and human. In some embodiments, a basal medium is supplemented with from about 5% to about 20% serum, e.g., from about 7.5% to about 15% serum, e.g., about 10% serum (e.g., fetal bovine serum). In some embodiments, the serum is heat inactivated. For example, the serum may be heated at about 56° C. for about 30 minutes (or about 25 minutes for equine or human serum). In some embodiments, the serum is not heat inactivated.

In some embodiments, other sources of supportive substances may be used instead of or in addition to serum. For example, a serum replacement such as KnockOut™ Serum Replacement (ThermoFisher) or BIT 9500 (Stemcell Technologies), a platelet lysate, an animal extract such as bovine pituitary extract (BPE), or combinations thereof may be used. In some embodiments the source of supportive substances may be at least partly undefined, as is the case for serum and animal extracts. In some embodiments, the supportive substances may be defined in terms of their structure and amount. For example, individual lipids or chemically synthesized or purified recombinant proteins (e.g., produced by genetically engineered bacteria or fungi) added in known amounts are considered defined ingredients. Examples of supportive substances that may be added to the basal media as individual defined components, as mixtures of individual defined components, or as components of serum or other at least partly undefined substances include insulin or insulin-like growth factor, epidermal growth factor, transferrin, albumin, fatty acids (e.g., lipoic, linoleic, and/or linolenic acid), phospholipids, and cholesterol. In some embodiments, the basal medium may support proliferation of certain mammalian cells without the addition of supportive substances.

In some embodiments, serum, animal extracts, growth factors, hormones, and/or other substances that can contribute to supporting cell viability and proliferation may be added to a basal medium of the present disclosure. These components may be individually added to basal medium, or two or more such components may be mixed, e.g., to form a stock solution, which may then be added to the basal medium.

In some embodiments, serum or other source(s) of supportive substances may be dialyzed or otherwise processed to remove small polar metabolites. In some embodiments, a dialysis membrane having a molecular weight cut-off of about 2,500-about 5,000 daltons, e.g., about 3500 daltons may be used. Dialysis may be performed for sufficiently long such that at least some small polar metabolites, including at least some of the polar metabolites listed in Table 2, are largely removed. For example, in some embodiments, the level of any one or more polar metabolites may be reduced by at least about 50%, at least about 75%, or more. In some embodiments, the amount of any particular metabolite is reduced by from about 50% to about 99%. Larger substances such as most serum proteins (e.g., albumin, transferrin, insulin, growth factors) and substances bound to such proteins, such as lipids, are largely retained. In some embodiments, a saline solution, e.g., a buffered saline solution, e.g., phosphate buffered saline (PBS), may be used as dialysis buffer. In some embodiments, the dialysis buffer has an osmolality from about 250 mOsm/kg to about 350 mOsm/kg, e.g., from about 280 mOsm/kg to about 320 mOsm/kg.

Many cell culture media typically contain one or more antibiotics, which are not necessary for cell growth/proliferation per se, but are present to inhibit the growth of undesirable microbes, such as bacteria and/or fungi. One of ordinary skill in the art appreciates that antibiotics may be added to culture media at or shortly before the time the culture medium is to be used for culturing cells. Antibiotics include natural and synthetic chemical substances of relatively low molecular weight produced by various species of microorganisms, such as bacteria (including *Bacillus* species), actinomycetes (including *Streptomyces*) and fungi, that inhibit growth of or destroy other microorganisms. Substances similar in structure and/or mode of action to natural antibiotics may be synthesized chemically, or natural compounds may be modified to produce semi-synthetic antibiotics. The major classes of antibiotics are: (1) the β-lactams, including the penicillins, cephalosporins and monobactams; (2) the aminoglycosides, e.g., streptomycin, gentamicin, tobramycin, neomycin, netilmycin, and amikacin; (3) the tetracyclines; (4) the sulfonamides and trimethoprim; (5) the fluoroquinolones, e.g., ciprofloxacin, norfloxacin, and ofloxacin; (6) vancomycin; (7) the macrolides, which include for example, erythromycin, azithromycin, tylosin, and clarithromycin; and (8) other antibiotics, e.g., the polymyxins, chloramphenicol and the lincosamides. The culture media may be supplemented by one or more antibiotics that inhibit the growth/proliferation of bacteria, fungi, and/or viruses. Accordingly, in certain embodiments, the culture medium comprises one or more antibiotics. In certain embodiments, the one or more antibiotics include a penicillin antibiotic. In certain embodiments, the one or more antibiotics include an aminoglycoside antibiotic. In certain embodiments, the one or more antibiotics include benzylpenicillin. In certain embodiments, the one or more antibiotics include streptomycin. In certain embodiments, the culture medium comprises benzylpenicillin and streptomycin. In certain embodiments, however, the culture medium may be substantially free of antibiotics. In some embodiments, the culture medium may be substantially free of substances that are not present in adult human blood in detectable amounts, other than pH indicator(s), antibiotic(s), or both.

In some aspects, the present disclosure provides modified versions of conventional culture media. A modified version of a conventional medium contains the same components in the same amounts as the conventional medium and further comprises one or more Group 1 small polar metabolites and/or one or more Group 2 small polar metabolites in an amount from about 0.3 to about 3 times its concentration in adult human plasma. In some embodiments, the conventional culture medium is RPMI, DMEM, BME, MEM, IMDM, Ham's nutrient mixtures (e.g., F10, F12), Medium 199, McCoy's 5a, or a mixture of two or more such media. Exemplary formulations of several conventional culture media are provided in Table 4. All concentrations in Table 4 are in micromolar unless otherwise indicated. In some embodiments, the one or more small polar metabolites is present at from about 0.5 to about 2 times the concentration(s) listed for such metabolite(s) in Table 2, e.g., from about 0.67 to about 1.5 times the concentration(s) listed for such metabolite(s) in Table 2, within about ±30% of the concentration(s) listed for such metabolite(s) in Table 2, within about ±20% of the concentration(s) listed for such metabolite(s) in Table 2, within about ±10% of the concentration(s) listed for such metabolite(s) in Table 2, within about ±5% of the concentration(s) listed for such metabolite(s) in Table 2, within about ±2% of the concentration(s) listed for such metabolite(s) in Table 2, or within about ±1% of the concentration(s) listed for such metabolite(s) in Table 2, or about equal to the concentration(s) listed for such metabolite(s) in Table 2.

TABLE 4

Exemplary conventional media formulae

| | BME | MEM | DMEM | RPMI 1640 |
|---|---|---|---|---|
| | Thermo Fisher Scientific catalog number | | | |
| | 21010 | 11095 | 11965 | 11875 |
| | Concentration | Concentration | Concentration | Concentration |
| Metabolite name | | | | |
| Glucose | 5555 | 5555 | 25000 | 11111 |
| Alanine | 0 | 0 | 0 | 0 |
| Arginine | 99.5 | 597 | 398 | 1149 |

TABLE 4-continued

Exemplary conventional media formulae

| | BME | MEM | DMEM | RPMI 1640 |
|---|---|---|---|---|
| | \multicolumn{4}{c}{Thermo Fisher Scientific catalog number} | | | |
| | 21010 | 11095 | 11965 | 11875 |
| | Concentration | Concentration | Concentration | Concentration |
| Asparagine | 0 | 0 | 0 | 378 |
| Aspartate | 0 | 0 | 0 | 150 |
| Cysteine | 0 | 0 | 0 | 0 |
| Cystine | 51.1 | 99 | 201 | 208 |
| Glutamate | 0 | 0 | 0 | 136 |
| Glutamine | 2000* | 2000 | 4000 | 2055 |
| Glycine | 0 | 0 | 400 | 133 |
| Histidine | 51.6 | 200 | 200 | 97 |
| Hydroxyproline | 0 | 0 | 0 | 153 |
| Isoleucine | 198.5 | 396 | 801 | 382 |
| Leucine | 198.5 | 396 | 801 | 382 |
| Lysine | 199 | 398 | 797 | 219 |
| Methionine | 50.3 | 101 | 201 | 101 |
| Phenylalanine | 100 | 194 | 400 | 91 |
| Proline | 0 | 0 | 0 | 174 |
| Serine | 0 | 0 | 400 | 286 |
| Threonine | 202 | 403 | 798 | 168 |
| Tryptophan | 19.6 | 49 | 78 | 25 |
| Tyrosine | 99.6 | 199 | 398 | 111 |
| Valine | 201 | 393 | 803 | 171 |
| Biotin | 4.1 | 0 | 0 | 0.819 |
| Choline | 7.1 | 7.1 | 28.6 | 21.4 |
| Folate | 2.3 | 2.2 | 9.1 | 2.3 |
| myo-Inositol | 11.1 | 11.1 | 40 | 194.4 |
| Niacinamide | 8.2 | 8.2 | 32.8 | 8.2 |
| p-Aminobenzoate | 0 | 0 | 0 | 7.2 |
| Pantothenate | 2.1 | 2.1 | 8.4 | 0.524 |
| Pyridoxal | 4.9 | 4.9 | 0 | 0 |
| Pyridoxine | 0 | 0 | 19.4 | 4.9 |
| Riboflavin | 0.266 | 0.266 | 1.1 | 0.532 |
| Thiamine | 3 | 3 | 11.9 | 2.9 |
| Vitamin B-12 | 0 | 0 | 0 | 0.00369 |
| $CaCl_2$ | 1802 | 1802 | 1802 | 0 |
| $Ca(NO_3)_2 \cdot 4H_2O$ | 0 | 0 | 0 | 424 |
| $Fe(NO_3)_3 \cdot 9H_2O$ | 0 | 0 | 0.248 | 0 |
| $MgSO_4$ | 814 | 814 | 814 | 407 |
| KCl | 5333 | 5333 | 5333 | 5333 |
| $NaHCO_3$ | 26190 | 26190 | 44048 | 23809 |
| NaCl | 117240 | 117240 | 110344 | 103448 |
| $Na_2HPO_4$ | 0 | 0 | 0 | 5634 |
| $NaH_2PO_4 \cdot H2O$ | 1014 | 1014 | 906 | 0 |
| Small ion | | | | |
| $Na^+$ | 144444 | 144444 | 155298 | 138525 |
| $K^+$ | 5333 | 5333 | 5333 | 5333 |
| $Ca^{2+}$ | 1802 | 1802 | 1802 | 424 |
| $Mg^{2+}$ | 814 | 814 | 814 | 407 |
| $NH_4^+$ | 0 | 0 | 0 | 0 |
| $Fe^{3+}$ | 0 | 0 | 0.248 | 0 |
| $Cl^-$ | 126177 | 126177 | 119281 | 108781 |
| $HCO_3^-$ | 26190 | 26190 | 44048 | 23809 |
| $PO_4^{3-}$ | 1014 | 1014 | 906 | 5634 |
| $SO_4^{2-}$ | 814 | 814 | 814 | 407 |
| $NO_3^-$ | 0 | 0 | 0.744 | 848 |

*The recipe for the noted formulation from Thermo Fisher Scientific contains no glutamine. The indicated concentration is that of standard BME In some aspects, the present disclosure relates to the recognition that uric acid, at levels typical of those present in adult human blood, inhibits LIMPS. LIMPS catalyzes the final two steps of the de novo pyrimidine biosynthesis pathway to generate UMP. Without wishing to be bound by any theory, human cells cultured in cell culture media that contain an increased level of uric acid as compared to conventional culture media may have a LIMPS activity level that more closely reflects the LIMPS level of human cells in vivo than would human cells cultured in conventional culture media. In some embodiments, described herein is a cell culture medium having a concentration of uric acid that is at least about 200 μm, e.g., from about 200 μm to about 1 mM. In some embodiments the concentration is from about 200 μm to about 700 μm, e.g., from about 300 μm to about 400 μm, e.g., about 350 μm. The culture medium comprises sufficient proteinogenic amino acids, inorganic ions, sugar (s) (e.g., glucose), and vitamins to support viability and proliferation of at least some mammalian cells. In some embodiments, the culture medium may be prepared by supplementing a conventional culture medium with uric acid in an amount appropriate to achieve the selected uric acid concentration. For example, RPMI, DMEM, BME, MEM, IMDM, Ham's nutrient mixtures (e.g., F10, F12), Medium 199, McCoy's 5a, or mixtures thereof may be so supplemented. In some embodiments, cell culture media that contain an increased level of uric acid as compared to conventional culture media may be used in studies involving pyrimidine biosynthesis and/or involving compounds that act on or are acted on by enzymes involved in pyrimidine biosynthesis.

In certain embodiments, one or more of the medium components may be substituted by other chemicals of similar properties. Such modified medium without one or more non-essential/unnecessary components are within the scope of the disclosure. Similarly, a skilled artisan could, if desired, determine the optimal level of any given component for a particular cell type or application, by, for example, testing a range of concentrations (e.g., about 10%, about 25%, about 50%, about 75%, about 100%, about 2-, about 5-, about 10-, about 20-, about 50-, about 100-, about 200-, about 500-, about 1000-fold higher, or about 10%, about 25%, about 50%, about 75%, about 100%, about 2-, about 5-, about 10-, about 20-, about 50-, about 100-, about 200-, about 500-, about 1000-fold lower) for each component based on or starting from the listed concentration or range of concentrations of that particular component. In doing such tests, initial broad-range concentration tests may be narrowed down later based on the outcomes of the initial experiments. For example, for an initial test, the concentration of one component of interest may be changed to about $10^{-3}$, about $10^{-2}$, about $10^{-1}$, about 10-fold, about 100-fold, or about 1000-fold of the concentration listed in Table 2. If the about $10^{-2}$ test still supports the desired growth, while about $10^{-3}$ fails to, then the about 10-fold concentration difference between about $10^{-2}$ and about $10^{-3}$ may be further explored in the second round of test to pin-point the best ranges. Thus, media so optimized for specific cell types or applications are also within the scope of the disclosure.

As will be readily apparent to one of ordinary skill in the art, the concentration of a given ingredient can be increased or decreased beyond the ranges disclosed herein and the effect of the increased or decreased concentration can be determined. The optimization of the present media formulations for any specific cell type or application can be carried out using approaches described by Ham (Ham, *Methods for Preparation of Media, Supplements and Substrata for Serum-Free Animal Culture*, Alan R. Liss, Inc., New York, pp. 3-21, 1984) and Waymouth (Waymouth, C., *Methods for Preparation of Media, Supplements and Substrata for Serum-Free Animal Culture*, Alan R. Liss, Inc., New York, pp. 23-68, 1984). The optimal final concentrations for medium ingredients may be identified either by empirical studies, in single component titration studies, or by interpretation of historical and current scientific literature. In single component titration studies, using animal cells, the concentration of a single medium component is varied while all other constituents and variables are kept constant and the effect of the single component on viability, growth, or continued health of the animal cells is measured. Similarly, the determination of which medium component(s) are responsible for or affect a particular cellular phenotype or response can be carried out using single component titration studies, which can include entirely omitting a given non-essential component and/or testing the effect of different concentrations of such component on the cellular phenotype or response of interest.

It will be understood that certain vitamins, growth factors, hormones, or cytokines referred to herein can exist in different forms, as known in the art (e.g., different naturally occurring or non-naturally occurring forms), and can be used as substitutes for one another. Where the instant application specifies that a particular vitamin, growth factor, hormone, or cytokine is used, the disclosure should be understood to encompass embodiments in which any form of such vitamin, growth factor, hormone, or cytokine having similar biological activity (or compound(s) that can be modified or metabolized in cell culture medium or intracellularly to provide a biologically active form) is used. Amounts can be adjusted to provide equivalent biological activity.

In some embodiments, the medium ingredients can be dissolved in a liquid carrier or maintained in dry form in various embodiments. If dissolved in a liquid carrier at the preferred concentrations described herein (i.e., a "1×formulation"), the pH of the medium may be adjusted to about 7.0-7.6, e.g., about 7.1-7.5, e.g., about 7.2-7.4. The osmolality of the medium may be adjusted to the preferred ranges described above, e.g., by supplementation with NaCl. The type of liquid carrier and the method used to dissolve the ingredients into solution may vary and can be determined by one of ordinary skill in the art. Typically, the medium ingredients can be added in any order.

A cell culture medium is composed of a number of ingredients and these ingredients vary from one culture medium to another. A "1×formulation" is meant to refer to any aqueous solution that contains some or all ingredients found in a cell culture medium at working concentrations. The term "1×formulation" can refer to, for example, the cell culture medium or to any subgroup of ingredients for that medium. The concentration of an ingredient in a 1×solution is about the same as the concentration of that ingredient found in a cell culture formulation used for maintaining or cultivating cells in vitro. A cell culture medium used for the in vitro cultivation of cells is a 1×formulation by definition. When a number of ingredients are present, each ingredient in a 1×formulation has a concentration about equal to the concentration of those ingredients in a cell culture medium. For example, RPMI-1640 culture medium contains, among other ingredients, 0.2 g/L L-arginine, 0.05 g/L L-asparagine, and 0.02 g/L L-aspartic acid. A "1×formulation" of these amino acids contains about the same concentrations of these ingredients in solution. Thus, when referring to a "1×formulation," it is intended that each ingredient in solution has the same or about the same concentration as that found in the cell culture medium being described. The concentrations of ingredients in a 1×formulation of various cell culture media are well known to those of ordinary skill in the art. See, e.g., Freshney, 2010 and Liss, supra. The osmolality and/or pH, however, may differ in a 1×formulation compared to the culture medium, particularly when fewer ingredients are contained in the 1×formulation.

A "10×formulation" is meant to refer to a solution wherein each ingredient in that solution is about 10 times more concentrated than the same ingredient in the cell culture medium. For example, a 10×formulation of RPMI-1640 culture medium may contain, among other ingredients, 2.0 g/L L-arginine, 0.5 g/L L-asparagine, and 0.2 g/L L-aspartic acid (compare 1×formulation, above). A "10×formulation" may contain a number of additional ingredients at a concentration about 10 times that found in the 1×culture medium. As will be readily apparent, "25×formulation," "50×formulation," "100×formulation," "500×formulation," and "1000×formulation" designate solutions that contain ingredients at about 25-, about 50-, about 100-, about 500-, or about 1000-fold concentrations, respectively, as compared to a 1×cell culture medium. Again, the osmolality and pH of the media formulation and concentrated solution may vary. Where concentrations of components of the culture medium are referred to herein, these concentrations are for a 1×formulation unless otherwise indicated or clearly evident from the context. The disclosure also provides 10×formulations, 25×formulations, 50×formulations, 100×formulations, 250×formulations, 500×formulations, and 1000× formulations, and other formulations having intermediate concentrations between 1× and 1000×. More highly concentrated formulations can be made, provided that the ingredients remain soluble and stable. See U.S. Pat. No. 5,474,931, which is directed to methods of solubilizing culture media components at high concentrations. Certain of the components of the culture medium may be prepared as solutions at any of the afore-mentioned concentrations or higher concentrations, e.g., 2,500×, 5000, 10000× or more.

If the media ingredients are prepared as separate concentrated solutions, an appropriate (sufficient) amount of each concentrate is combined with a diluent to produce a 1×medium formulation. Typically, the diluent used is water but other solutions including aqueous buffers, aqueous saline solution, or other aqueous solutions may be used in certain embodiments.

The culture media of the present invention are typically sterilized to prevent unwanted contamination. Sterilization may be accomplished, for example, by filtration through a low protein-binding membrane filter of about 0.1-1.0 μm pore size (available commercially, for example, from Millipore, Bedford, Mass.) after admixing the concentrated ingredients to produce a sterile culture medium. Alternatively, concentrated subgroups of ingredients may be filter-sterilized and stored as sterile solutions. These sterile concentrates can then be mixed under aseptic conditions with a sterile diluent to produce a concentrated 1×sterile medium formulation. Autoclaving or other elevated temperature-based methods of sterilization are not favored, since many of the components of the present culture media are heat labile and will be irreversibly degraded by temperatures such as those achieved during most heat sterilization methods.

As will be readily apparent to one of ordinary skill in the art, each of the components of the culture medium may react with one or more other components in the solution. Thus, the present invention encompasses the formulations disclosed herein (e.g., formulations comprising the components listed in Table 2), as well as any reaction mixture which forms after these ingredients are combined.

The culture media described herein can be made from individual components separately purchased from various chemical venders such as Sigma. Table 2 lists product numbers for certain of the medium components according to the current catalogs of various vendors, but it should be understood that the components may be obtained from different vendors or synthesized.

In some embodiments, certain commercially available compositions comprising multiple components may be conveniently mixed and supplemented by additional components to make the culture medium. For example, in certain embodiments, the culture medium may comprise a RPMI 100× vitamin mix (Sigma R7256) combined with other components described herein (e.g., salts, amino acids, glucose, polar metabolites) to approximately their corresponding concentrations as described herein.

In some aspects, the disclosure provides methods of making a cell culture medium comprising combining the components disclosed herein to form any of the culture media described herein. In some aspects, the disclosure provides methods of making a cell culture medium comprising combining the components disclosed herein to form any of the basal culture media described herein and adding serum or another source of supportive substances to the basal culture medium.

Unless otherwise indicated, as used herein, variation by up to X % means variation by ±X % with respect to the listed value. For example, if the listed value is 100 uM, variation by 25% means that the value can range from about 75 uM to about 125 uM (i.e., about 75-125 uM). Unless otherwise indicated, where a range of values is disclosed, endpoints are included within the range. Embodiments are also provided in which the endpoints are excluded, and embodiments in which one endpoint is included and the other is excluded. Furthermore, it is to be understood that unless otherwise indicated or otherwise evident from the context and understanding of one of ordinary skill in the art, values that are expressed as ranges can assume any specific value or subrange within the stated ranges in various embodiments, such as to the tenth of the unit of the lower limit of the range, unless the context clearly dictates otherwise. It is also understood that where a series of numerical values is stated herein, the invention includes embodiments that relate to any intervening value or range defined by any two values in the series, where the lowest value may be taken as a minimum and the greatest value may be taken as a maximum.

It will be appreciated that certain of the components may be provided as salts, esters, biologically active metabolites or derivatives, or as precursors that are metabolized, processed, or broken down by the cell or in the medium to yield a biologically active form of certain of the components disclosed herein. "Biologically active" in this context refers to the ability of the component to exert its desired effect on a cell when present in a cell culture medium. Certain compounds, e.g., certain medium components, may exist in particular geometric or stereoisomeric forms. Such compounds, including cis- and trans-isomers, E- and Z-isomers, R- and S-enantiomers, diastereomers, (D)-isomers, (L)-isomers, (−)- and (+)-isomers, racemic mixtures thereof, and other mixtures thereof are encompassed by this disclosure in various embodiments unless otherwise indicated. Certain compounds may exist in a variety or protonation states, may have a variety of configurations, may exist as solvates (e.g., with water (i.e. hydrates) or common solvents) and/or may have different crystalline forms (e.g., polymorphs) or different tautomeric forms. Embodiments exhibiting such alternative protonation states, configurations, solvates, and forms are encompassed by the present disclosure where applicable.

The medium described herein may be liquid or solid powder, or a combination of both. In some embodiments, the liquid form may contain all the components of the medium. Alternatively, the liquid media may be stored as separate packages, such that each individual package may be stored at its appropriate conditions (temperature, humidity, etc.). For example, most or all of the components listed in Table 2 if desired to be in a medium of the present disclosure can be pre-dissolved in a single solution and stored at appropriate conditions (e.g., about 2-8° C., e.g., about 4° C., in a dark and dry place, etc.). Other components, which might be unstable over the long term at the storage conditions for the other components, or which might react slowly with other components, or which might otherwise be better kept as a separate stock, e.g., for convenience or preference, may be stored under a different set of conditions (e.g. about −20° C. or about −80° C., etc.). It is only shortly or immediately before use that these separately stored components are brought together to constitute the whole medium. Each separate package may be marketed or sold separately, or as different concentrated stocks (e.g. 2×, 5×, 10×, 100×, 1000×, etc.).

Similarly, the medium or individual components could be in the form of dry powder, which, upon reconstitution with an aqueous medium (such as water), will yield the desired medium, or its concentrated stocks (e.g., 2×, 5×, or 10×, etc.). In some embodiments, at least some components of the medium is/are in liquid/aqueous form. In some embodiments, at least some or all components of the medium is in solid/powder form. The components, e.g., stock solutions, should be appropriately stored according to the characteristics of the components, including stability at the storage temperature (e.g., liquid nitrogen, about −80 degrees C., about −20 degrees C., about 4 degrees C., room temperature or about 20-25 degrees C., etc.), sensitiveness to light, natural half-life in aqueous or organic solution, etc. Some stock solutions may preferably be remade periodically to keep a fresh stock. In some embodiments, one or more components may be prepared fresh, e.g., from a powder or more concentration solution by the user of the media and added to other components that are supplied as a liquid. In some embodiments, for example, glucose, urea, and/or uric acid may be prepared fresh. A way of preparing exemplary stock solutions is described in the Examples (see Table 7). One of ordinary skill in the art will appreciate that many other similar or equivalent methods and concentrations of stock solutions may be used. In some embodiments, the media may be provided as a set of stock solutions, powders, or both, e.g., as a kit containing multiple individual containers, each containing a stock solution or powder containing one or more of the components. The kit may include one or more diluents for dissolving components provided as powders.

To the extent that one or more components do not substantially affect (e.g., adversely affect) the performance of the medium for a desired application, the culture medium may in certain embodiments include and tolerate the presence of one or more of such components. Examples of additional components that may be present in certain embodiments of a basal medium include trace metals, lipophilic metabolites, and vitamins. In certain embodiments, the media of the present disclosure may be substantially free of any one or more of these or other components. In some embodiments, the medium is substantially free of one or more specified components. In some embodiments, "substantially free" refers to a low amount of the component that has no statistically significant effect on cell growth and/or metabolism. In some embodiments, "substantially free" refers to less than about 0.01%, about 0.001%, or about 0.0001% v/v of a liquid or w/v of a solute. In some embodiments, "substantially free" refers to a concentration of less than about 0.001 mg/L, about 0.0001 mg/L, about 0.00001 mg/L, about 0.000001 mg/L, or about 0.0000001 mg/L. In some embodiments, "substantially free" refers to a concentration of less than about 10 nM, about 1 nM, about 1 µM, about 10 µM, or about 100 µM. In some embodiments, "substantially free" refers to the medium being free of the substance, by which is meant that the substance is absent from the medium or, if present, being below the limit of detection by the most sensitive art-accepted assay for the substance, which may be a bioassay, mass spectrometry, NMR, chromatographic assay, etc.

In some embodiments, the basal culture medium is substantially free of at least the following trace metals: iron (Fe), zinc (Zn), lithium (Li), selenium (Se), chromium (Cr), copper (Cu), manganese (Mn), vanadium (Vn), molybdenum (Mo), silicon (Si), nickel (Ni), cobalt (Co), and tin (Sn). In some embodiments, one or more such trace metals may be included as a component of a basal medium or added to a basal medium or complete medium. Trace metals may be provided in a variety of forms, e.g., in the form of salts such as $CuSO_4$, $ZnSO_4$, $FeSO_4$, $Fe(NO_3)_3$), $MnCl_2$, $Na_2SeO_3$, $Na_2SiO_3$, $(NH_4)_6Mo_7O_{24}$, $NH_4VO_3$, $NiSO_4$, or $SnCl_2$. In some embodiments, any such trace metal may be present in a concentration up to about 0.25, about 0.5, about 0.75, about 1, about 1.25, about 1.5, about 2, about 2.5, or about 3 times the concentration of such trace metal in normal adult human plasma.

In some embodiments, the basal culture medium is substantially free of lipophilic metabolites. As used herein, "lipophilic metabolites" refers to compounds that comprise or are derivatives of any of the following: fatty acids, cholesterol, cholesterol ester, ceramide, diglyceride, ganglioside, glycerophosphocholine, monoacylglyceride, phosphatidic acid, phosphatidylglycerol, phosphatidylinositol, phosphatidylserine, sphingomyelin, and triglyceride. In some embodiments, one or more such lipophilic metabolites may be included as a component of a basal medium or added to a basal medium or complete medium. In some embodiments, any such lipophilic metabolite may be present in a concentration up to about 0.25, about 0.5, about 0.75, about 1, about 1.25, about 1.5, about 2, about 2.5, or about 3 times the concentration of such lipophilic metabolite in normal adult human plasma.

In some embodiments, the basal culture medium is substantially free of vitamins other than biotin, choline, folic acid, myo-inositol, niacinamide, p-aminobenzoic acid, D-pantothenic acid, vitamin B6, riboflavin, thiamine, and vitamin B12. In some embodiments, the basal culture medium comprises one or more vitamins in addition to one or more of the afore-mentioned vitamins. Additional vitamins that may be included as a component of a basal medium or added to a basal medium or complete medium include, e.g., vitamin C, vitamin D, vitamin K3, vitamin E, and vitamin A. In some embodiments, any such vitamin may be present in a concentration up to about 0.25, about 0.5, about 0.75, about 1, about 1.25, about 1.5, about 2, about 2.5, or about 3 times the concentration of such vitamin in normal adult human plasma. In some embodiments the one or more small polar metabolites is present at from about 0.5 to about 2 times the concentration of such vitamin in normal adult human plasma, e.g., from about 0.67 to about 1.5 times the concentration(s) listed for such metabolite(s) in Table 2, within about ±30%, within about ±20%, within about ±10%, or within about ±5% of the concentration of such vitamin in normal adult human plasma.

In some embodiments, the basal culture medium is substantially free of metabolites with typical concentrations in normal adult human blood of <about 6 µM, other than vitamins, which may be present as described herein. In some embodiments, one or more metabolites with a concentration in normal adult human blood of <about 6 µM may be included as a component of a basal medium or added to a basal medium or complete medium. In certain embodiments, for example, it may be of interest to compare cells cultured in a culture medium that lacks one or more specified metabolites with cells cultured in the same culture medium but with the addition of a selected metabolite or metabolites whose concentration in normal adult human blood is <6 µM. Such a comparison could include performing any of the assays described herein and comparing the results. In some embodiments, any such metabolite may be present at a concentration up to about 0.25, about 0.5, about 0.75, about 1, about 1.25, about 1.5, about 2, about 2.5, or about 3 times the concentration of such metabolite in normal adult human plasma.

In certain embodiments, any one or more metabolite(s) selected from 2-hydroxyglutarate, acetylaspartate, acetylcarnitine, acetylserine, aconitate, allantoin, aminoadipate, argininosuccinate, asymmetric dimethylarginine, beta-alanine, carnosine, cytidine, deoxycytidine, fumarate, kynurenine, malate, methionine sulfoxide, pseudouridine, ribitol, sorbitol, thymidine, trimethyllysine, uracil, uridine, xanthine, and xanthosine may be expressly included or expressly excluded in a basal medium or complete medium. In some embodiments, at least one amino acid or amino acid derivative among the foregoing list of compounds is included. In some embodiments, at least one compound comprising a purine, pyrimidine, nucleoside, nucleotide, or derivative of any of these listed in the list of compounds is included. For example, in some embodiments the medium comprises uridine, e.g., at a concentration of about 2 µM-about 4 µM. For example, in certain embodiments the culture medium contains one or more (e.g., 2, 3, or all) of acetylcarnitine, alpha-ketoglutarate, uridine, and malate.

In some embodiments, any such metabolite may be present in a concentration up to about 0.25, about 0.5, about 0.75, about 1, about 1.25, about 1.5, about 2, about 2.5, or about 3 times the concentration of such metabolite listed in Table 3. In certain embodiments the culture medium has concentrations of any one or more metabolite(s) that are from about 0.3 to about 3 times the concentration(s) listed for such metabolite(s) in Table 3, e.g., from about 0.5 to about 2 times the concentrations listed for such metabolite(s) in Table 3, e.g., from about 0.67 to about 1.5 times the concentration(s) listed for such metabolite(s) in Table 3, within about ±30% of the concentration(s) listed for such metabolite(s) in Table 3, within about ±20% of the concentration(s) listed for such metabolite(s) in Table 3, within about ±10% of the concentration(s) listed for such metabolite(s) in Table 3, within about ±5% of the concentration(s) listed for such metabolite(s) in Table 3, within about ±2% of the concentration(s) listed for such metabolite(s) in Table 3, or within about ±1% of the concentration(s) listed for such metabolite(s) in Table 3, or about equal to the concentration(s) listed for such metabolite(s) in Table 3. In certain embodiments, the culture medium has concentrations of each metabolite listed in Table 3 that is present in the medium that are between from about 0.3 to about 3 times the concentration(s) listed for such metabolite(s) in Table 3, e.g., from about 0.5 to about 2 times the concentrations listed for such metabolite(s) in Table 3, e.g., from about 0.67 to about 1.5 times the concentration(s) listed for such metabolite(s) in Table 3, within about ±30% of the concentration(s) listed for such metabolite(s) in Table 3, within about ±20% of the concentration(s) listed for such metabolite(s) in Table 3, within about ±10% of the concentration(s) listed for such metabolite(s) in Table 3, within about ±5% of the concentration(s) listed for such metabolite(s) in Table 3, within about ±2% of the concentration(s) listed for such metabolite(s) in Table 3, or within about ±1% of the concentration(s) listed for such metabolite(s) in Table 3, or about equal of the concentration(s) listed for such metabolite(s) in Table 3, or equal to the concentration(s) listed for such metabolite(s) in Table 3.

TABLE 3

| Certain additional metabolites | |
|---|---|
| Metabolite name | Concentration (uM) |
| 2-hydroxyglutarate | 0.7 |
| Acetylcarnitine | 5.79 |
| Allantoin | 2.1 |
| Aminoadipate | 2 |
| Asymmetric dimethylarginine | 0.505 |
| beta-Alanine | 2.72 |
| Carnosine | 6.54 |
| Cytidine | 0.175 |
| Deoxycytidine | 0.2 |
| Fumarate | 1.5 |
| Kynurenine | 1.8 |
| Malate | 7.6 |
| Methionine sulfoxide | 4 |
| Pseudouridine | 3.18 |
| Ribitol | 0.46 |
| Sorbitol | 7.045 |
| Thymidine | 0.205 |
| Uracil | 1.135 |
| Uridine | 3.11 |
| Xanthine, | 1.43 |
| Xanthosine | 5.08 |

In certain embodiments, the culture medium contains malate at a concentration of from 4 µM to 8 µM, such as from 5 µM to 6 µM, further such as 5 µM. In certain embodiments, the culture medium contains alpha-ketoglutarate at a concentration of from 4 µM to 8 nM, such as from 5 µM to 6 µM, further such as 5 µM. In certain embodiments, the culture medium contains acetylcarnitine at a concentration of from 4 µM to 8 µM, such as from 5 µM to 6 µM, further such as 5 µM. In certain embodiments, the culture medium contains uridine at a concentration of from 1 µM to 5 µM, such as from 2 µM to 4 µM, further such as 3 µM.

In certain embodiments, the basal cell culture medium is substantially free of any one or more of the following growth factors: EGF, FGF, IGF-1, IGF-2, PDGF, VEGF, colony-stimulating factor 1 (CSF-1), colony-stimulating factor 2 (CSF-2), and colony-stimulating factor 2 (CSF-3). In some embodiments, one or more growth factors may be added to a basal medium or complete medium. In some embodiments, any such factor may be added such that it is present in a concentration up to about 0.25, about 0.5, about 0.75, about 1, about 1.25, about 1.5, about 2, about 2.5, or about 3 times the concentration of such factor in normal adult human plasma. In certain embodiments, the basal cell culture medium is substantially free of growth factors.

In certain embodiments, the basal cell culture medium is substantially free of any one or more of the following hormones: cortisol, estrogen, growth hormone, insulin, progesterone, testosterone, and triiodothyronine (T3). In some embodiments, one or more hormones may be added to a basal medium or complete medium. In some embodiments, any such hormone may be added such that it is present in a concentration up to about 0.25, about 0.5, about 0.75, about 1, about 1.25, about 1.5, about 2, about 2.5, or about 3 times the concentration of such hormone in normal adult human plasma. In certain embodiments, the basal cell culture medium is substantially free of hormones.

In those embodiments of the culture medium that comprise serum or other at least partly undefined substance(s), any one or more metabolites, growth factors, hormones or other compounds may be present in the culture medium in the amount conferred by the serum or other at least partly undefined substance(s) in addition to the amount, if any, present in the basal medium. Growth factors, hormones, or other proteins may be recombinant proteins or may be purified from naturally occurring sources. In certain embodiments, recombinant human proteins may be used.

II. Methods of Use

Culture media described herein may be used to culture any of a wide variety of eukaryotic cells. In some embodiments, a cell used in compositions and/or methods described herein is an animal cell. In some embodiments, the cell is a mammalian cell. In some embodiments, the mammalian cell is a primate cell (human or non-human primate), rodent (e.g., mouse, rat, rabbit, hamster) cell, or canine, feline, or bovine cell. In certain embodiments of particular interest, the cells are human cells. It should be understood that cells, wherever referred to herein, may be human cells unless otherwise indicated or clearly evident from the context.

A cell may be a primary cell, immortalized cell, normal cell, abnormal cell, cancer cell, non-cancer cell, etc., in various embodiments. In some embodiments, the cell is a somatic cell. A cell may originate from a particular tissue or organ of interest or may be of a particular cell type. Primary cells may be freshly isolated from a subject or may have been passaged in culture a limited number of times, e.g., between 1-5 times or undergone a small number of population doublings in culture, e.g., 1-5 population doublings. In some embodiments, a cell is a member of a population of cells, e.g., a member of a non-immortalized or immortalized cell line. In some embodiments, a "cell line" refers to a population of cells that has been maintained in culture for at least 10 passages or at least 10 population doublings. In some embodiments, a cell line is derived from a single cell. In some embodiments, a cell line is derived from multiple cells. In some embodiments, cells of a cell line are descended from a cell or cells originating from a single sample (e.g., a sample obtained from a tumor) or individual. A cell may be a member of a cell line that is capable of prolonged proliferation in culture, e.g., for longer than about 3 months (with passaging as appropriate) or longer than about 25 population doublings). A non-immortalized cell line may, for example, be capable of undergoing between about 20-80 population doublings in culture before senescence. An immortalized cell line has acquired an essentially unlimited life span, i.e., the cell line appears to be capable of proliferating essentially indefinitely. For purposes hereof, a cell line that has undergone or is capable of undergoing at least about 100 population doublings in culture may be considered immortal.

Numerous cell lines are known in the art. Cell lines can be obtained, e.g., from depositories or cell banks such as the American Type Culture Collection (ATCC), Coriell Cell Repositories, Deutsche Sammlung von Mikroorganismen and Zellkulturen (German Collection of Microorganisms and Cell Cultures; DSMZ), European Collection of Cell Cultures (ECACC), Japanese Collection of Research Bioresources (JCRB), RIKEN, Cell Bank Australia, etc. The paper and online catalogs of the afore-mentioned depositories and cell banks are incorporated herein by reference. If desired, cells may be tested to confirm whether they are derived from a single individual or a particular cell line by any of a variety of methods known in the art such as DNA fingerprinting (e.g., short tandem repeat (STR) analysis) or single nucleotide polymorphism (SNP) analysis (which may be performed using, e.g., SNP arrays (e.g., SNP chips) or sequencing).

In certain embodiments, the cells are anchorage dependent, by which is meant that the cells require contact and anchorage to a stable surface in order to survive, function, and divide. In certain embodiments, the cells are anchorage independent, by which is meant that the cells do not require contact and anchorage to a stable surface in order to survive, function, and divide. The anchorage independent cells may be of a cell type that is normally anchorage dependent but has lost such dependence either naturally or as a result of manipulation by human intervention.

In certain embodiments, the cells comprise hematologic cells, also referred to herein as blood cells. Hematologic cells include cells of the myeloid and lymphoid lineages. Myeloid lineage cells include, but are not limited to, monocytes, macrophages, neutrophils, basophils, eosinophils, erythrocytes, megakaryocytes, and platelets. Lymphoid lineage cells include lymphocytes, e.g., T cells, B cells, and natural killer cells. T cells may comprise CD4+ helper T cells (which include Th1, Th2, and Th17 cells), CD8+ cytotoxic T cells, and/or killer T cells. In some embodiments, the hematologic cells comprise peripheral blood mononuclear cells. In some embodiments, the hematologic cells comprise dendritic cells. In certain embodiments, the cells comprise hematologic cancer cells. In some embodiments, the cells comprise endothelial cells. In some embodiments, the cells comprise epithelial cells. In some embodiments, the cells comprise hepatocytes, fibroblasts, keratinocytes, melanocytes, osteoblasts, osteoclasts, chondrocytes, neurons, glial cells, mesenchymal cells, or adipose cells.

In certain embodiments, the cells comprise stem cells. The stem cells may be pluripotent stem cells, e.g., embryonic stem cells or induced pluripotent stem (iPS) cells, or may be stem cells with a more restricted developmental potential such as adult stem cells, e.g., hematopoietic stem cells, intestinal stem cells, neural stem cells, mesenchymal stem cells, adipose-derived stem cell, or endothelial stem cells. In some embodiments, the stem cells are multipotent. In some embodiments, the stem cells are unipotent.

In certain embodiments, the cells comprise normal, non-cancer cells. In some embodiments, the cells comprise cancer cells. The cancer cells may be derived from cancers of any type, e.g., any of the cancer types mentioned herein. In some embodiments, cancer cells are genetically engineered cells, which may be generated by introducing one or more oncogenes into a non-cancer cell and/or by inactivating one or more tumor suppressor cells in a non-cancer cell. Exemplary cancer cell lines are described in the Examples. Numerous other cancer cell lines are known in the art. In some embodiments, the cancer cell line is one that is included in the Cancer Cell Line Encyclopedia (CCLE) (Barretina, J., et al., (2012) Nature 483: 603-607; portals.broadinstitute.org/ccle/home). In some embodiments, cancer cells, e.g., a cancer cell line, originates from a human tumor. In some embodiments, cancer cells, e.g., a cancer cell line, originates from a tumor that arose in a non-human animal. In some embodiments, cancer cells, e.g., a cancer cell line, originate from a naturally arising cancer (i.e., a tumor that was not intentionally induced or generated for, e.g., experimental purposes). In some embodiments, cancer cells comprise hematological cancer cells, e.g., leukemia or lymphoma cells. In some embodiments, cancer cells comprise carcinoma or sarcoma cells. In some embodiments, the cancer cells comprise cancer stem cells.

In some embodiments, cells are derived from a subject who has a disease of interest. The cells may harbor one or more mutations and/or may manifest one or more phenotypes associated with the disease. One of ordinary skill in the art is aware of numerous disease-associated mutations. A compendium of numerous human genes and disease-associated mutations that occur in humans is provided in McKusick V. A. (1998) Mendelian Inheritance in Man. A Catalog of Human Genes and Genetic Disorders, 12th Edn. The Johns Hopkins University Press, Baltimore. Md. and its online updated version Online Mendelian Inheritance in Man (OMIM), available at the National Center for Biotechnology Information (NCBI) website. One of ordinary skill in the art is aware of numerous sporadic mutations that can give rise to various diseases, e.g., cancer. In some embodiments, cells derived from a subject who has a disease of interest and/or that harbor one or more disease-associated mutations may serve as a cellular model of the disease. Such cells may be cultured in the culture medium and used, e.g., to study the disease and/or to identify or characterize potential therapeutic agents.

In some embodiments, the cells comprise genetically modified cells. Genetically modified cells encompass stable modification of the genome or introduction of a stable extrachromosomal element as well as transient modifications in which an exogenous nucleic acid that serves as a template for transcription or translation has been introduced into a cell but the sequence of the genome is not modified and the nucleic acid is not replicated and/or is lost over time as the cells divide. Methods of producing genetically modified cells are well known in the art. For example, in some embodiments, test cells are generated from an initial cell population by introduction of a vector comprising a sequence that encodes a protein or RNA of interest. A nucleic acid or vector may be introduced into cells by transfection, infection, or other methods known in the art. Cells may be contacted with an appropriate reagent (e.g., a transfection reagent) to promote uptake of a nucleic acid or vector by the cells. In some embodiments, a genetic modification is stable such that it is inherited by descendants of the cell into which a vector or nucleic acid was introduced. A stable genetic modification usually comprises alteration of a cell's genomic DNA, such as insertion of exogenous nucleic acid into the genome or deletion or replacement of one or more nucleotides of genomic DNA. It will be understood that the term "genetically modified" refers to an original genetically modified cell or cell population and descendants thereof. Thus, a genetically modified cell used in methods described herein may be a descendant of an original genetically modified cell. Genetic modification encompasses stable modification of the genome through, e.g., introduction of transgenes, gene knockouts, and genome editing such as through use of clustered regularly interspaced short palindromic repeats/CRISPR associated proteins (CRISPR/Cas) technology, transcription activator-like effector nucleases (TALENs), or zinc fingers. Modifications can include insertions, substitutions, deletions, and/or translocations in coding or noncoding regions of the genome. In some embodiments, the modification comprises inserting an epitope tag or a gene that encodes a protein that produces an optically detectable signal (e.g., emission and/or absorption of light). Such proteins include, e.g., luciferases (e.g., a firefly, *Renilla*, or *Gaussia* luciferase or luciferase enzyme from Oplophorus gracilirostris (NanoLuc [NL])) and fluorescent proteins such as green fluorescent protein (GFP). Non-limiting examples of fluorescent proteins include GFP and derivatives thereof, proteins comprising chromophores that emit light of different colors such as red, yellow, and cyan fluorescent proteins, etc. Exemplary fluorescent proteins include, e.g., Sirius, Azurite, EBFP2, TagBFP, mTurquoise, ECFP, Cerulean, TagCFP, mTFP1, mUkG1, mAG1, AcGFP1, TagGFP2, EGFP, mWasabi, EmGFP, TagYPF, EYFP, Topaz, SYFP2, Venus, Citrine, mKO, mKO2, mOrange, mOrange2, TagRFP, TagRFP-T, mStrawberry, mRuby, mCherry, mRaspberry, mKate2, mPlum, mNeptune, mTomato, T-Sapphire, mAmetrine, mKeima. See, e.g., Chalfie, M. and Kain, S R (eds.) Green fluorescent protein: properties, applications, and protocols (Methods of biochemical analysis, v. 47). Wiley-Interscience, Hoboken, N.J., 2006, and/or Chudakov, D M, et al., Physiol Rev. 90(3):1103-63, 2010 for discussion of GFP and numerous other fluorescent or luminescent proteins. In some embodiments, the genetic modification comprises generating or correcting a disease-associated mutation. In some embodiments, the genetically modified cells express an oncogene or a chimeric antigen receptor, e.g., a chimeric T cell receptor. For example, the cells may be chimeric antigen receptor (CAR) T cells.

In some embodiments, cells cultured in a culture medium of the present disclosure are a pure population of cells of a particular cell type or cell line. In some embodiments the population is at least about 80% pure, e.g., at least about 85%, about 90%, about 95%, about 99% or more pure. In some embodiments, cells of a particular type may be isolated or purified based on, e.g., cell surface marker expression. In some embodiments, two or more distinguishable populations of mammalian cells are co-cultured. The cells may be of different cell types. In some embodiments, the cells comprise cancer cells and cancer-associated cells (e.g., stromal cells). In some embodiments, the cells comprise two or more types of immune cells, e.g., a mixed population of lymphocytes. In some embodiments, multiple cells that comprise distinct DNA barcodes are cultured in the medium. Such cells may harbor different genetic modifications (e.g., knockouts of different genes).

Cells may be cultured using standard culture techniques known in the art. In some embodiments, the cells may be maintained in an approximately 5%-10% $CO_2$ environment. In some embodiments, the cells may be maintained in an approximately 2%-20% $O_2$ environment. In general, the mammalian cells may be maintained in culture at a temperature within the range typically used for culturing mammalian cells, e.g., about 36-38 degrees C., e.g., 37 degrees C. It will be understood that mammalian cells may also tolerate lower or higher temperatures. Cells may be cultured in suspension or on a surface as adherent cells. They may be cultured in various types of culture vessels such as flasks, bottles, dishes, plates, tubes, etc., which may be made of plastic, glass, or other suitable substances. The surface of such a vessel may in some embodiments be processed to render it suitable for mammalian cell culture. In some embodiments cells may be cultured in the culture medium in multiwell plates, e.g., having from 4 to 9600 wells, e.g., 6, 24, 96, 384, or 1536 wells.

In some embodiments, cells may be cultured in the medium on or in a substance that comprises one or more extracellular matrix (ECM) components such as collagen, laminin, fibronectin, proteoglycans, etc. For example, cells may be cultured in or on Matrigel®. In some aspects, cells may be cultured in a three-dimensional hydrogel or other material that can serve as a scaffold. Suitable materials include, e.g., animal ECM extract hydrogels, protein hydrogels, peptide hydrogels, polymer hydrogels comprising one or more non-polypeptide polymers, and the like. In some embodiments, the culture medium may be mixed with one or more polymers and used to produce a hydrogel. In certain embodiments, if desired, the culture media may, e.g., with addition of suitable cryopreservative(s), be used to freeze mammalian cells.

As described in further detail in the Examples, culturing mammalian cells in a culture medium of the present disclosure affected the intracellular abundances of many metabolites across multiple pathways. In some aspects, the disclosure provides a population of mammalian cells that has an altered level of one or more metabolites as compared to the level of such metabolite(s) that would be present if the mammalian cells were cultured in RPMI+10% IFS (also referred to as RPMI$^{+IFS}$).

In some aspects, the disclosure provides a population of mammalian cells that has been cultured in the culture medium for at least about 24 hours. A population of cells is considered to have been cultured in a particular culture medium for a given length of time X if the cells are descended from one or more cells that were first placed into that culture medium at least that length of time ago and culture in the medium has continued uninterrupted since that time (with replacement by fresh media as appropriate). In some embodiments, the disclosure provides a population of mammalian cells that has been cultured in culture medium of the present disclosure for at least about 2, about 3, about 4, about 5, about 7, about 14, about 21, or about 28 days, or more. In some embodiments, the disclosure provides a population of mammalian cells that has been cultured in culture medium of the present disclosure for at least 1, 2, 3, 5, 10, 15, 20, or 25 passages, or more. In some embodiments, the disclosure provides a population of mammalian cells that has been cultured in culture medium of the present disclosure for at least 1, 2, 3, 5, 10, 15, 20, or 25 cell doubling times, or more.

As described in the Examples, in some embodiments, cells cultured in a culture medium as disclosed herein were found to have increased intracellular levels of carbamoylaspartate, dihydroorotate, orotate, and/or orotidine than cells of the same cell line cultured in RPMI$^{+IFS}$. In some aspects, the disclosure provides a mammalian cell or mammalian cell population having intracellular concentrations of carbamoylaspartate, dihydroorotate, orotate, and/or orotidine that is/are at least 2-fold higher (e.g., between 2-fold and about 1500-fold higher) than the intracellular concentration(s) of such metabolite(s) when the cell(s) are cultured in RPMI$^{+IFS}$.

In some aspects, the disclosure provides a mammalian cell or cell population having an intracellular concentration of uric acid that is at least about 2-fold (e.g., from about 2-fold to about 1500-fold higher) than the intracellular concentration(s) of uric acid when the cell(s) are cultured in RPMI$^{+IFS}$. In some aspects, the disclosure provides a mammalian cell or cell population having an intracellular concentration of uric acid that is at least about 50 µm, e.g., from about 50 µm to about 1500 µm, e.g., from about 100 µm to about 500 µm, from about 500 µm to about 1000 µm, or from about 1000 µm to about 1500 µm, e.g., about 1000 µm or about 1100 µm.

In some aspects, culture medium of the present disclosure may be used to culture mammalian cells on which one or more assays is performed. Numerous assays that make use of mammalian cells are known in the art. Assays may be used for a wide variety of purposes. For example, they may be used to identify candidate therapeutic agents or to characterize agents for activity, e.g., for potential therapeutic or toxic activity, for inhibitory or stimulating effect on the expression or activity of one or more endogenous gene products (e.g., proteins) or biological pathways, or to identify genes that affect one or more cell phenotypes of interest. A screen may comprise performing an assay on a population or multiple individual populations of cells that are subjected to different perturbations. The perturbations may be, e.g., exposure to different compounds and/or genetic modifications. A screen may be performed to identify agent(s) or gene(s) that may have an effect of interest on cells or gene products. An effect of interest may be, e.g., an anti-proliferative effect, a proliferation-promoting effect, a pro-apoptotic effect, an anti-apoptotic effect, an inhibitory effect, an activating effect, etc. In some embodiments, a screen comprises testing at least about 10, at least about 100, at least about 1,000, at least about 10,000 or more different test agents or genetic modifications. Assays may be performed on whole cells or on organelles isolated from cells (e.g., mitochondria, nuclei), cell lysates, proteins, RNA, or other cell constituents.

"Agent" as used herein refers to any substance, molecule, supramolecular complex, material, or combination or mixture thereof. The term "agent" is used interchangeably with "compound" herein. In some aspects, an agent can be represented by a chemical formula, chemical structure, or sequence. Example of agents, include, e.g., small molecules, polypeptides, nucleic acids (e.g., RNAi agents such as short interfering RNAs, antisense oligonucleotide, aptamers), lipids, polysaccharides, etc. In some embodiments, an agent is cell-permeable, e.g., within the range of typical agents that are taken up by cells and acts intracellularly, e.g., within mammalian cells, to produce a biological effect. "Test agent" refers to any agent that is to be tested or is being tested or has been tested with respect to its effect on or interaction with cells. Testing can comprise any type of characterization or analysis of the effect of a test agent on cells. Any of the agents described herein may be used as a test agent. In some embodiments, a test agent is not any of the compounds that are described herein as components of the culture medium.

In some embodiments an agent is a small molecule. As used herein, "small molecule" refers to an organic compound that is less than about 2 kilodaltons (kDa) in mass. In some embodiments, the small molecule is less than about 1.5 kDa, or less than about 1 kDa. In some embodiments, the small molecule is less than about 800 daltons (Da), about 600 Da, about 500 Da, about 400 Da, about 300 Da, about 200 Da, or about 100 Da. Often, a small molecule has a mass of at least about 50 Da. In some embodiments, a small molecule is non-polymeric. In some embodiments, a small molecule is not an amino acid or amino acid derivative. In some embodiments, a small molecule is not a nucleotide. In some embodiments, a small molecule is not a saccharide. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments, at least two functional groups. Small molecules often comprise one or more cyclic carbon or heterocyclic structures and/or aromatic or polyaromatic structures, optionally substituted with one or more of the above functional groups. It will be appreciated that small molecules encompass both electrically neutral compounds as well as polyatomic ions, which may be provided as salts.

In some embodiments, an agent is an approved drug. "Approved drug" means an agent or composition that has been approved by a government regulatory agency (such as the US FDA or government agencies having similar authority over the approval of therapeutic agents in other jurisdictions), such that the agent or composition is allowed to be marketed, promoted, distributed, sold or otherwise provided commercially for treatment of humans or for veterinary purposes.

In some embodiments, an agent is an enzyme modulator or receptor modulator. "Modulate" (and related terms such as "modulating", "modulates") means causing or facilitating a qualitative or quantitative change, alteration, or modification in a molecule, process, pathway, or phenomenon of interest. "Modulate" encompasses causing an increase or decrease in the level or activity of a molecule, process, pathway, or phenomenon of interest, e.g., inhibiting or activating the molecule, process, pathway, or phenomenon of interest.

In some embodiments an agent comprises a detectable label. As used herein, a "detectable label" refers to a moiety that has at least one element, isotope, or functional group incorporated into the moiety which enables detection of the molecule, e.g., a small molecule, nucleic acid, or polypeptide, or other entity, to which the label is attached. Labels can be directly attached (i.e., via a bond) or can be attached by a tether. It will be appreciated that the label may be attached to or incorporated into a molecule, for example, a small molecule, polypeptide, or other entity, at any position. In general, a label can fall into any one (or more) of five classes: a) a label which contains isotopic moieties, which may be radioactive or heavy isotopes, including, but not limited to $^{2}$H, $^{3}$H, $^{13}$C, $^{14}$C, $^{15}$N, $^{18}$F, $^{31}$P, $^{32}$P, $^{35}$S, $^{67}$Ga, $^{76}$Br, $^{99m}$Tc (Tc-99m), $^{111}$In, $^{123}$I, $^{125}$I, $^{131}$I, $^{153}$Gd, $^{169}$Yb, and $^{186}$Re; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label fluorescein isothiocyanate (FITC); d) a label which has one or more photo affinity moieties; and e) a label which is a ligand for one or more known binding partners (e.g., biotin-streptavidin, FK506-FKBP). In certain embodiments, a label comprises a radioactive isotope, e.g., an isotope which emits detectable particles, such as beta particles. In certain embodiments an agent comprises a radiolabeled sugar, amino acid, purine, pyrimidine, nucleoside, or nucleotide.

In some embodiments, an agent is an anti-cancer agent. "Anti-cancer agent" refers to agents that are used or in development for the treatment of cancer. Such agents include a variety of small molecules, proteins (e.g., monoclonal antibodies), as well as cellular therapies such as adoptive cell transfer. "Anti-cancer agent" includes relatively non-specific cytotoxic or cytostatic agents, e.g., those that inhibit mitosis (also referred to as "chemotherapeutic agents"), as well as those agents that more selectively block extracellular growth signals (e.g., blockers of signal transduction) and blockers of growth promoting signals coming from classic endocrine hormones (primarily estrogens for breast cancer and androgens for prostate cancer). Chemotherapeutic agents include, e.g., alkylating and alkylating-like agents such as nitrogen mustards (e.g., chlorambucil, chlormethine, cyclophosphamide, ifosfamide, and melphalan), nitrosoureas (e.g., carmustine, fotemustine, lomustine, streptozocin); platinum agents (e.g., alkylating-like agents such as carboplatin, cisplatin, oxaliplatin, BBR3464, satraplatin), busulfan, dacarbazine, procarbazine, temozolomide, thioIEPA, treosulfan, and uramustine; antimetabolites such as folic acids (e.g., aminopterin, methotrexate, pemetrexed, raltitrexed); purines such as cladribine, clofarabine, fludarabine, mercaptopurine, pentostatin, thioguanine; pyrimidines such as capecitabine, cytarabine, fluorouracil, floxuridine, gemcitabine; spindle poisons/mitotic inhibitors such as taxanes (e.g., docetaxel, paclitaxel), vincas (e.g., vinblastine, vincristine, vindesine, and vinorelbine), epothilones; cytotoxic/anti-tumor antibiotics such anthracyclines (e.g., daunorubicin, doxorubicin, epirubicin, idarubicin, mitoxantrone, pixantrone, and valrubicin), compounds naturally produced by various species of *Streptomyces* (e.g., actinomycin, bleomycin, mitomycin, plicamycin) and hydroxyurea; topoisomerase inhibitors such as camptotheca (e.g., camptothecin, topotecan, irinotecan) and podophyllums (e.g., etoposide, teniposide). Other anti-cancer agents include monoclonal antibodies for cancer therapy such as anti-receptor tyrosine kinase antibodies (e.g., cetuximab, panitumumab, trastuzumab), anti-CD20 (e.g., rituximab and tositumomab), and others for example, alemtuzumab, bevacizumab, gemtuzumab; photosensitizers such as aminolevulinic acid, methyl aminolevulinate, porfimer sodium, and verteporfin; tyrosine and/or serine/threonine kinase inhibitors, e.g., inhibitors of Abl, Kit, insulin receptor family member(s), VEGF receptor family member(s), EGF receptor family member(s), PDGF receptor family member(s), FGF receptor family member(s), mTOR, Raf kinase family members, phosphatidyl inositol (PI) kinases such as PI3 kinase, PI kinase-like kinase family members, MEK kinase family members, JAK kinase family members, cyclin dependent kinase (CDK) family members, Aurora kinase family members. Kinase inhibitors that are on the market for treatment of cancer or have shown efficacy in at least one phase III trial in cancer include cediranib, crizotinib, dasatinib, dabrafenib, erlotinib, everolimus, gefitinib, imatinib, lapatinib, nilotinib, sorafenib, sunitinib, tofacitinib, temsirolimus, trametinib, vandetanib, amd vemurafinib. Yet other anti-cancer agents include growth factor receptor antagonists; retinoids (e.g., alitretinoin and tretinoin), altretamine, amsacrine, anagrelide, arsenic trioxide, asparaginase (e.g., pegasparagase), bexarotene, denileukin diftitox, estramustine, ixabepilone, masoprocol, mitotane, and testolactone, Hsp90 inhibitors, proteasome inhibitors (e.g., bortezomib, carfilzomib, ixazomib, delanzomib, oprozomib and marizomib); angiogenesis inhibitors, e.g., anti-vascular endothelial growth factor agents such as bevacizumab (Avastin) or agents comprising a soluble VEGF receptor domain (e.g., aflibercept), matrix metalloproteinase inhibitors, pro-apoptotic agents (e.g., apoptosis inducers such as Bcl-2 inhibitors (e.g., obatoclax, navitoclax, gossypol), Ras inhibitors; cancer vaccines; other immunomodulating therapies such as checkpoint inhibitors (e.g., monoclonal antibodies that bind to immune checkpoint molecules, e.g., CTLA4 inhibitors such as ipilimumab, PD-1 inhibitors such as nivolumab and pembrolizumab, PD-L1 antagonists such as atezolizumab); RNAi agents targeted to oncogenes, etc. It will be understood that a number of anti-cancer agents have multiple activities or mechanisms of action and could be classified in multiple categories or classes or have additional mechanisms of action or targets.

The effect of an agent or genetic modification on cell viability, proliferation, gene expression, protein activity, morphology, migration, or any other cell property, process, phenotype, or biological pathway may be measured using any suitable method. In certain embodiments, survival and/or proliferation of a cell or cell population may be determined by a cell counting assay (e.g., using visual inspection, automated image analysis, flow cytometer, etc.), a replication assay, a cell membrane integrity assay, a cellular ATP-based assay, a mitochondrial reductase activity assay, a BrdU, EdU, or H3-Thymidine incorporation assay, calcein staining, a DNA content assay using a nucleic acid dye, such as Hoechst Dye, DAPI, Actinomycin D, 7-aminoactinomycin D or propidium iodide, a cellular metabolism assay such as resazurin (sometimes known as AlamarBlue or by various other names), MTT, XTT, and CellTitre Glo, etc., a protein content assay such as SRB (sulforhodamine B) assay; nuclear fragmentation assays; cytoplasmic histone associated DNA fragmentation assay; PARP cleavage assay; TUNEL staining; or annexin staining. In some embodiments, cell survival or proliferation is assessed by measuring expression of one or more genes that encode gene products that mediate cell survival or proliferation or cell death, e.g., genes that encode products that play roles in or regulate the cell cycle or cell death (e.g., apoptosis). Examples of such genes include, e.g., cyclin dependent kinases, cyclins, BAX/BCL2 family members, caspases, etc. One of ordinary skill in the art will be able to select appropriate genes to be used as indicators of cell survival or proliferation. In some embodiments, an assay of cell survival and/or proliferation may determine cell number, e.g., number of living cells, and may not distinguish specifically between cell survival per se and cell proliferation, e.g., the assay result may reflect a combination of survival and proliferation. In some embodiments, an assay able to specifically assess survival or proliferation or cell death (e.g., apoptosis or necrosis) may be used.

In some aspects, the culture media may find particular use in analyzing cellular metabolism and/or identifying or characterizing agents that act via or interact with cellular metabolites or metabolic pathways. Conventional culture media and mouse plasma poorly reflect the metabolite composition of human plasma. As described in the Examples, culture in an embodiment of the inventive culture medium (referred to as HPLM and supplemented with 10% IFS), which better reflects the metabolite composition of human plasma than do conventional media, had widespread effects on cellular metabolism compared to culture in a standard media. Among the most significant were alterations in the intracellular abundance of metabolites involved in pyrimidine metabolism. This effect was traced to uric acid, whose plasma concentration is up to an order of magnitude greater in humans than in most other mammals, including mouse and cow (Álvarez-Lario and Macarrón-Vicente, 2010; Kratzer et al., 2014; Wu et al., 1992). Uric acid, at concentrations present in human plasma, is an endogenous inhibitor of UMP synthase (LIMPS), an enzyme that catalyzes the final two steps of the de novo pyrimidine biosynthesis pathway. Similar to other small molecule inhibitors of LIMPS, uric acid induces an accumulation of orotate, which in turn, antagonizes the metabolism of 5-FU to the fluoronucleotide derivatives that mediate its cytotoxic effects. Disclosed culture mediums can enable study, for example, cellular metabolism and identify new tumor-specific liabilities or metabolite-drug interactions that are influenced by environmental metabolic composition.

As described in the Examples, various human hematologic cancers proliferated in HPLM$^{+dIFS}$ at rates that were comparable, albeit generally lower, to those in RPMI$^{+IFS}$ and RPMI$^{+dIFS}$. Without wishing to be bound by any theory, assays aimed at predicting the effect of agents on human cell proliferation in vivo may be more accurate if performed using the disclosed culture media than in conventional cell culture media.

In some embodiments, an assay comprises measuring (i) the level of one or more intracellular substances (e.g., metabolites, RNA, protein), (ii) the secretion of one or more substances (e.g., metabolites, secreted proteins) into the media, (iii) the redox state, (iv) glucose utilization; or (v) the level of activity of one or more metabolic pathways, cell signaling pathways, or enzymes. One of ordinary skill in the art is aware of appropriate assays that can be used to detect or measure the level of metabolites, RNA, and proteins. For example, metabolites may be detected or measured using mass spectrometry (which may be preceded by separation using, e.g., gas chromatography, high performance liquid chromatography, or mass spectrometry), nuclear magnetic resonance (NMR), ion-mobility spectrometry, electrochemical detection (coupled to HPLC), Raman spectroscopy, or radiolabel. RNA may be detected or measured using methods that involve hybridization and/or amplification such as Northern blot, microarrays, nCounter technology, quantitative reverse transcription PCR, or by sequencing-based approaches such as serial analysis of gene expression (SAGE) or RNA sequencing (RNA-Seq). Proteins may be measured using immunological methods using an antibody that binds to the protein to be detected or other affinity-based methods. Exemplary methods that can be used to detect and measure proteins include, e.g., immunohistochemistry (IHC); enzyme-linked immunosorbent assay (ELISA), bead-based assays such as the Luminex® assay platform, flow cytometry, protein microarrays, surface plasmon resonance assays, immunoprecipitation, immunoblot (Western blot), and mass spectrometry. Other assays of interest that could be performed on cells include, e.g., reporter assays, ChIP-chip, ChIP-Seq, bisulfite sequencing, and chromosome conformation capture. In some embodiments, an assay comprises detecting DNA modifications (such as methylation), protein modifications (e.g., histone modifications or protein phosphorylation), transcription, or DNA repair. In some embodiments, an assay is performed using cells cultured in the culture medium in the presence of a test agent and the result is compared with a reference value. The reference value may be the result obtained when the same assay is performed using cells of the same type in the absence of the test agent. If the result differs from the reference value, it may be concluded that the test agent affects the level or activity of a molecule, pathway, or process being measured in the assay.

Metabolic pathways of interest include, e.g., glycolysis, oxidative phosphorylation, purine biosynthesis, pyrimidine biosynthesis, fatty acid biosynthesis, to name a few. In some embodiments, cells cultured in the culture medium may be used to identify or characterize agents that may affect glucose metabolism, lipid metabolism, DNA or RNA synthesis, and oxidative phosphorylation. Defects in such processes are involved in a wide range of human diseases, including, for example, cardiovascular disease, diabetes, atherosclerosis, and metabolic syndrome. Cells cultured in the culture medium may be used to identify or characterize agents that could be potentially useful in treating such diseases, e.g., correcting metabolic defects associated with such diseases.

Cell signaling pathways of interest include, e.g., the TGFβ, Wnt, BMP, Notch, Hedgehog, HGF-Met, EGF, IGF, PDGF, FGF, P38-MAP kinase, Ras, PI3Kinase-Akt, Src, and NF-kB pathways. In some embodiments, an assay comprises identifying or characterizing an agent that inhibits or activates one or more of said pathways.

In some embodiments, an assay comprises detecting apoptosis, necrosis, autophagy, migration, epithelial-mesenchymal transition, T cell activation, T cell effector functions, or any functional activity of a cell.

In some embodiments, the cells may be contacted with a detectable label during or after culturing in the culture medium. In some embodiments, an assay comprises imaging or fluorescence activated cell sorting.

In some embodiments, an agent or combination of agents is tested to determine whether it has an anti-cancer effect or to quantify an anti-cancer effect using cells cultured in the culture medium. In some embodiments, an anti-cancer effect is inhibition of cancer cell survival or proliferation. It will be understood that inhibition of cell proliferation or survival by an agent or combination of agents may, or may not, be complete. For example, cell proliferation may, or may not, be decreased to a state of complete arrest for an effect to be considered one of inhibition or reduction of cell proliferation. In some embodiments, "inhibition" may comprise inhibiting proliferation of a cell that is in a non-proliferating state (e.g., a cell that is in the $G_0$ state, also referred to as "quiescent") and/or inhibiting proliferation of a proliferating cell (e.g., a cell that is not quiescent). Similarly, inhibition of cell survival may refer to killing of a cell, or cells, such as by causing or contributing to necrosis or apoptosis, and/or the process of rendering a cell susceptible to death, e.g., causing or increasing the propensity of a cell to undergo apoptosis or necrosis. The inhibition may be at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, or about 100% of a reference level (e.g., a control level). In some embodiments, an anti-cancer effect is inhibition of the capacity of cancer cells to form colonies in suspension culture or in a semi-solid medium such as soft agar or methylcellulose or to grow on a low attachment surface such as poly(2-hydroxyethyl methacrylate). In some embodiments, an anti-cancer effect is inhibition of capacity of the one or more cancer cells to form tumor spheres in culture. The cancer cells may be cultured in the culture medium prior to and/or during the colony-forming assay, growth assay, or tumor sphere forming assay. In some embodiments, an anti-cancer effect is inhibition of the capacity of the one or more cancer cells to form cancers in vivo after introduction into a non-human mammal, e.g., a mouse.

In some embodiments, an assay comprises measuring the growth rate of cells cultured in a culture medium disclosed herein. In some embodiments, the cells are cultured in medium to which a test agent has been added. In some embodiments, an assay comprises measuring the $EC_{50}$ of a test agent using cells cultured in medium to which the test agent has been added.

In some embodiments, an assay is performed using cells cultured in the culture medium, and the result is compared with the result obtained when the same assay is performed using cells of the same type but cultured in a conventional culture medium (e.g., $RPMI^{+IFS}$). If there is a difference in the results, it can be concluded that the test agent (or its activity) or cellular process, property, phenotype, or biological pathway being analyzed or tested in the assay is affected by environmental metabolic composition. If desired, the particular metabolite(s) that affect the test agent, activity, cellular process, property, phenotype, or biological pathway can be identified, e.g., by systematically omitting one or more metabolites or group of metabolites from the culture medium and determining which resulting culture media produce results that no longer exhibit the effect. If omission of a particular metabolite or group of metabolites largely or completely abolishes the effect, it can be inferred that such metabolite(s) are responsible for the effect. The method may be used, for example, to identify metabolite-drug interactions that may affect efficacy and/or toxicity of therapeutic agents.

In some aspects, an assay may comprise comparing the effect of one or more agents or genetic modifications on cancer cells with the effect of such agents or genetic modifications on non-cancer cells (e.g., non-cancer cells of the same cell type as the cancer cells) or comparing the effect of one or more agents or genetic modifications on two or more different types of cancer cells. Such comparisons may, for example, identify tumor-specific liabilities (vulnerabilities that are present or more marked in cancer cells (or particular cancer types) as compared with non-cancer cells), which may then be developed for therapeutic purposes.

In some embodiments, cells cultured in the culture media may be used for personalized medicine. For example, cells may be isolated from a subject, cultured in the medium, and used to test the effect of one or more therapeutic agents, e.g., to identify an agent or combination of agents that effectively kill the cells. In certain embodiments, the cells comprise cancer cells, and the method may be used to select an appropriate agent or combination of agents to treat the subject. The term "subject" as used herein in reference to an individual from whom cells may be isolated and/or to whom an agent may be administered, refers to any animal. In certain embodiments, the subject is a mammal. In certain embodiments of particular interest, the term "subject" refers to a human.

In some embodiments, cells cultured in the culture media disclosed herein may be used for cell therapy purposes. In such embodiments, the culture medium may be free of serum and other at least partly uncharacterized animal-derived products. "Cell therapy" refers to the introduction of living cells into the body of a subject for therapeutic purposes. The cells may be autologous or non-autologous. Cell therapy encompasses adoptive immunotherapy (in which immune cells such as T cells are introduced into the subject), cell or tissue transplants (e.g., stem cell or progenitor cell therapy, e.g., for regenerative medicine purposes), and introduction of cells that have the capacity to release soluble factors such as cytokines, chemokines, and growth factors. Without wishing to be bound by any theory, cells or tissues that have been cultured in the culture medium containing small polar compounds that are found in adult human blood, but are not present in conventional culture media, may be better adapted to conditions they will encounter once introduced into the recipient than would cells or tissues cultured in media that lacks such components. Without wishing to be bound by any theory, cells or tissues that have been cultured in the culture medium containing small polar compounds that are found in adult human blood, but are not present in conventional culture media, may survive and/or function more effectively once introduced into the recipient than would cells or tissues cultured in media that lacks such components.

In some embodiments, cells cultured in the disclosed culture media may be used for diagnostic purposes. For example, cells may be derived from a subject suspected of having a disorder, e.g., a metabolic disorder, and cultured in the medium, and the level of one or more intracellular or secreted metabolites may subsequently be measured and compared with a reference level. The reference level may be, e.g., the level of such metabolite(s) that is present in or secreted by control cells derived from a healthy subject or the level of such metabolite(s) that is present in or secreted by cells derived from a subject who is known to have a particular disorder.

In some embodiments, cells cultured in the culture media may be used to produce a product of interest, such as a therapeutically useful protein.

III. Additional Methods and Compositions

In some aspects, Uric acid can act as an inhibitor of UMP synthase (UMPS), the enzyme that catalyzes the final two steps of the de novo pyrimidine biosynthesis pathway. Described herein is a method of modulating the activity of UMPS in a mammalian cell, the method comprising contacting the cell with an agent that modulates uric acid levels in the cell. In some embodiments, the method comprises contacting the cell with an agent that increases uric acid levels, thereby inhibiting UMPS. In some embodiments, the method comprises contacting the cell with an agent that lowers uric acid levels, thereby increasing the activity of UMPS. Also described herein is a method of modulating the activity of UMPS in a mammalian subject, the method comprising administering an agent that modulates uric acid levels to the subject. In some embodiments, the method comprises administering a uric acid lowering agent to the subject, thereby increasing the activity of UMPS. In some embodiments, the method comprises administering a uric acid elevating agent to the subject, thereby decreasing the activity of UMPS.

In some aspects, the disclosure provides the insight that an intracellular metabolite may affect the activity of a therapeutic agent. For example, a metabolite may inhibit a therapeutic agent, thereby reducing its efficacy. The metabolite may affect the activity of the therapeutic agent directly (i.e., by binding to it) or indirectly. Indirect inhibition may result from the metabolite modulating, e.g., inhibiting, the activity of an intracellular enzyme. The intracellular enzyme may be one that acts on the therapeutic agent to convert it into a more active form.

In some aspects, described herein is a method of modulating the activity of a therapeutic agent, the method comprising modulating the intracellular level of a metabolite that affects the activity of the therapeutic agent. In some embodiments, the metabolite increases the activity of the therapeutic agent, thereby increasing its efficacy, and the method comprises increasing the level of the metabolite. The level of the metabolite may be increased by, e.g., administering the metabolite itself, administering a precursor of the metabolite, or administering an agent that causes decreased excretion of the metabolite or increased production of the metabolite. In some embodiments, the metabolite reduces the activity of the therapeutic agent, thereby reducing its efficacy, and the method comprises lowering the level of the metabolite. The level of the metabolite may be lowered by, e.g., administering an agent that causes increased excretion or decreased production of the metabolite or that degrades the metabolite. Certain methods of modulating the activity of a therapeutic agent are exemplified herein, wherein the therapeutic agent is 5-flurouracil (5-FU; CAS Registry No. 51-21-8) or a 5-FU prodrug and the metabolite is uric acid. For example, as described herein, uric acid inhibits LIMPS. By inhibiting LIMPS, uric acid induces an accumulation of orotate, which in turn, antagonizes the metabolism of 5-FU to the fluoronucleotide derivatives that mediate its cytotoxic effects. For example, orotate competes with 5-FU for its direct conversion to FUMP by the orotate phosphoribosyltransferase (OPRT) domain of LIMPS. Thus, uric acid, at concentrations typical of those found in human plasma, inhibits the activity of 5-FU. However, the disclosed methods are applicable to other therapeutic agents and metabolites. In some embodiments, the therapeutic agent is an anti-cancer agent. In some embodiments, the therapeutic agent is an anti-metabolite. In some embodiments, the therapeutic agent is purine analog, pyrimidine analog, nucleoside analog, or nucleotide analog.

In certain embodiments, the therapeutic agent is 5-FU or a 5-FU prodrug. The term "prodrug" as used herein, refers to a compound that, following administration to a subject, is converted to a pharmacologically active, or more pharmacologically active, compound. 5-FU is itself a prodrug. 5-FU and 5-FU prodrugs are used in the treatment of a wide variety of cancers. "Cancer" refers to a class of diseases characterized by the development of abnormal cells (cancer cells) that proliferate uncontrollably and have the ability to infiltrate and destroy normal body tissues. The term "cancer" may be used interchangeably with "tumor" or "neoplasm" herein and may be used to refer to a particular solid tumor mass or group of cancer cells in a subject as well as to the disease itself. Cancers include those diseases characterized by formation of malignant solid tumor masses (e.g., carcinomas, sarcomas) and also hematologic cancers such as leukemias in which there may be no detectable solid tumor mass. As used herein, the term "cancer" includes, but is not limited to, the following types of cancer: breast cancer; biliary tract cancer; bladder cancer; brain cancer (e.g., glioblastomas (e.g., astrocytomas), medulloblastomas); cervical cancer; choriocarcinoma; colon cancer; endometrial cancer; esophageal cancer; gastric cancer; hematologic cancers; intraepithelial neoplasms including Bowen's disease and Paget's disease; liver cancer (e.g., hepatocellular carcinoma); lung cancer (e.g., bronchogenic carcinoma, small cell lung cancer (SCLC), non-small cell lung cancer (NSCLC), adenocarcinoma of the lung); lymphomas including Hodgkin's disease and non-Hodgkin's lymphomas; neuroblastoma; melanoma; ocular cancer (e.g., intraocular melanoma, retinoblastoma); oral cancer (e.g., oral squamous cell carcinoma); ovarian cancer (e.g., arising from epithelial cells, stromal cells, germ cells, or mesenchymal cells); pancreatic cancer; prostate cancer; rectal cancer; anal cancer; sarcomas including angiosarcoma, gastrointestinal stromal tumors, leiomyosarcoma, rhabdomyosarcoma, liposarcoma, fibrosarcoma, and osteosarcoma; renal cancer including renal cell carcinoma and Wilms tumor; skin cancer including basal cell carcinoma and squamous cell cancer; testicular cancer including germinal tumors such as seminoma, non-seminoma (teratomas, choriocarcinomas), stromal tumors, and germ cell tumors; throat cancer (e.g., laryngeal cancer, pharyngeal cancer, nasopharyngeal cancer, oropharyngeal cancer), thyroid cancer (e.g., thyroid adenocarcinoma and medullary carcinoma). "Carcinoma" refers to a cancer arising or believed to have arisen from epithelial cells, e.g., cells of the cancer possess various molecular, cellular, and/or histological characteristics typical of epithelial cells. "Hematologic cancer" refers to cancers of the hematopoietic and lymphoid tissues. Hematologic cancers include, e.g., leukemias, lymphomas, multiple myeloma, other malignant plasma cell neoplasms such as extramedullary plasmacytoma, myelodysplastic syndromes, and myeloproliferative diseases. Leukemias include, e.g., myeloid leukemias (e.g., acute myeloid leukemia (AML, also known as acute myelogenous leukemia or acute nonlymphocytic leukemia), acute promyelocytic leukemia (APL), acute myelomonocytic leukemia (AMMoL)), chronic myeloid leukemia (CML)) and lymphoid leukemias (e.g., acute lymphocytic leukemia (ALL, also referred to as acute lymphoblastic leukemia), chronic lymphocytic leukemia (CLL), and hairy cell leukemia). Lymphomas include, e.g., non-Hodgkin's lymphomas (e.g., B cell lymphomas (e.g., mantle cell lymphoma, small B cell lymphoma, diffuse large B cell lymphoma, Burkitt's lymphoma, Waldenström's macroglobulinemia (also known as lymphoplasmacytic lymphoma)), T cell lymphomas (e.g., anaplastic large cell lymphoma (e.g., ALK positive or ALK negative), peripheral T cell lymphoma, adult T-cell leukemia/lymphoma), and NK cell lymphomas) and Hodgkin's lymphoma.

5-FU prodrugs include the fluoropyrimidines capecitabine (CAS Registry No. 154361-50-9) and tegafur (CAS Registry No. 0017902-23-7). In accordance with certain embodiments of the present disclosure, the activity of a fluoropyrimidine, e.g., 5-FU, in a mammalian subject, e.g., a human subject, is enhanced by administering a uric acid lowering agent to the subject. The disclosure provides a method of treating a subject in need of treatment for cancer, the method comprising administering 5-FU, a 5-FU prodrug, or a uric acid lowering agent to the subject, so that the subject is exposed to both 5-FU and the uric acid lowering agent. Thus, in some aspects, the disclosure provides a combination therapy comprising (i) 5-FU or a 5-FU prodrug and (ii) a uric acid lowering agent. "Combination therapy" as used herein, refers to administration of two or more agents such that the subject is exposed to both agents at the same time and/or administration of two or more agents according to a predetermined dosing scheme that specifies administration of two or more agents within a time interval that allows the agents to together achieve an overall improved therapeutic effect (which may be increased efficacy, reduced side effects, or both) relative to administration of either agent (or any subcombination of the agents in the case of 3 or more agents) alone. In some embodiments, the two or more agents may be administered within 24, 48, or 72 hours of each other. In some embodiments, the two or more agents may be administered, within 1, 2, or 4 weeks of each other. In some embodiments, 5-FU or a 5-FU prodrug and a uric acid lowering agent are administered in the same composition. In some embodiments, 5-FU or a 5-FU prodrug and a uric acid lowering agent are administered in separate compositions. When administered in separate compositions, the two or more agents may in some embodiments be administered within, e.g., up to 24, 48, or 72 hours apart or, in some embodiments, up to 1, 2, 3, or 4 weeks apart. In some embodiments, a uric acid lowering agent may be administered at least once up to 24, 48, or 72 hours prior to administration of -FU or a 5-FU prodrug, or vice versa. In some embodiments, a uric acid lowering agent may be administered at least once up to 1, 2, 3, or 4 weeks prior to administration of -FU or a 5-FU prodrug, or vice versa. It will be understood that multiple doses of each agent may be administered (e.g., over a period of weeks or months). In some embodiments, one or more courses of treatment are administered.

In some embodiments, the cancer is selected from anal, breast, colorectal, esophageal, head and neck cancer, pancreatic, stomach, and skin cancers.

In some embodiments, a cancer comprises cancer cells that (e.g., in the absence of inhibition by uric acid) generate FUMP at least in part via OPRT-mediated synthesis. For example, in some embodiments, at least about 25%, at least about 50%, at least about 75%, or more of the FUMP generated in the cancer (e.g., in the absence of inhibition by uric acid) is generated via OPRT-mediated synthesis.

In some embodiments, the subject may also be treated with an agent that increases 5-FU bioavailability, such as an inhibitor of the enzyme dihydropyrimidine dehydrogenase (e.g., uracil, eniluracil, or gimeracil) and/or an agent that decreases 5-FU toxicity such as an inhibitor of the enzyme orotate phosphoribosyltransferase (e.g., oteracil). The method of treating cancer may further comprise administering one or more such agent(s) to the subject. One of ordinary skill in the art appreciates that 5-FU and 5-FU prodrugs are typically used in combination with other anti-cancer agents. For example, 5-FU or a 5-FU prodrug may be used in combination with folinic acid (also known as leucovorin), oxaliplatin (or other platinum-based drugs such as cisplatin) and/or irinotecan, e.g., 5-fluorouracil, leucovorin, and irinotecan. The method of treating cancer may further comprise administering one or more such agent(s) to the subject.

As used herein "treatment" or "treating", in reference to a subject, includes amelioration, cure, and/or maintenance of a cure (i.e., the prevention or delay of relapse and/or reducing the likelihood of recurrence) of a disorder (e.g., cancer). Treatment after a disorder has begun aims to reduce, ameliorate or altogether eliminate the disorder, and/or its associated symptoms, to prevent it from becoming worse, to slow the rate of progression, or to prevent the disorder from re-occurring once it has been initially eliminated (i.e., to prevent a relapse). Treating encompasses administration of an agent that may not have a beneficial effect on the disorder by itself but increases the efficacy of a second agent administered to the subject that has a beneficial effect on the disorder.

In some embodiments of any of the compositions and/or methods described herein that relate to an agent that increases uric acid levels, the agent that increases uric acid levels is uric acid itself. In some embodiments, the agent that lowers uric acid levels is a uricosuric agent, xanthine oxidase inhibitor, or uricase.

In some embodiments of any of the compositions and/or methods described herein that relate to a uric acid lowering agent, the uric acid lowering agent is a uricosuric agent. Uricosuric agents are substances that increase the excretion of uric acid in the urine, thereby reducing the concentration of uric acid in the blood. Such agents typically act on the proximal tubules in the kidneys, where they interfere with the absorption of uric acid from the urine back into the blood. In some embodiments, the uricosuric agent is a URAT1 inhibitor, i.e., a compound that inhibits urate transporter 1 (URAT1), a protein that is encoded by the gene SLC22A12 and normally functions in the transport of urate across the apical membrane of renal proximal tubules into tubular cells. URAT1 inhibitors include losartan, lesinurad (2-((5-bromo-4-(4-cyclopropylnaphthalen-1-yl)-4H-1,2,4-triazol-3-yl)thio) acetic acid) (Miner, J., et al., (2016) Arthritis Res Ther. 18(1):214), UR-1102 (Ahn, S O, et al., (2016) J Pharmacol Exp Ther. 357(1):157-66.), probenecid, and benzbromarone. In some embodiments, the uric acid lowering agent, e.g., URAT1 inhibitor, is a compound described in any of US Pat. Pub. Nos. 2013/0202573, 2014/0142185, 2015/0203490, 2015/0191463, 2015/0322006; 2016/0221970; and/or 2016/0250193.

In some embodiments of any of the compositions and/or methods described herein that relate to a uric acid lowering agent, the uric acid lowering agent comprises urate oxidase (UO), also referred to as uricase, an enzyme that catalyzes the oxidation of uric acid to 5-hydroxyisourate. Uricase can be purified from natural sources or produced recombinantly. Rasburicase (trade names Elitek® in the US and Fasturtec in Europe) is a recombinant version of urate oxidase produced by a genetically modified *Saccharomyces cerevisiae* strain. The cDNA coding for rasburicase was cloned from a strain of *Aspergillus flavus*. Rasburicase is a tetrameric protein with identical polypeptide subunits 301 amino acids long. One of ordinary skill in the art will appreciate that uricases from other organisms (e.g., other fungi, plants, non-human animals) could be used. The recommended dose for rasburicase for its approved indication, i.e., for the initial management of plasma uric acid levels in patients with leukemia, lymphoma, and solid tumor malignancies who are receiving anti-cancer therapy expected to result in tumor lysis and subsequent elevation of plasma uric acid is 0.20 mg/kg/day administered as an intravenous infusion daily for up to 5 days (Jena, 2010) but a shorter treatment period (e.g., single administration), lower dosage, or fixed dose(s) (e.g., 3 mg, 6 mg, 7.5 mg) have been found to be effective in a number of studies (see, e.g., Trifilio S M. (2006). The effectiveness of a single 3-mg rasburicase dose for the management of hyperuricemia in patients with hematological malignancies has been described in Bone Marrow Transplant. 37:997-1001; McBride A, et al. (2013) Comparative evaluation of single fixed dosing and weight-based dosing of rasburicase for tumor lysis syndrome has been described in Pharmacotherapy. 33(3):295-303). In some embodiments, the present disclosure contemplates administering uricase at doses between about 10 µg/kg and about 0.2 mg/kg. In some embodiments, the present disclosure contemplates administration of uricase to subjects who may not otherwise be candidates for its administration, e.g., subjects not expected to experience tumor lysis and elevation of plasma uric acid.

In some embodiments, a subject to whom a uric acid lowering agent is administered in combination with 5-FU or a 5-FU prodrug has a uric acid level above the normal range. In some embodiments, a subject to whom a uric acid lowering agent is administered in combination with 5-FU or a 5-FU prodrug has a uric acid level within the normal range. In some embodiments, a subject to whom a uric acid lowering agent is administered does not suffer from a disorder associated with an abnormally elevated uric acid level, such as gout. In some embodiments, the uric acid lowering agent is administered in an amount that reduces the subject's plasma uric acid level by between about 5% and about 95%, e.g., by at least about 5%, about 10%, about 20%, about 30%, about 40%, about 50%, about 60%, about 70%, about 80%, or about 90%. In some embodiments, the subject's uric acid level is reduced to below about 350 µM, e.g., to below about 300 µM, below about 200 µM, below about 150 µM, or below about 100 µM. In some embodiments, the plasma uric acid level may be a level measured about 24 hours after administration of the drug.

In some embodiments of any of the compositions and/or methods described herein that relate to a uric acid lowering agent, the uric acid lowering agent comprises a xanthine oxidase inhibitor. The term "xanthine oxidase inhibitor" refers to a substance that inhibits the activity of xanthine oxidase, an enzyme involved in purine metabolism. Inhibition of xanthine oxidase reduces the production of uric acid. In some embodiments, the xanthine oxidase inhibitor comprises febuxostat or topiroxostat. In some embodiments, the xanthine oxidase inhibitor comprises a thiadiazolopyrimidin-5-one (Sathisha K R, et al. (2016) Eur J Pharmacol. 776:99-105), an aryl-2H-pyrazole derivative (Sun Z G, et al. (2015) Chem Pharm Bull (Tokyo); 63(8):603-7), or a 2-amino-5-alkylidene-thiazol-4-one (Smelcerovic Z, et al. (2015) Chem Biol Interact. 2015; 229:73-81), a 2-(indol-5-yl)thiazole derivative (Song J U, et al. (2015) Bioorg Med Chem Lett. 25(6):1254-58), or a 1-hydroxy/methoxy-4-methyl-2-phenyl-1H-imidazole-5-carboxylic acid derivatives (Chen S, et al. (2015) Eur J Med Chem. 103:343-53). In preferred embodiments, the xanthine oxidase inhibitor does not inhibit UMPS. For example, in some embodiments, the xanthine oxidase inhibitor does not comprise a purine nucleotide that inhibits UMPS, such as allopurinol. In some embodiments, the xanthine oxidase inhibitor does not comprise oxypurinol or tisupurine. In some embodiments, the xanthine oxidase inhibitor does not comprise a purine nucleotide. In some embodiments, the uric acid lowering agent does not comprise a xanthine oxidase inhibitor.

An agent (e.g., 5-FU, a 5-FU prodrug, or a uric acid lowering agent) may be combined with a pharmaceutically acceptable carriers or vehicles, etc., to produce an appropriate pharmaceutical composition. The term "pharmaceutically acceptable carrier or vehicle" refers to a non-toxic carrier or vehicle that does not destroy the pharmacological activity of the compound with which it is formulated. One of skill in the art will understand that a carrier or vehicle is "non-toxic" if it is compatible with administration to a subject in an amount appropriate to deliver the compound without causing undue toxicity. Pharmaceutically acceptable carriers or vehicles that may be used include, but are not limited to, water, physiological saline, Ringer's solution, sodium acetate or potassium acetate solution, 5% dextrose, and the like. The composition may include other components as appropriate for the formulation desired.

A pharmaceutical composition can be administered to a subject by any suitable route of administration including, but not limited to, parenteral routes such as intravascular (intravenous, intra-arterial), intramuscular, subcutaneous, intracerebral, intrathecal, intranasal, and pulmonary, and enteral routes such as oral, sublingual, and rectal. In some embodiments, a systemic administration route may be used. In some embodiments, local administration to a tissue or organ affected by a disorder may be used. For example, in some embodiments intratumoral administration may be used.

A compound or composition, e.g., a pharmaceutical composition, can be used or administered to a subject in an effective amount. In some embodiments, an "effective amount" refers to an amount sufficient to elicit one or more biological response(s) of interest in, for example, a subject to whom the active agent (or composition) is administered. As will be appreciated by those of ordinary skill in the art, the absolute amount that is effective may vary depending on such factors as the biological endpoint, the particular active agent, the target tissue, etc. Those of ordinary skill in the art will further understand that an "effective amount" may be administered in a single dose, or may be achieved by administration of multiple doses. In some embodiments, an effective amount of a uric acid lowering agent is an amount sufficient to reduce a subject's blood uric acid level by at least about 10% or by at least about 30 µM. In some embodiments, an effective amount of a uric acid lowering agent may be an amount sufficient to improve the efficacy of 5-FU or a 5-FU prodrug in subjects with cancer. In certain embodiments, objective response of a subject with cancer e.g., as defined using the Response Evaluation Criteria In Solid Tumors (RECIST) guideline (Therasse, P., et al, Journal of the National Cancer Institute, 92(3): 205-216 (2000) or revised RECIST guideline (version 1.1) (Eisenhauer, E. A., et al, Eur J Cancer. 45(2):228-47 (2009)) or other accepted guidelines, e.g., for hematological cancers or brain tumors, may be used. For example, an outcome may be classified as a complete response, partial response, progressive disease, or stable disease.

In general, appropriate doses will depend at least in part upon the potency of the agent, route of administration, etc. In general, dose ranges that are effective and well tolerated can be selected by one of ordinary skill in the art. Such doses can be determined using clinical trials as known in the art. Optionally, a dose may be tailored to the particular recipient, for example, through administration of increasing doses until a predetermined desired response is achieved. If desired, the specific dose level for any particular subject may be selected based at least in part upon a variety of factors including the activity of the specific compound employed, the particular condition being treated and/or its severity, the age, body weight, general health, route of administration, any concurrent medication. In some embodiments, an effective amount or dose ranges from about 0.001 mg/kg to about 500 mg/kg body weight, e.g., about 0.01 to about 100 mg/kg body weight. Doses may be calculated based on body surface area rather than weight. In some embodiments, a fixed dose is used. In some embodiments, a fixed dose may, for example, range from about 0.1 mg to about 1 g of active agent.

One of ordinary skill in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a", "an", and "the" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure provides embodiments in which exactly one member of the group is present in, employed in, or otherwise relevant to a given product or process. The present disclosure also provides embodiments in which more than one, or all of the group members are present in, employed in, or otherwise relevant to a given product or process. Furthermore, it is to be understood that the present disclosure provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects described herein where appropriate. It is also contemplated that any of the embodiments or aspects or teachings can be freely combined with one or more other such embodiments or aspects whenever appropriate and regardless of where such embodiment(s), aspect(s), or teaching(s) appear in the present disclosure. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect can be explicitly excluded from the claims, regardless of whether the specific exclusion is recited in the specification. For example, any one or more components, agents, disorders, subjects, or combinations thereof, can be excluded.

Where the claims or description relate to a product (e.g., a composition of matter), it should be understood that methods of making or using the product according to any of the methods disclosed herein, and methods of using the product for any one or more of the purposes disclosed herein, are encompassed by the present disclosure, where applicable, unless otherwise indicated or unless it would be evident to one of ordinary skill in the art that a contradiction or inconsistency would arise. Where the claims or description relate to a method, it should be understood that product (s), e.g., compositions of matter, device(s), or system(s), useful for performing one or more steps of the method are encompassed by the present disclosure, where applicable, unless otherwise indicated or unless it would be evident to one of ordinary skill in the art that a contradiction or inconsistency would arise.

Where a series of numerical values is stated herein, embodiments that relate analogously to any intervening value or range defined by any two values in the series are provided, and that the lowest value may be taken as a minimum and the greatest value may be taken as a maximum. Where a phrase such as "at least", "up to", or similar phrases, precedes a series of numbers herein, it is to be understood that the phrase applies to each number in the list in various embodiments unless the context clearly dictates otherwise. For example, "at least 1, 2, or 3" should be understood to mean "at least 1, at least 2, or at least 3" in various embodiments. Any and all reasonable lower limits and upper limits are expressly contemplated where applicable. A reasonable lower or upper limit may be selected or determined by one of ordinary skill in the art based, e.g., on factors such as convenience, cost, time, effort, availability (e.g., of samples, agents, or reagents), statistical considerations, etc. In some embodiments, an upper or lower limit may differ by a factor of 2, 3, 5, or 10, from a particular value.

"Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). Thus, as used herein, "about" includes values that are up to 10% higher or 10% lower than the recited value. In certain embodiments, "about" indicates ±10%, ±9%, ±8%, ±7%, ±6%, ±5%, ±4%, ±3%, ±2%, ±1%, ±0.5%, or ±0.1% of the recited value. For each embodiment in which a numerical value is prefaced by "about" or "approximately", embodiments in which the exact value is recited are provided. For each embodiment in which a numerical value is not prefaced by "about" or "approximately", embodiments in which the value is prefaced by "about" or "approximately" are provided. Numerical values, as used herein, include numbers and also values expressed as percentages.

It should be understood that, unless clearly indicated to the contrary, in any methods claimed herein that include more than one act, the order of the acts of the method is not necessarily limited to the order in which the acts of the method are recited, but the invention includes embodiments in which the order is so limited. In some embodiments, a method may be performed by an individual or entity. In some embodiments, steps of a method may be performed by two or more individuals or entities such that a method is collectively performed. In some embodiments, a method may be performed at least in part by requesting or authorizing another individual or entity to perform one, more than one, or all steps of a method.

It should also be understood that unless otherwise indicated or evident from the context, any product or composition described herein may be considered "isolated".

Section headings used herein are not to be construed as limiting in any way. It is expressly contemplated that subject matter presented under any section heading may be applicable to any aspect or embodiment described herein.

Embodiments or aspects herein may be directed to any composition, article, kit, and/or method described herein. It is contemplated that any one or more embodiments or aspects can be freely combined with any one or more other embodiments or aspects whenever appropriate. It will be understood that any description or exemplification of a term anywhere herein may be applied wherever such term appears herein (e.g., in any aspect or embodiment in which such term is relevant) unless indicated or clearly evident otherwise.

All publications, patents, databases, and other references mentioned herein are hereby incorporated by reference in their entirety.

EXAMPLES

Figure 1A:
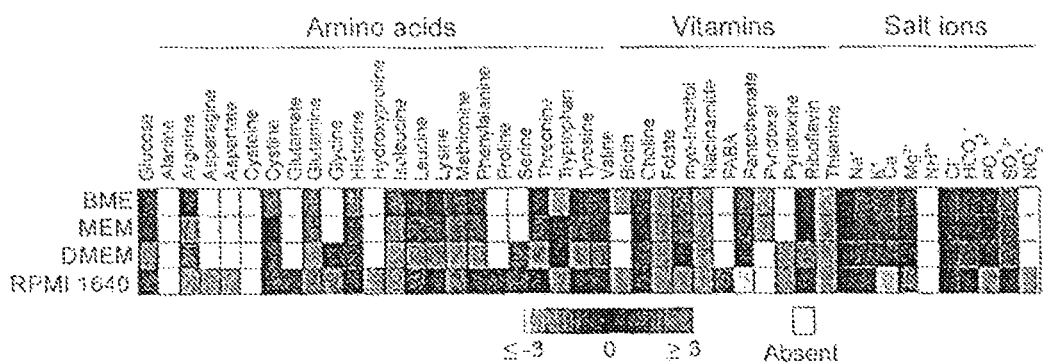
FIG. 1A depicts a heatmap of relative concentrations of the indicated components of BME, MEM, DMEM, and RPMI 1640 compared to those in adult human plasma (log 2-transformed fold changes). Components not present in a medium are marked as absent. See Table 4 for the concentrations of all metabolites in the various conventional media.
Figure 1B:
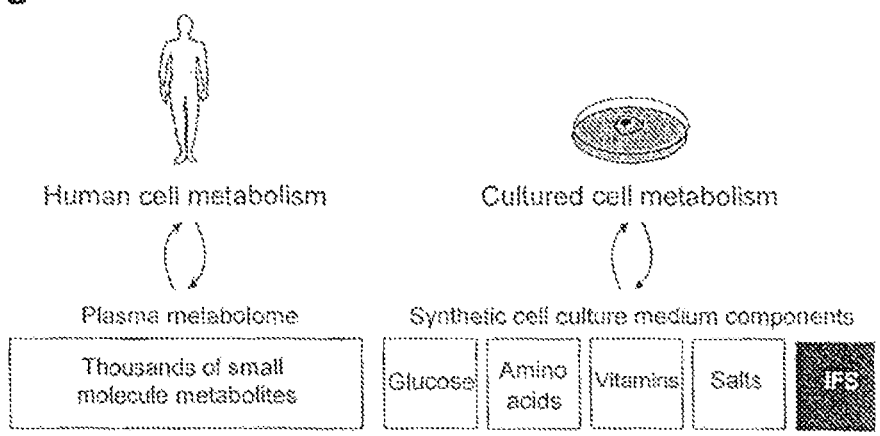
FIG. 1B is a schematic depicting the different metabolic milieus to which cells in culture and in vivo are exposed.

Example 1: A Cell Culture Medium that Reflects the Polar Metabolite Composition of Human Plasma Known synthetic cell culture media, BME, MEM, DMEM, and RPMI 1640, contain glucose, amino acids, vitamins, and salts at concentrations that in large part do not reflect those of human plasma (FIG. 1A). These media also lack additional components revealed to be present by mass spectrometric and NMR analyses of plasma (Psychogios et al., 2011). Instead, basal media are often supplemented with heat inactivated fetal bovine serum (IFS), which contributes an undefined and often unaccounted for cocktail of metabolites, as well as the growth factors and hormones needed for cell proliferation (Freshney, 2010). Thus, while the impact of environmental factors on cell metabolism is well appreciated (Davidson et al., 2016; DeNicola and Cantley, 2015; Hensley et al., 2016; Maddocks et al., 2013; Mayers et al., 2016; Pavlova and Thompson, 2016; Yuneva et al., 2012), the interrogation of cultured cells in media that better reflect the metabolite composition of human plasma is largely unexplored (FIG. 1B).

Figure 1C:
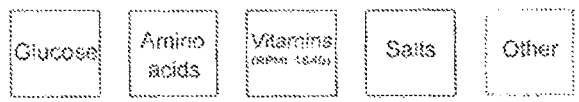
FIG. 1C depicts components of human plasma-like medium (HPLM). The concentrations of the components depicted by green-colored boxes reflect those in adult human plasma. The detailed formulation of HPLM is presented in Table 2.

Disclosed herein is a culture medium with a defined collection of metabolites and salt ions at concentrations reported for plasma from healthy adult humans (human plasma-like medium; HPLM) (Psychogios et al., 2011; Wishart et al., 2013). Although some serum-free media have entirely defined recipes, they often require meticulous tailoring of growth factors to support the culture of different cell types (Freshney, 2010). Thus, known growth media was supplemented with HPLM with 10% dialyzed IFS (HPLM$^+$$_{dIFS}$) to add the growth factors and hormones required for the proliferation of a broad range of cells, while minimizing the addition of polar metabolites at unknown concentrations. HPLM$^{+dIFS}$ is described in detail herein, but, in brief, it contains glucose, proteinogenic amino acids, salts, twenty-seven additional polar metabolites, 10% dialyzed IFS and vitamins at the same concentrations as RPMI 1640 (FIG. 1C, Table 2); uses a bicarbonate buffering system at physiological pH; and has an osmolality of ~295 mOsm/kg.

Figure 1D:
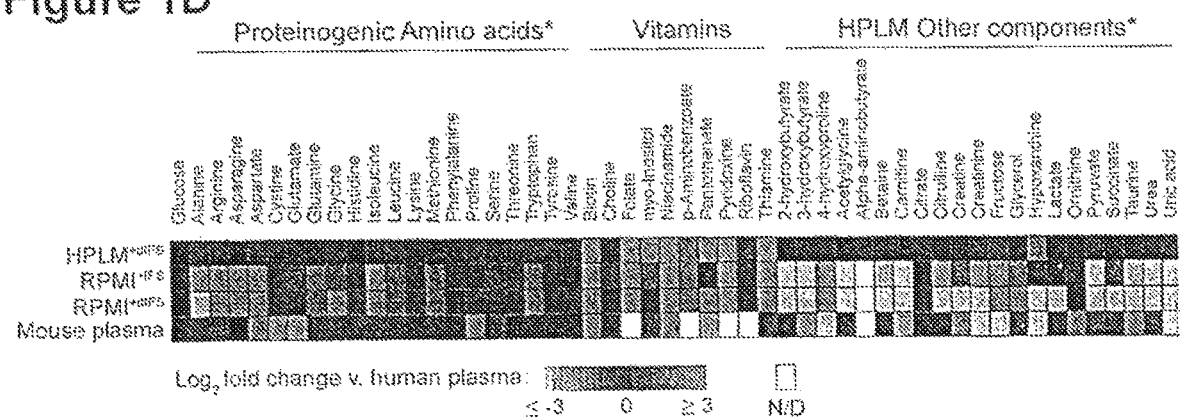
FIG. 1D depicts a heatmap of relative concentrations of the indicated components in denoted media and mouse plasma compared to those in human plasma (log 2-transformed fold changes). N/D, fold change value could not be determined. RPMI$^{+IFS}$: RPMI 1640 with 5 mM glucose and 10% IFS. RPMI$^{+dIFS}$: RPMI 1640 with 5 mM glucose and 10% dialyzed IFS. HPLM$^{+dIFS}$: HPLM containing 10% dialyzed IFS. *The following metabolites were not readily detected in media samples by the metabolite profiling method used: acetate, acetone, cysteine, formate, galactose, glutathione, and malonate.

Because RPMI 1640 (herein RPMI) is used for culturing normal blood cells as well as the hematological cancer cells (Freshney, 2010; Moore et al., 1967), this medium was used as a reference for comparing the effects of HPLM$^{+dIFS}$ on cells. Two RPMI formulations were used, each with physiological glucose (5 mM), but supplemented with either 10% IFS (RPMI$^{+IFS}$) or 10% dialyzed IFS (RPMI$^{+dIFS}$). Metabolite profiling confirmed that the dialysis of IFS substantially reduced its levels of polar metabolites (FIG. 1D, Tables 5A and 5B). Moreover, it also revealed that fetal bovine serum poorly reflects the metabolic composition of adult human plasma, as the addition of 10% IFS to RPMI did not yield concentrations for many metabolites at 10% of the reported values in human plasma. Similarly, while the concentrations of glucose and many amino acids in mouse plasma in large part resemble those in human plasma, those of other metabolites were very different, including examples that were at least 3-10-fold lower (e.g. carnitine and uric acid) or greater (e.g. 3-hydroxybutyrate and taurine) in mouse plasma (FIG. 1D). Thus, while murine tumor models are useful for studying metabolism in the context of stromal and immune cells, HPLM$^{+dIFS}$ more closely reflects the polar metabolite composition of human plasma than does mouse plasma.

TABLE 5A

Representative results of metabolite profiling of culture media

| Metabolite name | RPMI (+IFS)_avg | RPMI (+IFS)_sd | RPMI (+dIFS)_avg | RPMI (+dIFS)_sd | HPLM (+dIFS)_avg | HPLM (+dIFS)_sd |
|---|---|---|---|---|---|---|
| Glucose | 5240.622 | 899.152 | 4928.588 | 808.526 | 5110.053 | 548.542 |
| Alanine | 133.728 | 27.395 | 2.719 | 1.267 | 617.422 | 64.039 |
| Arginine | 902.633 | 62.126 | 811.598 | 120.868 | 100.104 | 18.251 |
| Asparagine | 333.800 | 8.160 | 319.944 | 23.353 | 48.566 | 3.062 |
| Aspartate | 134.254 | 31.571 | 118.045 | 22.878 | 16.710 | 2.918 |
| Cystine | 150.410 | 31.271 | 150.868 | 32.911 | 87.940 | 3.844 |
| Glutamate | 171.664 | 33.460 | 101.190 | 19.680 | 73.165 | 10.377 |
| Glutamine | 1903.354 | 136.857 | 1767.623 | 65.964 | 683.427 | 45.023 |
| Glycine | 179.886 | 36.987 | 108.043 | 16.418 | 331.976 | 13.665 |
| Histidine | 93.087 | 13.229 | 79.177 | 9.077 | 111.401 | 15.631 |
| Isoleucine | 404.828 | 56.492 | 367.061 | 48.474 | 77.898 | 3.082 |
| Leucine | 447.216 | 58.278 | 404.672 | 37.005 | 188.007 | 8.107 |
| Lysine | 190.227 | 21.888 | 171.887 | 26.119 | 205.678 | 26.898 |
| Methionine | 99.165 | 14.223 | 91.735 | 10.964 | 31.590 | 2.195 |
| Phenylalanine | 98.871 | 11.532 | 81.825 | 9.361 | 87.817 | 9.264 |
| Proline | 192.639 | 21.890 | 159.524 | 13.996 | 234.709 | 9.899 |
| Serine | 257.243 | 37.825 | 224.096 | 31.112 | 136.072 | 9.206 |
| Threonine | 185.495 | 25.544 | 161.455 | 18.305 | 178.400 | 9.876 |

TABLE 5A-continued

Representative results of metabolite profiling of culture media

| Metabolite name | RPMI (+IFS)_avg | RPMI (+IFS)_sd | RPMI (+dIFS)_avg | RPMI (+dIFS)_sd | HPLM (+dIFS)_avg | HPLM (+dIFS)_sd |
|---|---|---|---|---|---|---|
| Tryptophan | 29.035 | 5.092 | 24.828 | 4.108 | 66.081 | 3.264 |
| Tyrosine | 125.517 | 22.392 | 114.026 | 19.658 | 100.180 | 11.815 |
| Valine | 198.351 | 43.947 | 163.309 | 28.634 | 263.340 | 36.908 |
| Biotin | 0.616 | 0.072 | 0.608 | 0.078 | 0.053 | 0.010 |
| Choline | 20.863 | 4.012 | 11.553 | 1.920 | 14.772 | 0.740 |
| Folate | 3.708 | 0.969 | 3.925 | 0.859 | 2.223 | 1.121 |
| myo-Inositol | 75.268 | 13.886 | 28.747 | 6.293 | 172.196 | 20.415 |
| Niacinamide | 7.068 | 0.704 | 5.871 | 0.719 | 7.788 | 0.983 |
| p-Aminobenzoate | 6.443 | 0.932 | 6.070 | 1.031 | 6.504 | 1.201 |
| Pantothenate | 5.886 | 2.313 | 1.340 | 0.461 | 1.387 | 0.351 |
| Pyridoxine | 3.684 | 0.844 | 3.575 | 0.973 | 3.899 | 1.470 |
| Riboflavin | 0.436 | 0.157 | 0.400 | 0.181 | 0.457 | 0.157 |
| Thiamine | 1.496 | 0.211 | 1.272 | 0.251 | 2.009 | 0.153 |
| 2-hydroxybutyrate | 1.912 | 0.353 | N/D | | 49.112 | 5.176 |
| 3-hydroxybutyrate | 6.455 | 1.306 | N/D | | 52.832 | 11.890 |
| 4-hydroxyproline | 153.177 | 21.960 | 133.999 | 16.897 | 21.966 | 1.795 |
| Acetylglycine | N/D | | N/D | | 90.432 | 22.272 |
| Alpha-aminobutyrate | N/D | | N/D | | 23.464 | 4.255 |
| Betaine | 10.909 | 2.128 | N/D | | 68.128 | 14.406 |
| Carnitine | 1.220 | 0.116 | 0.077 | 0.018 | 42.896 | 4.360 |
| Citrate | 125.602 | 67.025 | 87.637 | 24.997 | 149.562 | 41.928 |
| Citrulline | 8.392 | 1.007 | 0.469 | 0.073 | 39.924 | 3.272 |
| Creatine | 19.783 | 2.467 | 0.218 | 0.016 | 38.822 | 4.969 |
| Creatinine | 20.427 | 1.986 | 0.470 | 0.314 | 101.219 | 11.848 |
| Fructose | 625.213 | 202.548 | 12.278 | 4.229 | 30.378 | 9.120 |
| Glycerol* | 28.895 | 10.954 | 22.666 | 0.569 | 66.203 | 15.600 |
| Hypoxanthine | 7.645 | 0.809 | N/D | | 4.099 | 0.827 |
| Lactate | 1511.917 | 453.846 | 10.662 | 3.823 | 1523.746 | 276.059 |
| Ornithine | 56.617 | 10.043 | 78.645 | 7.100 | 71.601 | 5.931 |
| Pyruvate | 2.710 | 0.414 | N/D | | 42.578 | 13.265 |
| Succinate | 60.326 | 12.162 | 2.365 | 1.059 | 19.386 | 3.381 |
| Taurine | 13.831 | 4.274 | N/D | | 95.150 | 13.013 |
| Urea* | 1.155 | 0.690 | 0.162 | 0.016 | 12.014 | 1.284 |
| Uric acid | 7.814 | 2.436 | N/D | | 340.055 | 19.220 |

*Values indicate normalized peak areas rather than µM; for heatmap, fold change values were calculated in comparison to HPLM
All concentrations in Tables 5A and 5B are in micromolar unless otherwise indicated.
Mean and standard deviation values in Tables 5A and 5B are calculated from 4 biological replicates.
N/D: not detected.

In Table 5A, for those metabolites whose concentrations are listed as N/D, the concentration corresponding to that of minimum detection in media samples was used for the heatmap in FIG. 1D, except in the case of alpha-aminobutyrate. These values are as follows: 2-hydroxybutyrate: 0.4 µM; 3-hydroxybutyrate: 2 µM; acetylglycine: 4 µM; betaine: 0.5 µM; hypoxanthine: 0.02 µM; pyruvate: 2 µM; taurine: 4 µM; uric acid: 0.5 µM. The concentration of minimum detection of alpha-aminobutyrate (20 uM) was such that its assignment for RPMI would result in fold change values that fall within the scale limits of the heatmap. Therefore, the comparison was excluded from the heatmap to avoid confounding interpretation. It should be noted that acetate, acetone, cysteine, formate, galactose, glutathione, and malonate are defined components of HPLM but could not be readily detected by the metabolite profiling method used for media samples in this experiment.

Additional metabolites were detected and quantified in media formulations containing IFS or dIFS as shown in Table 5B. These compounds are not defined components of HPLM (or of RMPI) but are presumably contributed by the IFS/dIFS and are therefore not included in the heatmap of FIG. 1D.

TABLE 5B

Representative results of metabolite profiling of culture media

| Metabolite name | RPMI (+IFS)_avg | RPMI (+IFS)_sd | RPMI (+dIFS)_avg | RPMI (+dIFS)_sd | HPLM (+dIFS)_avg | HPLM (+dIFS)_sd |
|---|---|---|---|---|---|---|
| 2-hydroxyglutarate | 1.497 | 0.588 | N/D | | N/D | |
| Acetylaspartate | 0.300 | 0.049 | N/D | | N/D | |
| Acetylcarnitine | 0.555 | 0.044 | N/D | | N/D | |
| Acetylserine | 0.385 | 0.121 | N/D | | N/D | |
| Aconitate | 0.329 | 0.047 | 0.153 | 0.037 | 0.119 | 0.045 |
| Allantoin | 15.618 | 3.782 | 0.301 | 0.076 | 2.387 | 1.683 |
| Aminoadipate | 2.039 | 0.294 | N/D | | N/D | |
| Argininosuccinate | 3.807 | 1.116 | N/D | | N/D | |
| Asymmetric dimethylarginine | 0.884 | 0.298 | 0.098 | 0.003 | 0.093 | 0.013 |

TABLE 5B-continued

Representative results of metabolite profiling of culture media

| Metabolite name | RPMI (+IFS)_avg | RPMI (+IFS)_sd | RPMI (+dIFS)_avg | RPMI (+dIFS)_sd | HPLM (+dIFS)_avg | HPLM (+dIFS)_sd |
| --- | --- | --- | --- | --- | --- | --- |
| beta-Alanine | 3.637 | 1.178 | N/D | | N/D | |
| Carnosine | 1.471 | 0.260 | 0.127 | 0.047 | 0.077 | 0.015 |
| Cytidine | 1.057 | 0.117 | N/D | | N/D | |
| Deoxycytidine | 0.214 | 0.025 | N/D | | N/D | |
| Fumarate | 6.785 | 1.138 | N/D | | N/D | |
| Kynurenine | 0.505 | 0.092 | 0.286 | 0.059 | 0.241 | 0.039 |
| Malate | 16.217 | 1.947 | 1.603 | 0.426 | 1.282 | 0.507 |
| Methionine sulfoxide | 1.682 | 0.224 | 1.328 | 0.077 | 0.703 | 0.096 |
| Pseudouridine | 0.878 | 0.092 | 0.046 | 0.018 | 0.042 | 0.016 |
| Ribitol | 1.344 | 0.577 | N/D | | N/D | |
| Sorbitol | 78.436 | 17.144 | 1.474 | 0.245 | 1.359 | 0.391 |
| Thymidine | 0.384 | 0.032 | N/D | | N/D | |
| Trimethyllysine | 1.290 | 0.286 | 0.097 | 0.020 | 0.095 | 0.020 |
| Uracil | 3.659 | 0.314 | N/D | | N/D | |
| Uridine | 1.998 | 0.219 | N/D | | N/D | |
| Xanthine | 5.597 | 1.523 | 0.109 | 0.086 | 0.367 | 0.025 |
| Xanthosine | 0.244 | 0.074 | N/D | | N/D | |

HPLM$^{+dIFS}$ provides the metabolites needed for cancer cell proliferation, as six cell lines, representing various human hematological cancers, proliferated in HPLM$^{+dIFS}$ at rates that were comparable, albeit generally lower, to those in RPMI$^{+IFS}$ and RPMI$^{+dIFS}$ (FIG. 1E).

Figure 2A:
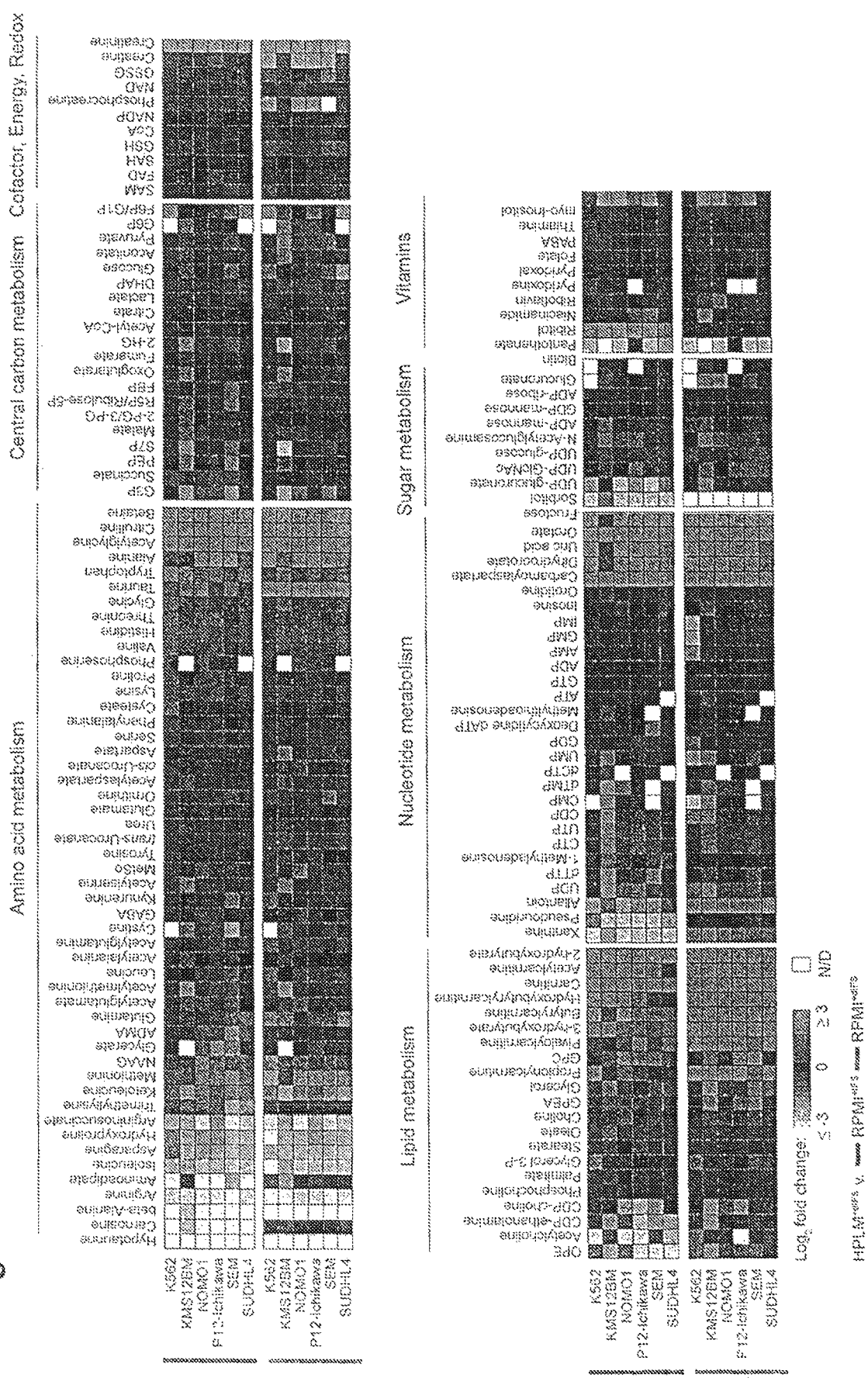
FIG. 2A depicts a heatmap of relative intracellular metabolite concentrations following culture in HPLM$^{+dIFS}$ compared to that in RPMI$^{+IFS}$ (top six rows) or to RPMI$^{+dIFS}$ (bottom six rows). Within each group, metabolites are sorted by average loge-transformed fold change of the top six rows (n=3). N/D, fold change value could not be determined because the metabolite was not readily detected following culture in one or more of the media. To be included in the heatmap, metabolites had to have a fold change measured in at least four of the six cell lines. See Table 6 for metabolite abbreviations.

Example 2: Culture of Cells in HPLM Extensively Alters their Metabolic Landscape and Fate of Glucose Carbons To test the hypothesis that culturing cells in a medium that better mimics the metabolic composition of human plasma alters cellular metabolism compared to that in established media, the metabolite profiles of cells cultured in HPLM$^{+}$$_{dIFS}$ were compared to those in RPMI$^{+IFS}$ or RPMI$^{+dIFS}$. Indeed, HPLM$^{+dIFS}$ significantly affected the intracellular abundances of many metabolites across multiple pathways, including amino acid, lipid, and nucleotide metabolism (FIG. 2A; see Table 6 for abbreviations).

TABLE 6

Certain metabolite abbreviations

| Full metabolite name | Abbreviation used in heatmap |
| --- | --- |
| 2-hydroxyglutaric acid | 2-HG |
| 2-phosphoglycerate/3-phosphoglycerate | 2-PG/3-PG |
| Asymmetric dimethylarginine | ADMA |
| Coenzyme A | CoA |
| Dihydroxyacetone phosphate | DHAP |
| Fructose 6-phosphate/Glucose 1-phosphate | F6P/G1P |
| Fructose-1,6-bisphosphate | FBP |
| Glyceraldehyde 3-phosphate | G3P |
| Glucose 6-phosphate | G6P |
| Gamma-aminobutyric acid | GABA |
| Glycerophosphocholine | GPC |
| Glycerophosphoethanolamine | GPEA |
| Glutathione | GSH |
| Glutathione disulfide | GSSG |
| Methionine sulfoxide | Met-so |
| N-acetylaspartylglutamic acid | NAAG |
| O-phosphoethanolamine | OPE |
| p-Aminobenzoic acid | PABA |
| Phosphoenolpyruvate | PEP |
| Ribose 5-phosphate/Ribulose 5-phosphate | R5P/Ribulose 5-P |
| Sedoheptulose 7-phosphate | S7P |

For several metabolites, such as arginine, asparagine, and taurine, the differences reflected those in the media themselves, while for others, such as aspartate and lactate, they did not. Most HPLM$^{+dIFS}$-induced changes were shared by all six of the cell lines examined, but some were cell line-specific, underscoring how the heterogeneity of cancer (Cantor and Sabatini, 2012; Davidson et al., 2016; Eason and Sadanandam, 2016; Hensley et al., 2016; Hu et al., 2013; Mayers et al., 2016; Shaul et al., 2016; Yuneva et al., 2012) can influence the cellular responses to environmental conditions. For example, whereas HPLM$^{+dIFS}$ reduced argininosuccinate abundance in five cell lines, it increased it in P12-Ichikawa cells. Similarly, HPLM$^{+dIFS}$ caused dramatic elevations in fructose-6-phosphate/glucose-1-phosphate (F6P/G1P) only in K562, P12-Ichikawa, and SUDHL4 cells, and modest reductions in oxoglutarate only in KMS12BM cells.

Figures 2B, 2C, 2D:
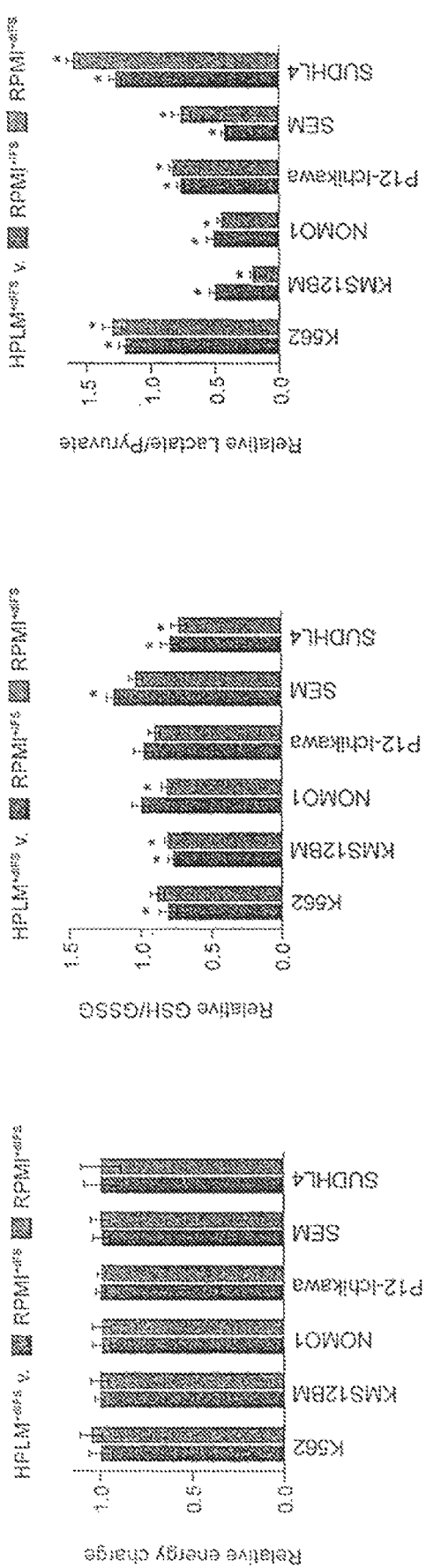
FIG. 2B depicts energy charge values, as calculated by the displayed equation, following culture in HPLM$^{+dIFS}$ compared to that in RPMI$^{+IFS}$ (blue) or to RPMI$^{+dIFS}$ (red) (mean±SD, n=3).
FIG. 2C depicts intracellular GSH/GSSG ratios following culture in HPLM$^{+dIFS}$ compared to that in RPMI$^{+IFS}$ (blue) or to RPMI$^{+dIFS}$ (red) (mean±SD, n=3, *p<0.05).
FIG. 2D depicts intracellular lactate/pyruvate ratios following culture in HPLM$^{+dIFS}$ compared to that in RPMI$^{+IFS}$ (blue) or to RPMI$^{+dIFS}$ (red) (mean±SD, n=3, *p<0.05).

Culture in HPLM$^{+dIFS}$ did not affect the energy charge (Atkinson, 1968) in any cell line (FIG. 2B), but did have cell line-specific effects on the redox state as reflected by changes to the ratios of two redox couples: GSH/GSSG (FIG. 2C) and NADH/NAD$^{+}$, as estimated by lactate/pyruvate (Ido et al., 2004; Williamson et al., 1967; Zhang et al., 2002) (FIG. 2D).

Lastly, HPLM$^{+dIFS}$ did not significantly alter the correlation between glucose consumption and lactate secretion rates (FIG. 8), suggesting that it had little effect on the aerobic glycolysis phenotype common to most cancer cells (Hosios et al., 2016; Jain et al., 2012).

Figure 3B:
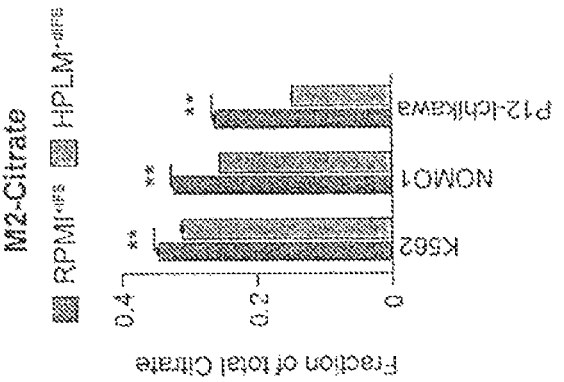
FIG. 3B depicts the fraction of pyruvate labeled with three $^{13}$C (M3) following culture of cells in RPMI$^{+IFS}$ (dark gray) or HPLM$^{+IFS}$ (green) (mean±SD, n=3) (left). Concentrations of pyruvate in RPMI$^{+IFS}$ and HPLM$^{+dIFS}$ as measured by LC/MS-based metabolite profiling (n=4) (right).
Figure 3C:
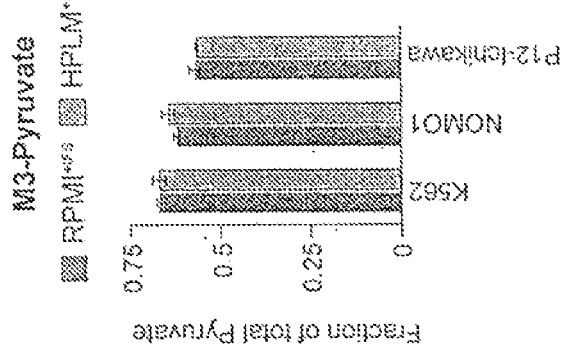
FIG. 3C depicts the fraction of citrate labeled with two $^{13}$C (M2) following culture of cells in RPMI$^{+IFS}$ (dark gray) or HPLM$^{+IFS}$ (green) (mean±SD, n=3; *p<0.0001).

To specifically study glucose utilization, the $^{13}$C-labeling patterns for several metabolites were compared following the culture of three cell lines (K562, NOMO1, and P12-Ichikawa) in HPLM$^{+dIFS}$ containing [U-$^{13}$C]-glucose to those in RPMI$^{+IFS}$ or RPMI$^{+dIFS}$ (FIG. 3A). Interestingly, while HPLM$^{+dIFS}$ contains pyruvate at a concentration of ~40 µM, which is over 10-fold greater than that of RPMI$^{+}$$_{IFS}$, it did not affect the fraction of pyruvate labeled with three $^{13}$C (M3) (FIG. 3B). However, HPLM$^{+dIFS}$ did affect the metabolism of glucose-derived Acetyl-CoA generated by the oxidation of pyruvate, as reflected by reductions in the M2 labeling of citrate in the TCA cycle (FIG. 3C).

As with the metabolome, HPLM$^{+dIFS}$ also had cell-line dependent effects on glucose utilization. Among the most prominent was a significant reduction in the M6 labeling of F6P/G1P only in K562 and P12-Ichikawa cells (FIG. 3D), suggesting that sources beyond exogenous glucose contribute to F6P/G1P pools when these cells are cultured in HPLM$^{+dIFS}$. In addition, although HPLM$^{+dIFS}$ contains alanine at ~620 μM, a concentration nearly 5-fold greater than that of RPMI$^{+IFS}$, it did not affect the fraction of M3-alanine in two cell lines. However, it reduced by over 2-fold the M3 labeling of alanine in P12-Ichikawa cells (FIG. 3E), revealing that HPLM$^{+dIFS}$ impacts the fate of glucose-derived pyruvate in these cells. Finally, HPLM$^{+dIFS}$ also decreased the M3 labeling of glycerophosphocholine only in K562 and P12-Ichikawa cells, suggesting that HPLM$^{+dIFS}$ induces cell-line specific alterations to glucose utilization for lipid synthesis (FIG. 3F). Nearly all these changes were also observed when comparing cells cultured in HPLM$^{+dIFS}$ to those in RPMI$^{+dIFS}$, though greater discrepancies in the levels of certain exogenous metabolites, such as pyruvate and alanine, influenced their corresponding $^{13}$C labeling patterns.

Collectively, these data reveal that while aerobic glycolysis was essentially unaffected, culture in HPLM$^{+dIFS}$, compared to that in RPMI, had widespread effects on the metabolic landscape of cells. These include extensive alterations to the metabolome, redox state, and glucose utilization, and were either common to all cell lines tested or were cell line-specific.

Figure 4E:
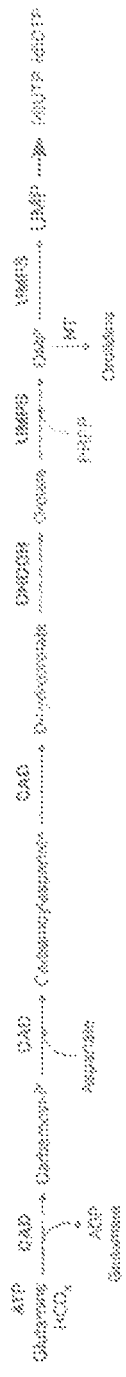
FIG. 4E is a schematic depicting the de novo pyrimidine synthesis pathway. NT: nucleotidase. Relative intracellular abundances of CTP (FIG. 4F) and UTP (FIG. 4G) following culture of cells in HPLM$^{+dIFS}$ compared to that in RPMI$^{+IFS}$ (blue) or RPMI$^{+dIFS}$ (red) (mean±SD, n=3, *p<0.05).
Figure 4G:
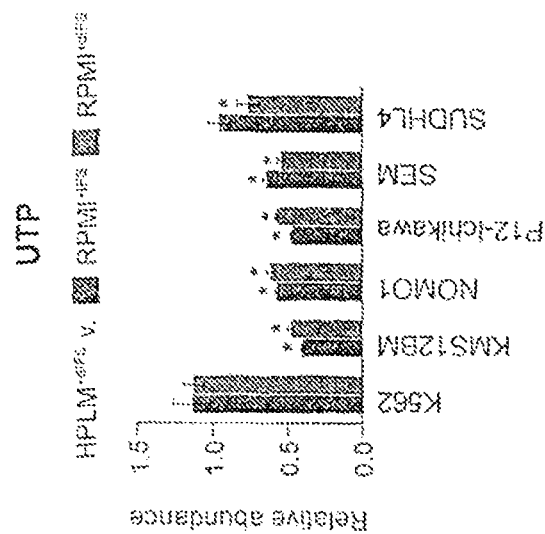
Figure 4F:
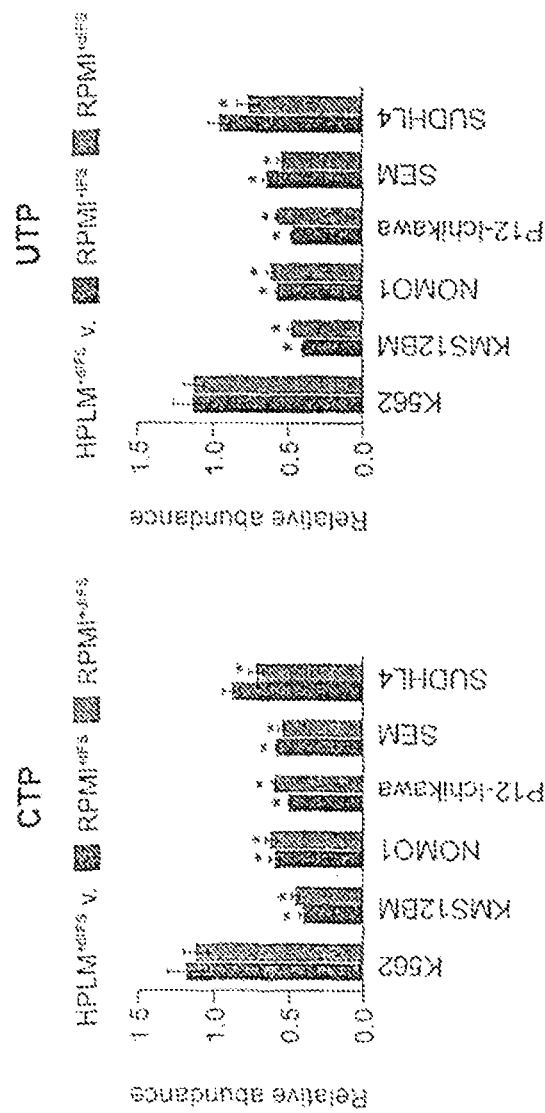

Example 3: The Uric Acid Component of HPLM has Striking Effects on De Novo Pyrimidine Biosynthesis Among the most significant consequences of culture in HPLM$^{+dIFS}$ compared to that in RPMI were increases in the intracellular abundances of four metabolites involved in nucleotide metabolism: carbamoylaspartate, dihydroorotate, orotate, and orotidine (FIGS. 4A-D). None of the four could be detected in either medium. The first three are intermediates in the de novo pyrimidine biosynthesis pathway that generates UMP, while orotidine is the dephosphorylation product of OMP, which is the immediate precursor to UMP in this pathway (FIG. 4E). In four of the six cell lines examined, culture in HPLM$^{+dIFS}$ also reduced by 40-60% the intracellular levels of the UTP and CTP pyrimidine nucleotides (FIGS. 4F-G), but did not have similar effects on purine nucleotides (FIG. 9). While not wishing to be bound by any theory, cell line-dependent contributions of salvage pathway activities (Evans and Guy, 2004) or altered consumption of pyrimidine nucleotide pools may explain why HPLM$^{+dIFS}$ does not decrease the abundance of pyrimidine nucleotides in all cells.

Figure 5A:
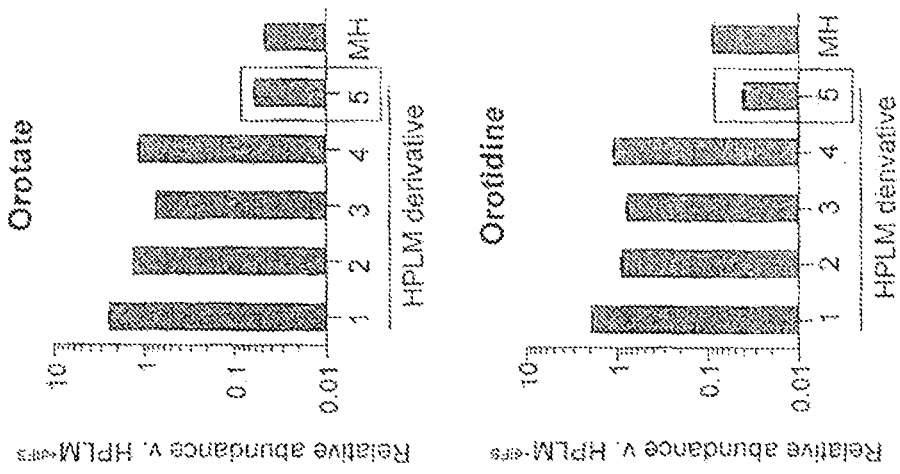
FIG. 5A depicts the composition of minimal HPLM (top) and list of components removed from HPLM$^{+dIFS}$ to generate the indicated dropout formulations (bottom).
Figure 5B:
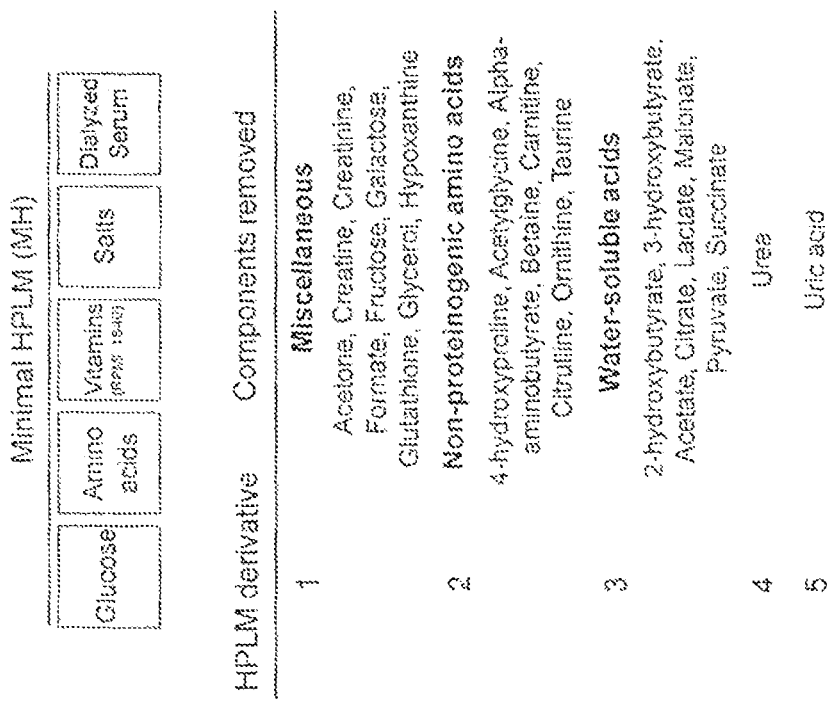
FIG. 5B depicts the relative intracellular abundances of orotate (top) and orotidine (bottom) following culture of cells in each HPLM$^{+dIFS}$ derivative or minimal HPLM (MR) compared to that in complete HPLM$^{+dIFS}$ (mean±SD, n=3). The number designations of the HPLM$^{+dIFS}$ derivatives correspond to those in panel A.
Figures 5C, 5D:
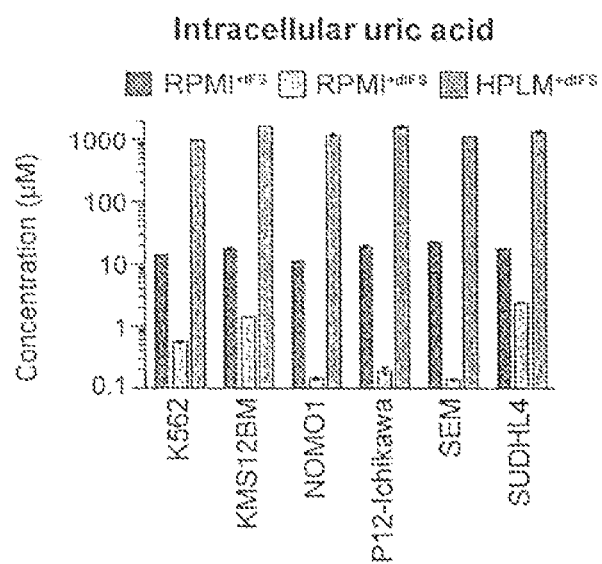
FIG. 5C depicts the concentrations of uric acid in RPMI$^{+IFS}$ and HPLM$^{+dIFS}$ as measured by LC/MS-based metabolite profiling (n=4). Uric acid could not be readily detected in RPMI$^{+dIFS}$ by the metabolite profiling method used. Thus, the indicated concentration for RPMI$^{+}_{dIFS}$ approximately corresponds to that of minimum detection in media samples.
FIG. 5D depicts the intracellular concentrations of uric acid following culture of cells in RPMI$^{+IFS}$, RPMI$^{+dIFS}$, or HPLM$^{+dIFS}$ (mean±SD, n=3).
Figure 5F:
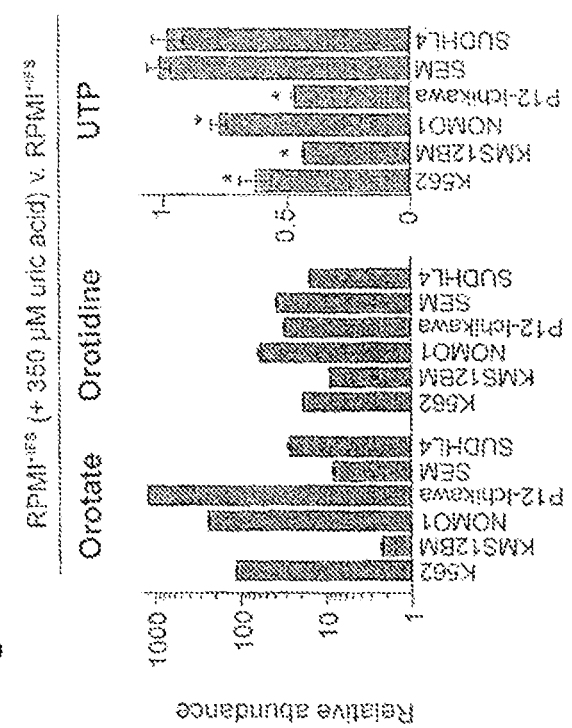
FIG. 5F depicts the relative intracellular abundances of orotate, orotidine (left) (mean±SD, n=3; p<0.0001 for all bars), and UTP (mean±SD, n=3; *p<0.05) (right) following culture of cells in RPMI$^{+IFS}$ supplemented with 350 µM uric acid compared to that in RPMI$^{+IFS}$.
Figure 5E:
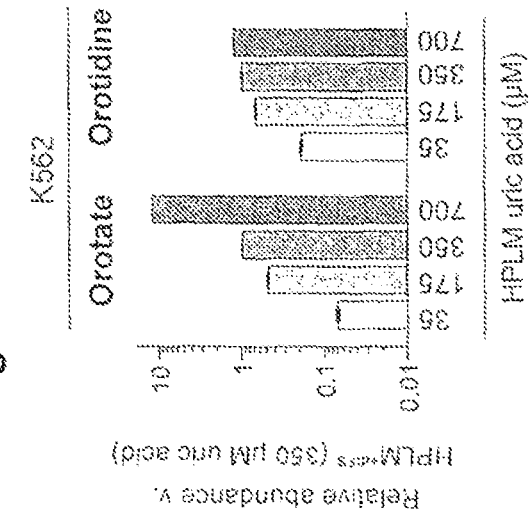
FIG. 5E depicts the relative intracellular abundances of orotate and orotidine following culture of K562 cells in HPLM$^{+dIFS}$ containing increasing concentrations of uric acid compared to that in standard HPLM$^{+dIFS}$, which contains 350 µM uric acid (mean±SD, n=3).
Figure 5G:
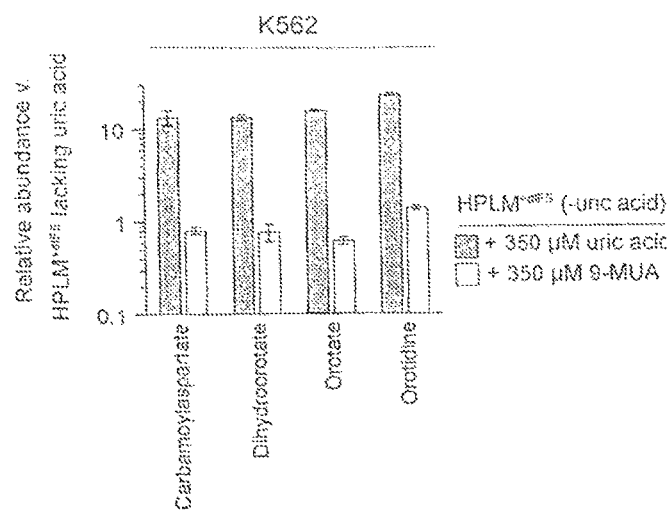
FIG. 5G depicts the relative intracellular abundances of carbamoylaspartate, dihydroorotate, orotate, and orotidine following culture of K562 cells in HPLM$^{+dIFS}$ containing either 350 µM uric acid (green) or 350 µM uric acid 9-methyluric acid (9-MUA) (white) compared to that in HPLM$^{+dIFS}$ lacking uric acid (mean±SD, n=3).

To determine which component(s) of HPLM$^{+dIFS}$ affects the de novo pyrimidine synthesis pathway, K562 cells were cultured in HPLM$^{+dIFS}$ derivatives lacking: (1) acetone, creatine, creatinine, formate, fructose, galactose, glutathione, glycerol, and hypoxanthine; (2) non-proteinogenic amino acids (8 metabolites); (3) water-soluble acids (8 metabolites); (4) urea; or (5) uric acid (FIG. 5A). Remarkably, uric acid alone mediated the observed effects, as its removal from HPLM$^{+dIFS}$ reduced orotate and orotidine levels to those of cells cultured in RPMI (FIG. 3C-D) or in minimal HPLM, which lacks the twenty-seven components collectively missing from the dropout formulations (FIG. 5B). HPLM$^{+dIFS}$ contains uric acid at 350 mM, a concentration that is 40- and at least 500-fold greater than that of RPMI$^{+IFS}$ and RPMI$^{+dIFS}$, respectively (FIG. 5C), and, importantly, its intracellular concentration reflects that of the corresponding culture medium (FIG. 5D). In K562 cells, uric acid dose-dependently increased orotate and orotidine abundances (FIG. 5E), and at its highest tested concentration (700 μM), led to a detectable accumulation of OMP. The addition of 350 μM uric acid to RPMI$^{+IFS}$ also greatly boosted orotate and orotidine levels, but, like complete HPLM, had cell line-dependent effects on UTP abundance (FIG. 5F). Lastly, the closely related molecule 9-methyluric acid (9-MUA) entered K562 cells but did not alter the levels of orotate, orotidine, or the other intermediates in the de novo pyrimidine biosynthesis pathway (FIG. 5G).

Figure 5H:
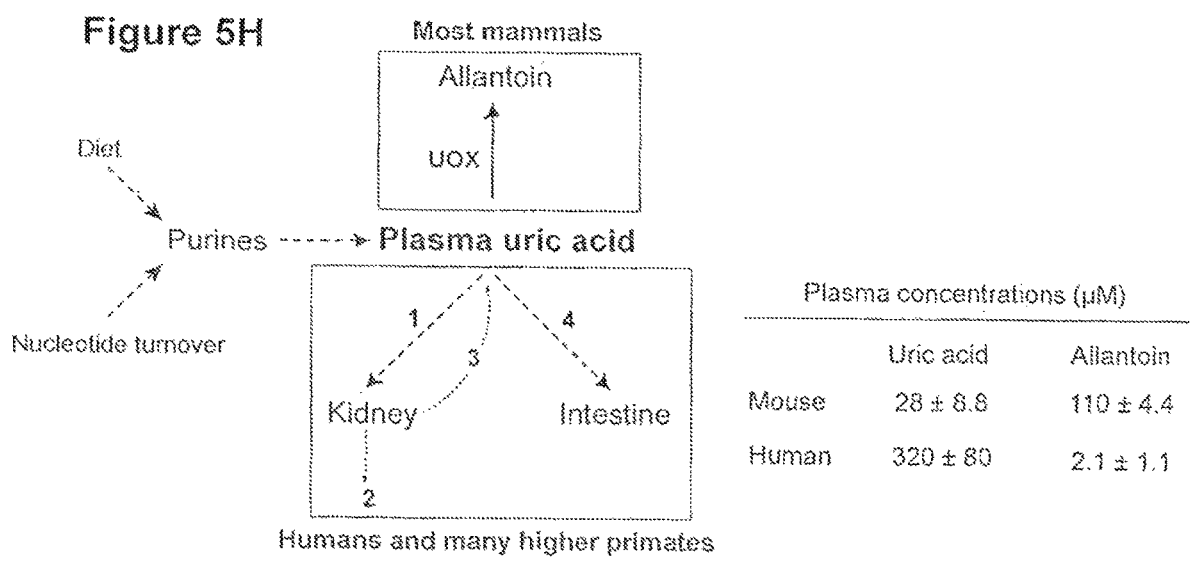
FIG. 5H is a schematic depicting the pathways that influence the plasma concentrations of uric acid; 1: glomerular filtration (70%), 2: secretion (10%), 3: reabsorption (90%), 4: excretion (30%) (Bobulescu and Moe, 2012). In contrast to most mammals, humans and many higher primates lack uricase (UOX) activity, which converts uric acid to allantoin (left). Concentrations of uric acid and allantoin in mouse plasma as measured by LC/MS metabolite profiling (n=4). Average concentration of uric acid in human plasma calculated from annotated values in the Human Metabolome Database. Concentration of allantoin in human plasma as reported elsewhere (Kand'ár and Záková, 2008) (right).

The effects of uric acid on pyrimidine metabolism show an increase in plasma concentrations up to an order of magnitude greater in humans, chimpanzees, gorillas, and additional higher primates than in other mammals (Álvarez-Lario and Macarrón-Vicente, 2010; Kratzer et al., 2014; Wu et al., 1992). Whereas most mammalian species, including mouse and cow, metabolize uric acid to allantoin via the liver enzyme uricase, the gene encoding uricase (UOX) became inactivated via pseudogenization during hominid evolution (Kratzer et al., 2014; Oda et al., 2002; Wu et al., 1992; 1989). As a consequence, uric acid, rather than allantoin, is the end product of purine catabolism in many higher primates (FIG. 5H). Furthermore, in mice, which have a plasma uric acid concentration of ~30 μM, uricase activity is essential, given that most UOX-null mice die within four weeks of life from extreme hyperuricemia and nephropathy (Wu et al., 1994). Thus, the finding that uric acid impacts the de novo pyrimidine biosynthesis pathway would have been difficult to make by studying cells growing in mice or cultured in conventional media.

Example 4: Uric Acid is a Direct Inhibitor of UMPS

Figure 6A:
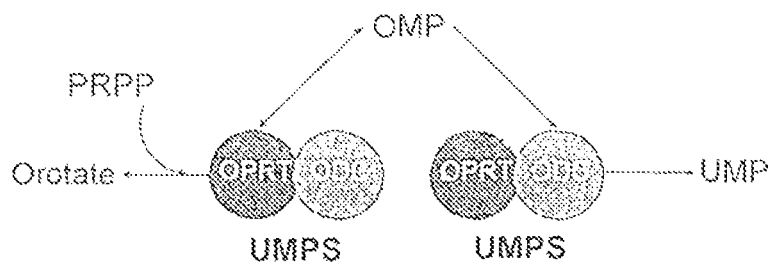
FIG. 6A is a schematic depicting the reactions catalyzed by each domain of bifunctional UMP synthase (UMPS). OPRT: orotate phosphoribosyltransferase. ODC: OMP decarboxylase.

In addition to boosting the intracellular levels of orotate and orotidine, HPLM also markedly increased their secretion into the media (FIG. 10)—a phenomenon reminiscent of the high urinary excretion of these metabolites in patients with orotic aciduria and orotidinuria. As this disorder can be caused by the genetic (Bailey, 2009; Fox et al., 1973; Smith et al., 1961; Suchi et al., 1997) or pharmacological (Bono et al., 1964; Fallon et al., 1961; Fox et al., 1970; Kelley and Beardmore, 1970) inhibition of UMP synthase (UMPS), the uric acid component of HPLM may lead to the inhibition of this enzyme in cells. UMPS is a bifunctional two-domain enzyme that catalyzes the final two steps of the de novo pyrimidine biosynthesis pathway to generate UMP (Jones, 1980). In the first step, the orotate phosphoribosyltransferase (OPRT) domain synthesizes OMP from orotate and PRPP, and in the second, the OMP decarboxylase (ODC) domain converts OMP to UMP (FIG. 6A).

Figure 6B:
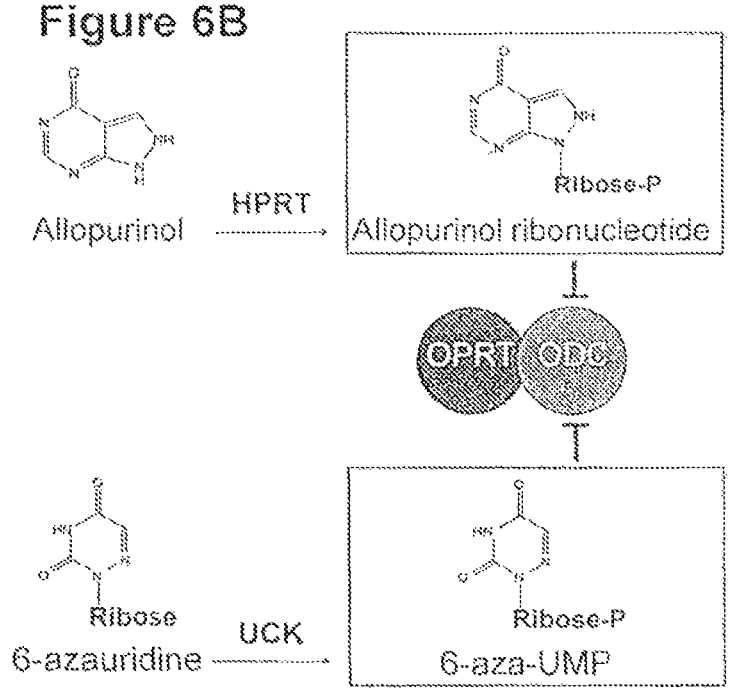
FIG. 6B is a schematic depicting competitive inhibition of the ODC domain of UMPS by allopurinol ribonucleotide (top) and 6-aza-UMP (bottom). Hypoxanthine-guanine phosphoribosyltransferase (HPRT) catalyzes the conversion of allopurinol to its ribonucleotide derivative, and uridine-cytidine kinase (UCK) catalyzes that of 6-azauridine to 6-aza-UMP.

To determine whether uric acid might cause inhibition of UMPS, an established UMPS inhibitor was studied to see if it had similar effects on the de novo pyrimidine biosynthesis pathway as uric acid in disclosed cells. The small molecules allopurinol and 6-azauridine are prodrugs that, upon conversion into allopurinol ribonucleotide and 6-aza-UMP (Bono et al., 1964; Handschumacher, 1960; Kelley and Beardmore, 1970; Murrell and Rapeport, 1986), respectively, competitively inhibit the ODC domain of UMPS (FIG. 6B). In K562 cells, allopurinol dose-dependently increased the levels of carbamoylaspartate, dihydroorotate, orotate, orotidine, and OMP (FIGS. 11A-B). Moreover, at its highest tested concentration, allopurinol also decreased by nearly 30% the abundance of UTP in these cells (FIG. 11C). Using LC/MS-based metabolite profiling, a species whose mass-to-charge ratio (m/z) matched the predicted m/z of allopurinol ribonucleotide was detected, and the magnitude correlated with the concentration of allopurinol in the media (FIG. 11D). Importantly, this species could be distinguished from its isomer, IMP, by their differing chromatographic retention times. These data are consistent with the conversion of allopurinol to allopurinol ribonucleotide within the cell. However, a metabolite peak consistent with a putative uric acid ribonucleotide was not detected.

Figure 6C:
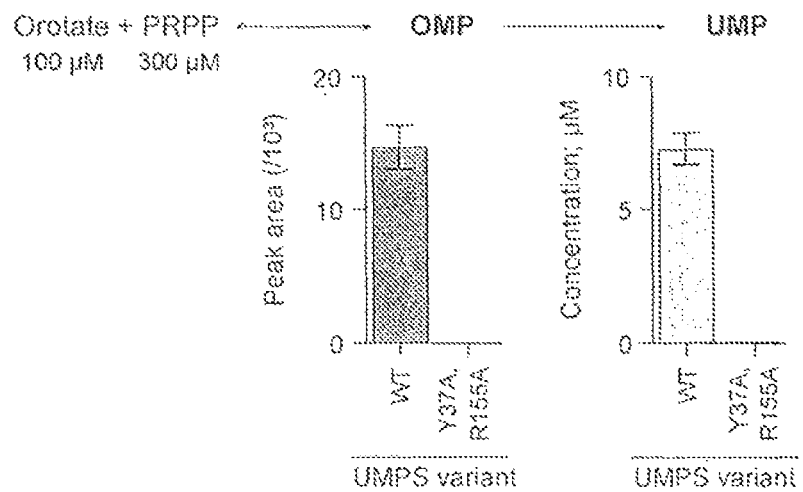
FIG. 6C depicts a quantification of OMP (left) and UMP (right) following incubation of recombinant UMPS (WT or the Y37A, R155A mutant) with its substrates orotate and PRPP at the indicated concentrations (mean±SD, n=3). WT: wild-type.
Figure 6D:
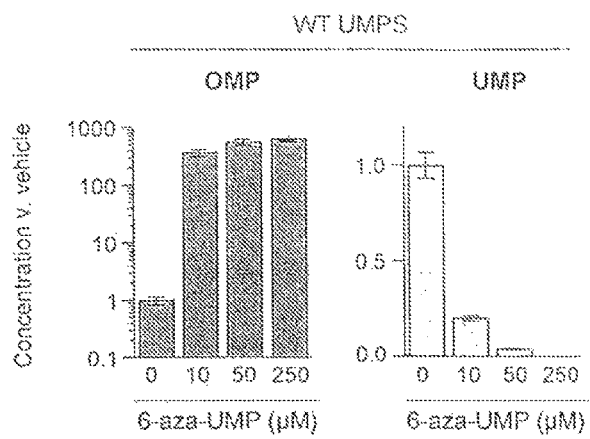
FIG. 6D depicts a relative abundances of OMP (left) and UMP (right) following addition of increasing concentrations of G-aza-UMP or vehicle to the UMPS activity assay (mean±SD, n=3).

To investigate whether uric acid itself might directly inhibit UMPS, we developed an in vitro UMPS activity assay containing recombinant UMPS and its substrates, orotate and PRPP, and verified its activity via the LC/MS detection of OMP and UMP (FIG. 6C). An UMPS mutant (Y37A, R155A), which was designed based on a recently deposited structure of the OPRT domain of human UMPS (Protein Data Bank entry 2WNS, chains A and B) (FIG. 12), had no activity and served as a negative control in the assay. The established ODC inhibitor, 6-aza-UMP, dose-dependently decreased UMP production by UMPS, and at 50 µM, reduced UMP levels to ~3% of those in reactions containing vehicle (FIG. 6D). 6-aza-UMP also dramatically increased the abundance of OMP, but the increase in OMP did not tightly correlate with the decrease in UMP. While not wishing to be bound by any theory, this result may be due to the known reversibility of the OPRT reaction (Traut and Jones, 1977).

Figure 6E:
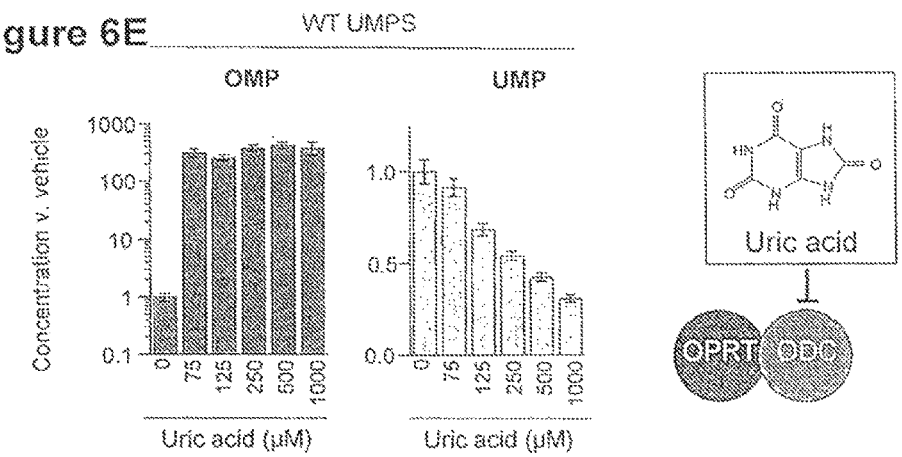
FIG. 6E depicts a relative abundances of OMP (left) and UMP (middle) following addition of increasing concentrations of uric acid or vehicle to the UMPS activity assay (mean±SD, n=3). Schematic depicting competitive inhibition of the ODC domain of UMPS by uric acid (right).
Figure 6F:
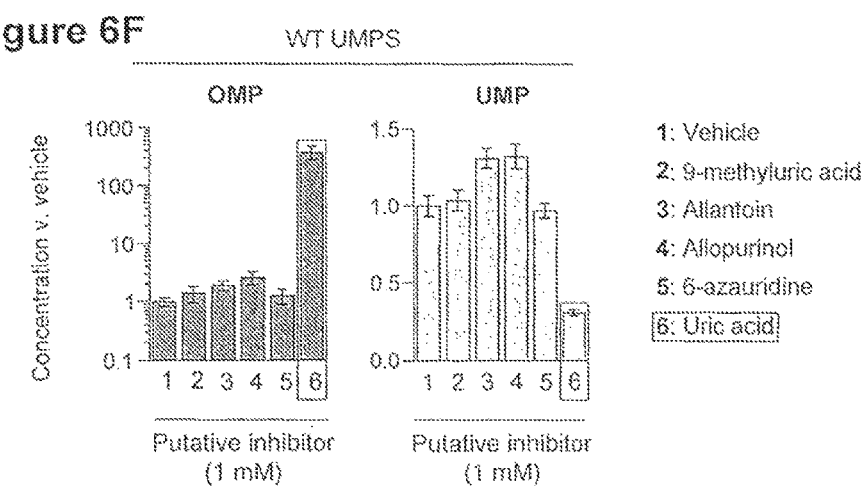
FIG. 6F depicts a relative abundances of OMP (left) and UMP (right) following addition of 9-methyluric acid, allantoin, allopurinol, 6-azauridine, uric acid, or vehicle to the UMPS activity assay (mean±SD, n=3).

Remarkably, uric acid also dose-dependently inhibited UMP production by UMPS, and, like 6-aza-UMP, also increased OMP in a fashion that did not completely correlate with the decrease in UMP (FIG. 6E). Uric acid was less potent than 6-aza-UMP, as at 1 mM, it could only reduce UMP levels to ~30% of those in reactions containing vehicle. Importantly, however, uric acid inhibited UMPS in vitro at concentrations consistent with those that boosted orotate and orotidine levels in cultured cells. Lastly, allopurinol and 6-azauridine did not directly inhibit UMPS, and neither did 9-MUA or allantoin (FIG. 6F).

Thus, uric acid, at the concentrations present in human plasma, is a direct inhibitor of the ODC domain of UMPS.

Example 5: Uric Acid Antagonizes the Cytotoxicity of 5-Fluorouracil

Figure 7A:
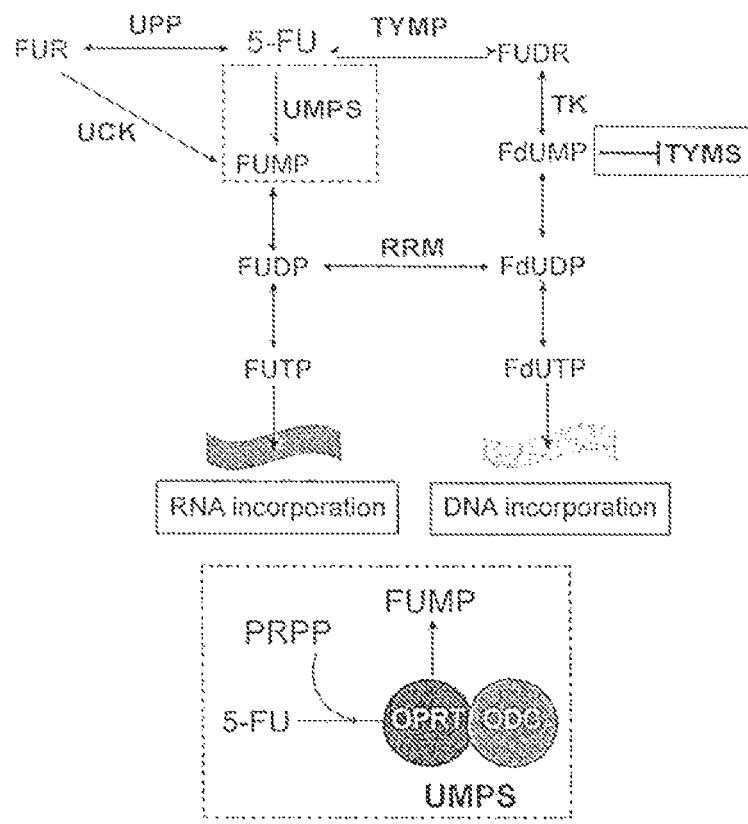
FIG. 7A is a schematic depicting the metabolism of 5-fluorouracil (5-FU) (top). 5-FU is converted into various fluoronucleotide derivatives that mediate its cytotoxic effects. Fluorouridine triphosphate (FUTP) and fluorodeoxyuridine triphosphate lead to cell death upon misincorporation into RNA and DNA, respectively. Fluorodeoxyuridine monophosphate (FdUMP) leads to cell death by inhibition of thymidylate synthase (TYMS) (Longley et al., 2003). Enzymes depicted are uridine phosphorylase (UPP), uridine-cytidine kinase (UCK), thymidine phosphorylase (TYMP), thymidine kinase (TK), and ribonucleotide reductase (RRM). Other metabolites indicated are fluorouridine (FUR), fluorouridine monophosphate (FUMP), fluorouridine diphosphate (FUDP), fluorodeoxyuridine (FUDR), and fluorodeoxyuridine diphosphate (FdUDP). The OPRT domain of UMPS catalyzes the direct conversion of 5-FU to FUMP (bottom).
Figure 7B:
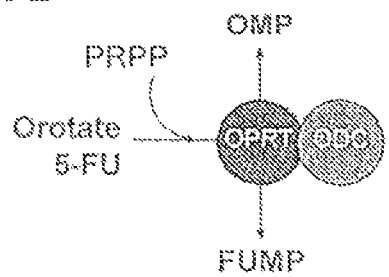
FIG. 7B is a schematic showing that the OPRT domain of UMPS catalyzes the conversions of orotate to OMP and 5-FU to FUMP. Dose-response of NOMO1 cells to 5-FU (FIG. 7C) or doxorubicin (FIG. 7D) when cultured in RPMI$^{+IFS}$ (dark gray), RPMI$^{+dIFS}$ (light gray), or HPLM$^{+dIFS}$ (green) (mean±SD, n=9). Data points are the average of three independent biological experiments that each consisted of three technical replicates (left plot). EC$_{50}$ of 5-FU (FIG. 7C) or doxorubicin (FIG. 7D) in NOMO1 cells when cultured in RPMI$^{+IFS}$ (dark gray), RPMI$^{+dIFS}$ (light gray), or HPLM$^{+dIFS}$ (green). Horizontal bar indicates the mean of three independent biological experiments; * p<0.001; ns: not significant (right plot). Dose-response of NOMO1 cells to 5-FU (FIG. 7E) or doxorubicin (FIG. 7F) when cultured in HPLM$^{+IFS}$ (green) or HPLM$^{+dIFS}$ lacking uric acid (blue) (mean±SD, n=9). Data points are the average of three independent biological experiments that each consisted of three technical replicates (left plot). EC$_{50}$ of 5-FU or doxorubicin in NOMO1 cells when cultured in HPLM$^{+IFS}$ (green) or HPLM$^{+dIFS}$ lacking uric acid (blue). Horizontal bar indicates the mean of three independent biological experiments; * p<0.001; ns: not significant (right plot).

5-Fluorouracil (5-FU) is an antimetabolite drug that, although developed over fifty years ago, remains widely used in the treatment of several types of cancer (Longley et al., 2003). In cells, 5-FU is metabolized into various fluoronucleotide derivatives that mediate its cytotoxic effects (FIG. 7A). Among these is fluorouridine triphosphate (FUTP), which leads to cell death upon its misincorporation into RNA. FUTP synthesis begins with the conversion of 5-FU to fluorouridine monophosphate (FUMP), either directly by the OPRT domain of UMPS or indirectly through the sequential activities of uridine phosphorylase and uridine kinase (Longley et al., 2003). Previous kinetic studies show that orotate competes with 5-FU for its direct conversion to FUMP by OPRT activity (Reyes and Guganig, 1975) (FIG. 7B). Consistent with these findings, allopurinol reduces the sensitivity of certain cancer cell lines to 5-FU (Schwartz and Handschumacher, 1979), owing to orotate accumulation induced by competitive inhibition of the ODC domain of UMPS mediated by allopurinol ribonucleotide. Thus, without wishing to be bound by any theory, uric acid might impact the sensitivity of cells to 5-FU through a similar mechanism.

Figure 7C:
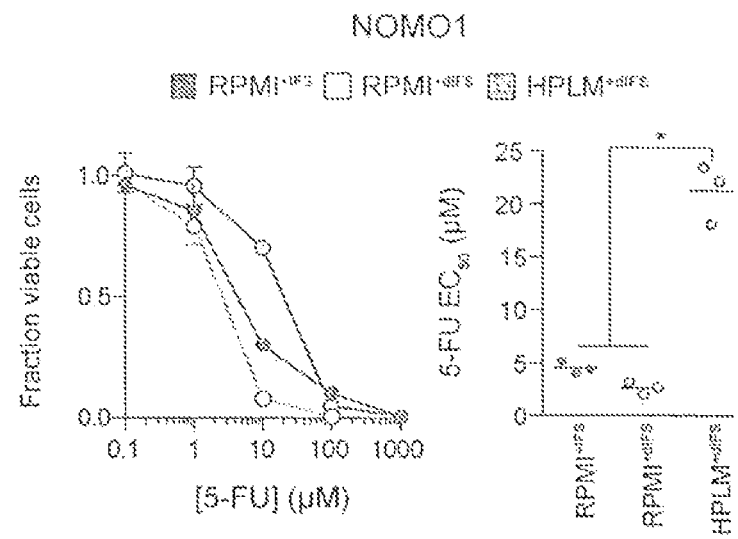
FIG. 7G depicts intracellular abundances of 5-FU (left), FdUMP (middle), and FUMP (right) in NOMO1 cells treated with 20 µM 5-FU and cultured for 24 hr in HPLM$^{+}_{dIFS}$ (green) or HPLM$^{+dIFS}$ lacking uric acid (blue) (mean±SD, n=3). ND: not detected.
FIG. 7H depicts a proposed mechanism of uric acid-mediated antagonism of cytotoxicity caused by 5-FU. Without wishing to be bound by any theory, as either the OPRT domain of UMPS or the sequential actions of UPP and UCK can convert 5-FU to FUMP, the influence of uric acid on 5-FU sensitivity likely depends on the extent that a given cell type generates FUMP via OPRT-mediated synthesis.
Figure 7D:
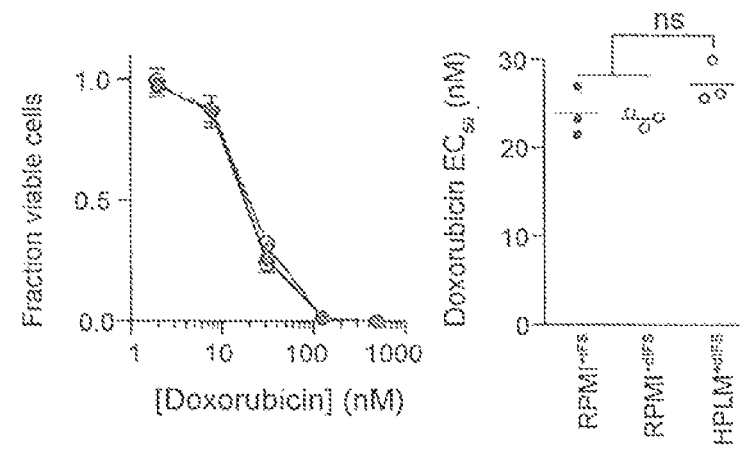
Figure 7E:
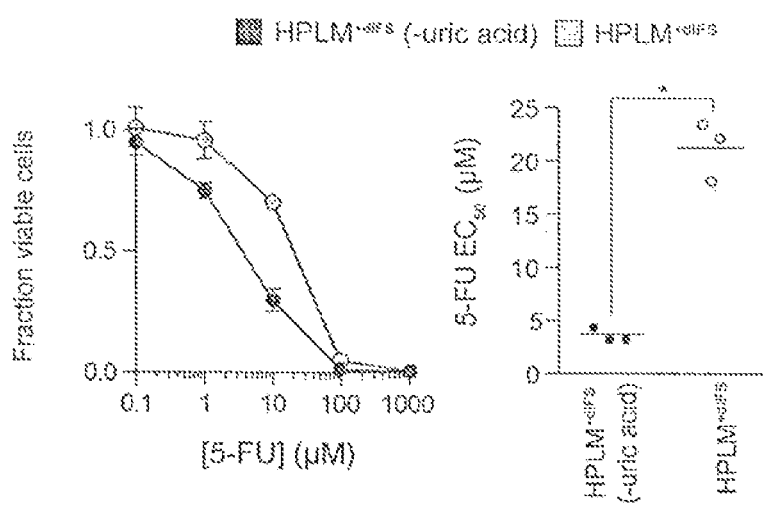
Figure 7F:
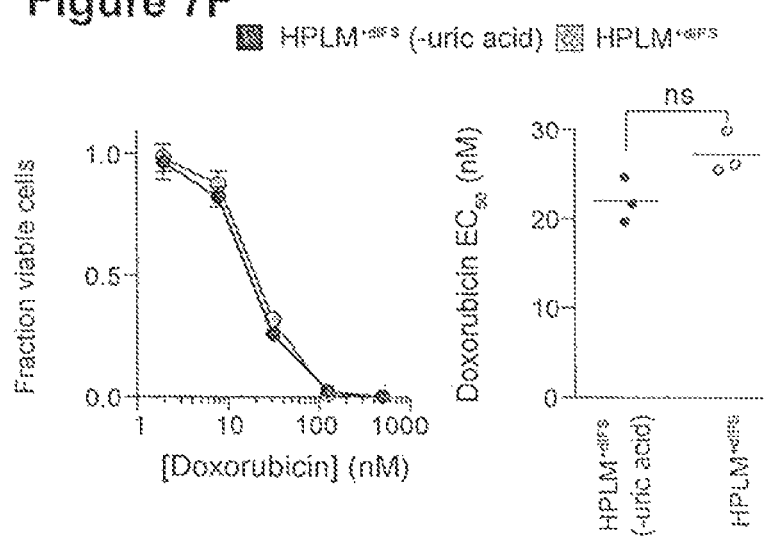
Figure 7G:
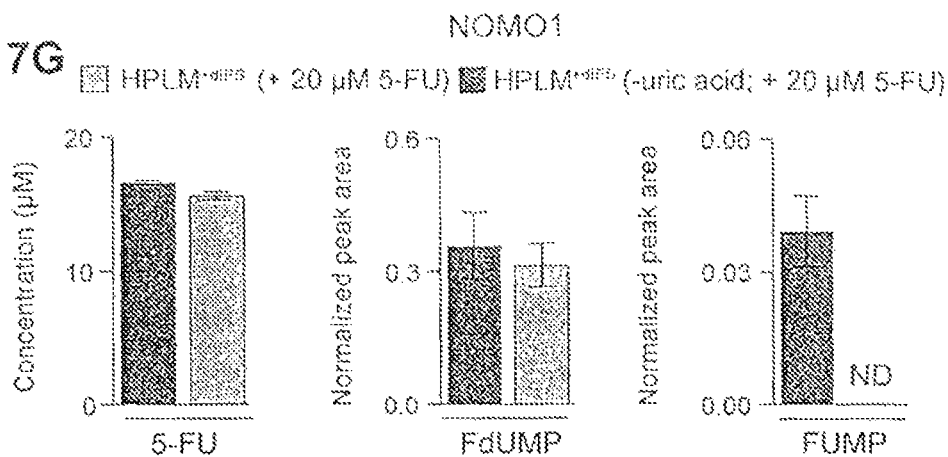

Indeed, culture of NOMO1 cells in HPLM$^{+dIFS}$ decreased the EC$_{50}$ of 5-FU by ~5- and ~8-fold compared to in RPMI$^{+IFS}$ and RPMI$^{+dIFS}$, respectively (FIG. 7C), without affecting the potency of doxorubicin—a DNA-damaging drug also commonly used in the treatment of cancer (FIG. 7D). Moreover, removal of just uric acid from HPLM$^{+dIFS}$ reduced the EC$_{50}$ of 5-FU in NOMO1 cells by nearly 6-fold (FIG. 7E), again without affecting doxorubicin sensitivity (FIG. 7F). In cells treated with 5-FU and cultured in HPLM$^+$ $_{dIFS}$ lacking uric acid, FUMP, fluorodeoxyuridine monophosphate (FdUMP), as well as 5-FU were detected (FIG. 7G). While culture in uric acid-containing HPLM$^{+dIFS}$ had little effect on the intracellular abundances of FdUMP and 5-FU, it reduced FUMP levels below the limit of detection, consistent with antagonism of OPRT-mediated FUMP synthesis by orotate (FIG. 7G).

As 5-FU is no longer used in the treatment of hematological cancers, the effect of uric acid on 5-FU sensitivity of a more clinically relevant cancer cell line (Longley et al., 2003) was studied. As in the six hematological cancer cell lines, culture of the SW620 colorectal cancer cell line in HPLM$^{+dIFS}$ increased the intracellular abundance of orotate (FIG. 13A), indicating that uric acid might also affect the 5-FU sensitivity of these cells. Indeed, removal of just uric acid from HPLM$^{+dIFS}$ reduced the 5-FU EC$_{50}$ of SW620 cells by 3-fold relative to that in HPLM$^{+dIFS}$ (Figure S6B), but did not influence doxorubicin sensitivity (FIG. 13C).

Figure 7H:
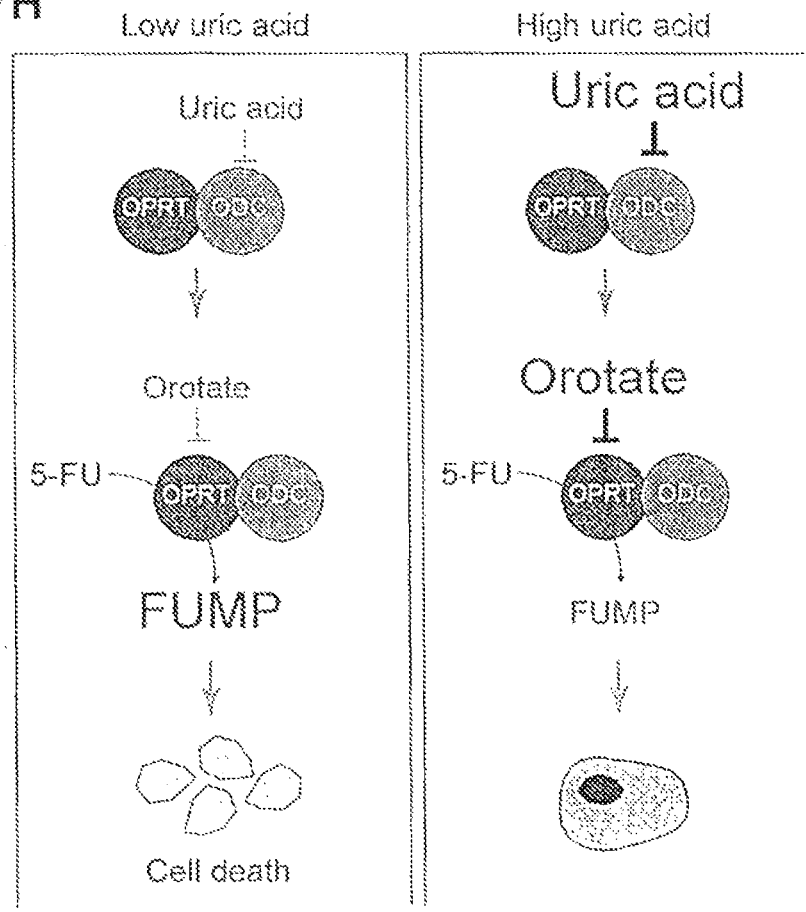

Thus, at concentrations found in human plasma, the endogenous metabolite uric acid affects the sensitivity of cancer cells to a common chemotherapeutic (FIG. 7H), suggesting that manipulations of plasma uric acid levels, such as by administration of uricase (Jeha et al., 2004), could improve the 5-FU sensitivity of human tumors that generate FUMP via OPRT-mediated synthesis.

Materials and Methods

Cell Lines and Reagents

The following cell lines were kindly provided by: K562 and NOMO1, Dr. James Griffin (Dana Farber Cancer Institute); P12-Ichikawa, Dr. Thomas Look (Dana Farber Cancer Institute); SUDHL4, Dr. Margaret Shipp (Dana Farber Cancer Institute); and KMS12BM and SEM from the Cancer Cell Line Encyclopedia (Broad Institute). The SW620 cell line was purchased from ATCC. Cell lines were verified to be free of *mycoplasma* contamination (Freshney, 2010) and the identities of all cell lines were authenticated by STR profiling. STR profiling of SW620 revealed very minor background in 2 of the 10 loci evaluated.

5-fluorouracil (F6627), 6-azauridine (A1882), allantoin (05670), allopurinol (PHR1377), doxorubicin (44583), orotate (08402), phosphoribosyl pyrophosphate (PRPP) (P8296), UMP (U6375) were obtained from Sigma; 6-aza-UMP (sc-291171) and 9-methyluric acid (sc-362184) were obtained from Santa Cruz Biotechnologies; [U-$^{13}$C$_6$]-D-glucose (CLM-1396) and phenylalanine-d8 (DLM-372) were obtained from Cambridge Isotope Laboratories.

Vendors and catalog number of compounds used in the formulation of HPLM are listed in Table 7. The compounds used in HPLM were prepared as stock solutions containing one or more compounds as listed in Table 7, in addition to RPMI, which provided biotin, choline, folate, myo-inositol, niacinamide, p-aminobenzoate, pantothenate, pyridoxine, riboflavin, thiamine, and vitamin B-12.

TABLE 7

Stock solutions used for HPLM preparation

| Stock solution pool # | Components | Stock concentration | Storage |
|---|---|---|---|
| 1 | glucose | 100X | Prepared fresh |
| 2 | alanine, arginine, asparagine, cysteine, glycine, proline, serine | 500X | Aliquots stored frozen at −20 C. |
| 3 | aspartate, cysteine, glutamate, tyrosine | 500X | Prepared in 1M HCl; aliquots stored frozen at −20 C. |
| 4 | glutamine | 250X | Aliquots stored frozen at −20 C. |
| 5 | histidine, isoleucine, leucine, lysine, methionine, phenylalanine, threonine, tryptophan, valine | 500X | Prepared in 0.1M HCl; aliquots frozen at −20 C. |
| 6 | $CaCl_2$, KCl, $MgCl_2$, $MgSO_4$ NaCl | 10X | Aliquots stored frozen at −20 C. |
| 7 | $NaHCO_3$, $Na_2HPO_4$ | 10X | Aliquots stored frozen at −20 C. |
| 8 | $Ca(NO_3)_2 \cdot 4H_2O$, $NH_4Cl$ | 100X | Aliquots stored frozen at −20 C. |
| 9 | 2-hydroxybutyrate, 3-hydroxy butyrate, acetate, citrate, lactate, malonate, pyruvate, succinate | 250X | Aliquots stored frozen at −20 C. |
| 10 | 4-hydroxyproline, acetylglycine, alpha-aminobutyrate, betaine, carnitine, citrulline, ornithine, taurine | 500X | Aliquots stored frozen at −20 C. |
| 11 | creatine, creatinine | 500X | Aliquots stored frozen at −20 C. |
| 12 | acetone | 5000X | Aliquots stored frozen at −20 C. |
| 13 | formate | 5000X | Aliquots stored frozen at −20 C. |
| 14 | fructose, galactose | 500X | Aliquots stored frozen at −20 C. |
| 15 | glycerol | 5000X | Aliquots stored frozen at −20 C. |
| 16 | hypoxanthine | 1000X | Prepared in 0.2M HCl; aliquots frozen at −20 C. |
| 17 | urea | 250X | Prepared fresh |
| 18 | uric acid | 250X | Prepared fresh in 1M NaOH |
| 19 | phenol red | 100X | Aliquots stored frozen at −20 C. |

Plasmids and Plasmid Construction pDONR223-KRASV12 and pLJM1-eGFP were obtained from Addgene (Addgene 31200 and 19319, respectively). pDONR223-LIMPS was from Human ORFeome 7.1 and was kindly provided by Dr. Susan Lindquist. All other plasmids were constructed as described below.

1. Construction of Lentiviral Plasmid pLJC2

The KRASV12 gene was amplified from the pDONR223-KRASV12 template using the primers JC4/JC5, digested with AgeI-BamHI, and cloned into pLJM1-eGFP to generate pLJM1-KRASV12-3×FLAG. Plasmid pLJC1-KRASV12 was constructed using QuickChange PCR to remove two NotI sites of pLJM1-KRASV12-3×FLAG with the primers JC48/JC49 and JC50/JC51, respectively. The Rap2A gene was amplified from the pLJM1-Rap2A template using the primers JC68/JC69, digested with PacI-NotI, and cloned into pLJC1-KRASV12-3×FLAG to generate pLJC1-Rap2A-3×FLAG. The sequence encoding Rap2A-3×FLAG was then amplified from pLJC1-Rap2A-3×FLAG using the primers JC_LJC2-F/JC79, digested with AgeI-EcoRI, and cloned into pLJM1-eGFP to generate pLJM1-Rap2A-3×FLAG. Plasmid pLJC2-Rap2A-3×FLAG was then constructed using QuickChange PCR to remove two NotI sites of pLJM1-Rap2A-3×FLAG with the primers JC48/JC49 and JC50/JC51, respectively.

2. Construction of UMPS Plasmids

The UMPS gene was amplified from the pDONR223-UMPS template using the primers JC624/JC625, digested with PacI-NotI, and cloned into pLJC2-Rap2A-3×FLAG to generate pLJC2-UMPS-3×FLAG. Plasmid pLJC2-UMPS (Y37A, R155A)-3×FLAG was constructed using a 2-step protocol based on overlap extension PCR methodology. In the first step, three fragments were amplified from the pLJC2-UMPS-3×FLAG template using the following primer pairs: JC_LJC2-F/JC716, JC715/JC720, and JC719/JC_LJC2-R. In the second step, the three fragments were pooled in a second PCR containing the primers JC_LJC2-F/JC_LJC2_R, then digested with PacI-NotI, and cloned into pLJC2-UMPS-3×FLAG.

Primers

JC4:
(SEQ ID NO: 1)
GCACCGGTTTAATTAACGCCACCATGGGCACTGAATATAAACTTGTGGTA

GTTGG

JC5:
(SEQ ID NO: 2)
CGCGGATCCTTATTACTTGTCATCGTCATCCTTGTAATCAATGTCATGAT

CTTTATAATCACCGTCATGGTCTTTGT (SEQ ID NO: 3)
AGTCGCCTGCGGCCGCCATAATTACACACTTTGTCTTTGACTTC

JC48:
(SEQ ID NO: 4)
CCACCGCACAGCAAGCAGCAGCTGATCTTCAGACC

JC49:
(SEQ ID NO: 5)
GCTGCTTGATGCCCCAGACTGTGAGTTGCAACAG

JC50:
(SEQ ID NO: 6)
CGAGACTAGCCTCGAGCAGCAGCCCCCTTCACCGAG

JC51:
(SEQ ID NO: 7)
CCGCATCACCATGGTAATAGCGATGACTAATACG

JC68:
(SEQ ID NO: 8)
CCGTTAATTAAAGGGACGATGCGCGAGTACAAAGTGGTGGTGCTG

JC69:
(SEQ ID NO: 9)
CCCTTGCGGCCGCGCTGCCTCCTTGTATGTTACATGCAGAACAGC

JC_LJC2-F:
(SEQ ID NO: 10)
TGTACGGTGGGAGGTCTATATAAG

JC79:
(SEQ ID NO: 11)
CGGCGGGAATTCTTATTACTTGTCATCGTCATCCTTGTAATCAATGTCAT

G

JC624:
(SEQ ID NO: 12)
CCGTTAATTAACGCGACAATGGCGGTCGCTCGTGCAGCTTTGGGGCCATT

```
GGTGAC

JC625:
                                                (SEQ ID NO: 13)
CCCTTGCGGCCGCGCTGCCTCCAACACCAAGTCTACTCAAATACGCTTCC
CAAGC

JC715:
                                                (SEQ ID NO: 14)
CTTTCCTCCCCCATCGCCATCGATCTGCGGGGC

JC716:
                                                (SEQ ID NO: 15)
GCCCCGCAGATCGATGGCGATGGGGGAGGAAAG

JC719:
                                                (SEQ ID NO: 16)
GTGCTGTTGGACGCCGAGCAGGGAGGCAAG

JC720:
                                                (SEQ ID NO: 17)
CTTGCCTCCCTGCTCGGCGTCCAACAGCAC

JC_LJC2-R:
                                                (SEQ ID NO: 18)
CCCTTTTCTTTTAAAATTGTGGATGAATACTGCC
```

Design of HPLM

The Human Metabolome Database, which is integrated with the Serum Metabolome Database, (Psychogios et al., 2011; Wishart et al., 2013) contains 2,192 metabolites that are designated as being both detected and quantified in at least one human biofluid. From this collection, molecules that met one of the following manually applied filtering criteria were removed: (1) Metabolites for which a concentration in normal adult human blood was not indicated; (2) Lipophilic metabolites, including fatty acids, cholesterol, and derivatives of the following: cholesterol ester, ceramide, diglyceride, ganglioside, glycerophosphocholine, monoacylglyceride, phosphatidic acid, phosphatidylglycerol, phosphatidylinositol, phosphatidylserine, sphingomyelin, and triglyceride; (3) Metabolites with concentrations in normal adult human blood <6 µM as denoted by at least one reference source; (4) Metabolites with concentrations in normal adult human blood indicated by only one reference source; and (5) Metabolites that were not commercially available. Although vitamins are among the nutritional requirements of cells in culture (Eagle, 1955), most had annotated plasma concentrations that were well below the 6 µM threshold we set. Therefore, rather than omit these metabolites, HPLM was supplemented with a commercial concentrated mixture of vitamins at concentrations equivalent to those of RPMI 1640. In addition, while trace elements such as copper and zinc are also essential for cells in culture, they are often contributed in sufficient quantities by transport molecules in IFS, such as albumin and insulin, and exceeding their necessary levels is often detrimental to cell proliferation (Sigma Media Expert). Thus, trace elements were not included among the defined components of HPLM. Additional modifications, such as removal of non-endogenous compounds and gases, were also made to generate the final list of proteinogenic amino acids, 27 additional polar metabolites, and 10 small ions included in the formulation of HPLM at concentrations similar to the calculated average of values reported for normal adult human blood.

Cell Culture Media Formulations

Cells were primarily maintained in the following three media:

(1) RPMI$^{+IFS}$: RPMI 1640 lacking glucose (Thermo Fisher Scientific 11879020) to which we added 5 mM glucose, 10% heat inactivated fetal bovine serum (IFS), penicillin, and streptomycin.

(2) RPMI 1640 lacking glucose (Thermo Fisher Scientific 11879020) to which we added 5 mM glucose, 10% dialyzed IFS, penicillin, and streptomycin.

(3) HPLM$^{+dIFS}$: HPLM (See Table 2) to which we added 10% dialyzed IFS, RPMI 1640 100× Vitamins (Sigma R7256), penicillin, and streptomycin.

Heat inactivated fetal bovine serum (Sigma F4135) was dialyzed against a 20× volume of PBS, using SnakeSkin dialysis tubing, 3.5K MWCO, 35 mm (Thermo Fisher Scientific PI88244). Dialysis was carried out for 48 hr at 4° C. with a complete PBS exchange every 9-12 hr. All media were sterile filtered using bottle-top vacuum filters, cellulose acetate membrane, pore size 0.45 µm (Sigma CLS430514).

Cell Culture Conditions

Prior to all experiments, cells were grown in the medium of interest for at least 7 days to allow for adaptation. All cells were maintained at 37° C. and 5% $CO_2$.

For growth curves, all cell lines were seeded at a density of 100,000 cells/mL and grown in 25 $cm^2$ rectangular canted neck cell culture flasks (Westnet 430639) in 12 mL of medium. Cell density measurements were recorded every 9-12 hr using a Beckman Z2 Coulter Counter with a diameter setting of 8-30 µm.

Metabolite Profiling and Quantification of Metabolite Abundance

LC/MS-based analyses were performed on a QExactive benchtop orbitrap mass spectrometer equipped with an Ion Max source and HESI II probe, which was coupled to a Dionex UltiMate 3000 UPLC system (Thermo Fisher Scientific). External mass calibration was performed using the standard calibration mixture every 7 days. Acetonitrile was LC/MS HyperGrade (EMD Millipore). All other solvents were LC/MS Optima grade (Thermo Fisher Scientific).

For metabolite profiling of media and plasma, samples were diluted 1:40 in a solution containing 50% methanol, 30% acetonitrile, 20% water with 10 ng/mL phenylalanine-$d_8$ as an internal standard, and then stored at −80° C. Following a 5 min vortex and centrifugation at 21130 g for 5 min at 4° C., 2 µL of each media metabolite sample was injected onto a ZIC-pHILIC 2.1×150 mm analytical column equipped with a 2.1×20 mm guard column (both 5 µm particle size, EMD Millipore). Buffer A was 20 mM ammonium carbonate, 0.1% ammonium hydroxide; buffer B was acetonitrile. The chromatographic gradient was run at a flow rate of 0.150 mL/min as follows: 0-20 min: linear gradient from 80% to 20% B; 20-20.5 min: linear gradient from 20% to 80% B; 20.5-28 min: hold at 80% B. The mass spectrometer was operated in full scan, polarity switching mode with the spray voltage set to 3.0 kV, the heated capillary held at 275° C., and the HESI probe held at 350° C. The sheath gas flow rate was set to 40 units, the auxiliary gas flow was set to 15 units, and the sweep gas flow was set to 1 unit. The MS data acquisition was performed in a range of 70-1000 m/z, with the resolution set to 70,000, the AGC target at $10^6$, and the maximum injection time at 20 msec.

For metabolite profiling of whole-cell samples, cells were pelleted and then seeded at a density of 200,000 cells/mL in 6-well plates in 3 mL of fresh culture medium. After 24 hr incubation, cells were centrifuged at 250 g for 5 min, resuspended in 1 mL ice-cold 0.9% sterile NaCl, and again centrifuged at 250 g for 5 min at 4° C. Metabolites were extracted in a 1 mL solution of 80% methanol containing 10 ng/mL phenylalanine-$d_8$ as an internal standard. Following a 10 min vortex and centrifugation for 3 min at 21130 g for 10 min at 4° C., samples were dried under nitrogen gas. Dried samples were stored at −80° C. and then resuspended in 100 μL water; 4 μL of each cell sample was injected for LC/MS analysis as described for profiling media samples. For all experiments, an additional culture replicate was set up identically and used for measuring cell number and volume, which were each measured using a Beckman Z2 Coulter Counter with a diameter setting of 8-30 μm.

For metabolite profiling of LIMPS activity assay samples, reaction mixtures were extracted as described (see LIMPS activity assay) and 5 μL of each sample was injected for LC/MS analysis as described for profiling media samples, except that the mass spectrometer was operated in full scan, negative ionization mode only.

A list of nearly 170 metabolites encompassing a variety of metabolic pathways and processes was created. From a library of chemical standards assembled by the Whitehead Institute Metabolite Profiling core facility, we constructed six pools of standards that together accounted for nearly 90% of this list. Standards were validated by LC/MS to confirm that they generated robust peaks at the expected m/z ratio. Stock solutions of each pool, containing 1 mM of each metabolite in water, were stored at −80° C. On the day of each run, these stocks were serially diluted in water, further diluted 1:10 into appropriate extraction solution, and then run in parallel with a given batch of biological samples.

Metabolite identification and quantification were performed with XCalibur QuanBrowser 2.2 (Thermo Fisher Scientific) using a 10 ppm mass accuracy window and 0.5 min retention time window. To confirm metabolite identities and to enable quantification, the aforementioned pools of metabolite chemical standards were used. Typically, the final concentrations of standards were 10 nM, 100 nM, 1 μM, 10 μM, and 100 μM. For glucose, chemical standard solutions were also made at concentrations of 125 μM and 250 μM. For certain metabolites, chemical standards were utilized only for metabolite identification. For those metabolites lacking a chemical standard, peak identification was restricted to high confidence peak assignments (Smith et al., 2005).

Because metabolite extraction protocols differed by sample type, the concentration of phenylalanine-d8 in processed samples varied: chemical standard pools (9 ng/mL), media and plasma samples (9.75 ng/mL), and cell samples (100 ng/mL). Therefore, the raw peak area of phenylalanine-d8 within each sample of a given batch was first normalized to account for these differences. To quantitate metabolites, we first divided the raw peak area of each metabolite by its corresponding normalized phenylalanine-d8 peak area. From the normalized metabolite peak areas of a given chemical standard, we then generated a corresponding standard curve fit to a quadratic log-log equation, typically with $r^2 > 0.95$, which was used to determine the metabolite concentration in each biological metabolite extract. The total number of moles of a metabolite in a particular whole-cell or medium/plasma extract was then calculated from the sample concentration and the corresponding sample volume. Thus, the final metabolite concentrations in biological samples were calculated using the appropriate equation below:

Media and plasma samples: Concentration by standard curve×40

Whole-cell samples: Concentration by standard curve× 100/(cell volume, in μL)

For those metabolites that were not quantified using a standard curve, normalized peak areas were used in the above calculations.

Glucose Tracing

Cells were pelleted and then seeded at a density of 200,000 cells/mL in 6-well plates in 3 mL of culture medium containing 5 mM [U-$^{13}$C]-glucose. After a 24 hr incubation, metabolite extractions were performed identically as described for whole-cell samples above.

5-FU Treatment for LC/MS

NOMO1 cells were pelleted and then seeded at a density of 200,000 cells/mL in 6-well plates in 3 mL of culture medium containing 20 μM 5-FU. After 24 hr incubation, metabolite extractions were performed identically as described for whole-cell samples above.

Highly Targeted Metabolomics

For the highly targeted analyses of FdUMP and FUMP in whole-cell samples following 5-FU treatment, the instrument was run as described above, but with an additional tSIM (targeted selected ion monitoring) scan in negative ionization mode. The tSIM settings were as follows: resolution set to 70,000, an AGC target of $10^5$, and a maximum integration time of 250 msec. The target masses were 325.0243 (corresponding to FdUMP) and 341.0192 (corresponding to FUMP). The isolation window around each target mass was set to 1.0 m/z.

For orotate, PRPP, OMP, and UMP in UMPS assay samples, all settings as described for the tSIM scan used for FdUMP and FUMP were identical except that the maximum integration time was 200 msec, and the target masses were 155.0088 (corresponding to orotate), 323.0286 (corresponding to UMP), 367.0184 (corresponding to OMP), and 388.9445 (corresponding to PRPP).

Consumption and Secretion Rates

At each time point that cell density was measured in growth curve construction, a small aliquot of the culture was carefully removed, centrifuged at 250 g for 5 min at 4° C., and metabolites were extracted from the resulting supernatant as described for media and plasma samples above. Upon completion of each growth curve, we determined a time point that fell within the middle of the exponential phase of proliferation, and profiled the metabolite extraction of conditioned medium collected at that time point. We profiled fresh media in parallel and the specific consumption/secretion rate for a given metabolite was obtained according to the simplified Monod model, $q=\mu/Y_{X/S}$, which expands to: $q=\mu \times V \times (\Delta M/\Delta X)$, where μ is the specific growth rate, V is the culture volume, $\Delta M$=metabolite concentration, $t_{final}$—metabolite concentration, $t_{initial}$, and $\Delta X$=cell density, $t_{final}$—cell density, $t_{initial}$. In this manner, we calculated q for the following metabolites: glucose, lactate, orotate, and orotidine.

Expression and Immunopurification of Recombinant UMPS

For transfection of HEK-293 T cells, 4 million cells were plated in 15 cm culture dishes. After 24 hr, cells were transfected with 15 μg of pLJC2-UMPS-3×FLAG or pLJC2-UMPS (Y37A, R155A)-3×FLAG using the polyethylenimine method (Boussif et al., 1995). After 48 hr, cells were rinsed one time with ice-cold PBS and then immediately lysed with lysis buffer (1% Triton X-100, 40 mM Tris-HCl pH 7.5, 100 mM NaCl, 5 mM $MgCl_2$, 1 tablet of EDTA-free protease inhibitor (Roche 11580800; per 25 mL buffer), 1 tablet of PhosStop phosphatase inhibitor (Roche 04906845001; per 10 mL buffer)). The cell lysates were cleared by centrifugation at 21130 g for 10 min at 4° C. For anti-FLAG immunoprecipitation, the FLAG-M2 affinity gel (Sigma A2220) was washed 3 times in lysis buffer. For each experiment, 500 µL of a 50/50 slurry of the affinity gel was then added to a pool of clarified lysates collected from 5 individual 15 cm culture dishes, and incubated with rotation for 3 hr at 4° C. Following immunoprecipitation, the beads were washed 2 times in lysis buffer and 3 times with lysis buffer containing 500 mM NaCl. Recombinant protein was then eluted in lysis buffer containing 1 mg/mL FLAG peptide for 1 hr at 4° C. The eluent was isolated by centrifugation at 100 g for 4 min at 4° C. (BioRad micro bio-spin column 732-6204), buffer exchanged (Amicon Ultra 30K NMWL) against 20 volumes of storage buffer (40 mM Tris-HCl pH 7.5, 100 mM NaCl, 1.5 mM dTT), mixed with glycerol (final concentration 15% v/v), and finally snap-frozen with liquid nitrogen and stored at −80° C. Protein samples were quantified using Bradford reagent and a BSA standard, and verified by 12% SDS-PAGE.

LIMPS Activity Assay

Reactions of each purified LIMPS variant (20-40 nM enzyme) with orotate (100 µM) and PRPP (300 µM) were carried out at 37° C. in 20 mM Tris-HCl pH 7.5, 5 mM $Na_2HPO_4$, 5 $MgCl_2$, 2 mM 2 mM dTT, 100 µM EDTA (adapted from (Han et al., 1995)), and various concentrations of putative inhibitors in a total volume of 100 µL. Following 20 min incubation, a 15 µL aliquot of the reaction mixture was removed and immediately added to 85 µL ice-cold 80% methanol for metabolite extraction, vortexed for 5 min, and centrifuged at 21130 g for 1 min at 4° C.

Stock solutions of 6-azauridine, 6-aza-UMP, 9-methyluric acid, allantoin, allopurinol, and uric acid were made up fresh at 200 mM in 1 M NaOH, and upon appropriate dilutions, had little effect on reaction pH.

Using the peak areas of a UMP chemical standard (final concentrations 625 nM, 1.25 µM, 2.5 µM, 5 µM, and 10 µM) identically prepared in 80% methanol, we generated a standard curve fit to a linear equation to ensure that UMP concentrations in the reaction samples did not exceed 10% of the initial orotate concentration. An OMP chemical standard was not available.

Drug Treatment Assays

NOMO1 cells were seeded at a density of 16,667 cells/mL in 6-well plates in 3 mL of culture medium. After 24 hr incubation, cells were treated with 5-FU (100 nM, 1 µM, 10 µM, 100 µM, or 1 mM) or doxorubicin (1.95 nM, 7.81 nM, 31.25 nM, 125 nM, or 500 nM). All wells, including untreated controls, contained 0.5% DMSO. Following addition of drugs, plates were gently shaken for 2 min. After 4 days of treatment, 200 µL from each well was transferred to a white 96-well plate (Greiner) and cell viability was assessed with Cell Titer-Glo (Promega). Luminescence was measured with a SpectraMax M5 Plate Reader (Molecular Devices) and normalized to an untreated control.

SW620 cells were seeded at a density of 2000 cells/well and allowed to attach for 24 hr. 5-FU and doxorubicin were prepared in DMSO and dispensed using an HP D300 compound dispenser. Cell viability was assessed with Cell-Titer Glo at 4 days following treatment and luminescence was measured as described above.

Dose-response values were plotted in GraphPad Prism and fit using a One Site-Fit log IC50 equation.

Collection of Mouse Plasma

The MIT Institutional Animal Care and Use Committee approved procedures for blood collection. Mice were maintained on regular chow at the specific pathogen free animal facility of the Whitehead Institute, and were fasted for eighteen hours prior to blood collection. At 10:00 AM, 100 µL of blood was collected into heparinized tubes from the facial vein of male wild-type mice of a C57Bl/6J background at an age of 3.5 months (n=4). To isolate plasma, the collected blood was centrifuged at 850 g for 6 min at 4° C. The plasma fraction was then transferred to a fresh tube and an aliquot was removed for metabolite extraction performed identically as described for media samples above.

Statistical Analysis

All p values were calculated using a two-tailed unpaired t test in GraphPad Prism 6.

REFERENCES

Adelman, R., Saul, R. L., and Ames, B. N. (1988). Oxidative damage to DNA: relation to species metabolic rate and life span. Proc Natl Acad Sci USA. 85, 2706-2708.

Atkinson, D. E. (1968). Energy charge of the adenylate pool as a regulatory parameter. Interaction with feedback modifiers. Biochemistry. 7, 4030-4034.

Álvarez-Lario, B., and Macarrón-Vicente, J. (2010). Uric acid and evolution. Rheumatology (Oxford). 49, 2010-2015.

Bailey, C. J. (2009). Orotic aciduria and uridine monophosphate synthase: A reappraisal. J Inherit Metab Dis. 32, 227-233.

Birsoy, K., Possemato, R., Lorbeer, F. K., Bayraktar, E. C., Thiru, P., Yucel, B., Wang, T., Chen, W. W., Clish, C. B., and Sabatini, D. M. (2014). Metabolic determinants of cancer cell sensitivity to glucose limitation and biguanides. Nature. 1-18.

Bobulescu, I. A., and Moe, O. W. (2012). Renal Transport of Uric Acid: Evolving Concepts and Uncertainties. Adv Chronic Kidney Dis. 19, 358-371.

Bono, V. H., Jr., Weissman, S. M., and Frei, E., III (1964). The Effect of 6-Azauridine Administration on De Novo Pyrimidine Production in Chronic Myelogenous Leukemia. J Clin Invest. 43, 1486-1494.

Boroughs, L. K., and DeBerardinis, R. J. (2015). Metabolic pathways promoting cancer cell survival and growth. Nat Cell Biol. 17, 351-359.

Cairns, R. A., Harris, I. S., and Mak, T. W. (2011). Regulation of cancer cell metabolism. Nat Rev Cancer. 11, 85-95.

Cantor, J. R., and Sabatini, D. M. (2012). Cancer cell metabolism: one hallmark, many faces. Cancer Discov. 2, 881-898.

Chandrasekera, P. C., and Pippin, J. J. (2014). Of rodents and men: species-specific glucose regulation and type 2 diabetes research. ALTEX. 31, 157-176.

Comerford, S. A., Huang, Z., Du, X., Wang, Y., Cai, L., Witkiewicz, A. K., Walters, H., Tantawy, M N., Fu, A., Manning, H. C., et al. (2014). Acetate Dependence of Tumors. Cell. 159, 1591-1602.

Commisso, C., Davidson, S. M., Soydaner-Azeloglu, R. G., Parker, S. J., Kamphorst, J. J., Hackett, S., Grabocka, E., Nofal, M., Drebin, J. A., Thompson, C. B., et al. (2013). Macropinocytosis of protein is an amino acid supply route in Ras-transformed cells. Nature. 497, 633-637.

Davidson, S. M., Papagiannakopoulos, T., Olenchock, B. A., Heyman, J. E., Keibler, M. A., Luengo, A., Bauer, M. R., Jha, A. K., O'Brien, J. P., Pierce, K. A., et al. (2016). Environment Impacts the Metabolic Dependencies of Ras-Driven Non-Small Cell Lung Cancer. Cell Metab. 23, 517-528.

DeBerardinis, R. J., and Chandel, N. S. (2016). Fundamentals of cancer metabolism. Sci Adv. 2, e1600200.

DeBerardinis, R. J., Lum, J. J., Hatzivassiliou, G., and Thompson, C. B. (2008). The Biology of Cancer: Metabolic Reprogramming Fuels Cell Growth and Proliferation. Cell Metab. 7, 11-20.

Demetrius, L. (2005). Of mice and men. EMBO Rep. 6, S39-S44. DeNicola, G. M., and Cantley, L. C. (2015). Cancer's Fuel Choice: New Flavors for a Picky Eater. Mol Cell. 60, 514-523.

Dulbecco, R., and Freeman, G. (1959). Plaque production by the polyoma virus. Virology. 8, 396-397.

Eagle, H. (1955a). The specific amino acid requirements of a human carcinoma cell (Stain HeLa) in tissue culture. J Exp Med. 102, 37-48.

Eagle, H. (1955b). The specific amino acid requirements of a mammalian cell (strain L) in tissue culture. J Biol Chem. 214, 839-852.

Eagle, H. (1955c). Nutrition needs of mammalian cells in tissue culture. Science. 122, 501-514.

Eagle, H. (1959). Amino Acid Metabolism in Mammalian Cell Cultures. Science. 130, 432-437.

Eason, K., and Sadanandam, A. (2016). Molecular or Metabolic Reprogramming: What Triggers Tumor Subtypes? Cancer Res. 76, 5195-5200.

Elsea, S. H., and Lucas, R. E. (2002). The mousetrap: what we can learn when the mouse model does not mimic the human disease. ILAR J. 43, 66-79.

Evans, D. R., and Guy, H. I. (2004). Mammalian Pyrimidine Biosynthesis: Fresh Insights into an Ancient Pathway. J Biol Chem. 279, 33035-33038.

Fallon, H. J., Frei, E., Block, J., and Seegmiller, J. E. (1961). The uricosuria and orotic aciduria induced by 6-azauridine. J Clin Invest. 40, 1906-1914.

Favaro, E., Bensaad, K., Chong, M. G., Tennant, D. A., Ferguson, D. J. P., Snell, C., Steers, G., Turley, H., Li, J.-L., Gunther, U. L., et al. (2012). Glucose Utilization via Glycogen Phosphorylase Sustains Proliferation and Prevents Premature Senescence in Cancer Cells. Cell Metab. 16, 751-764.

Fox, R. M., Royse-Smith, D., and O'Sullivan, W. J. (1970). Orotidinuria induced by allopurinol. Science. 168, 861-862.

Fox, R. M., Wood, M. H., and Royse-Smith, D. (1973). Hereditary orotic aciduria: types I and II. Am J. Med. 55, 791-798.

Freshney, R. I. (2010). Culture of Animal Cells. A Manual of basic technique and specialized applications. Sixth Edition. (Hoboken, N.J., USA: John Wiley & Sons, Inc.).

Handschumacher, R. E. (1960). Orotidylic Acid Decarboxylase: Inhibition Studies with Azauridine 5'-Phosphate. J Biol Chem. 235, 2917-2919.

Hensley, C. T., Faubert, B., Yuan, Q., Lev-Cohain, N., Jin, E., Kim, J., Jiang, L., Ko, B., Skelton, R., Loudat, L., et al. (2016). Metabolic Heterogeneity in Human Lung Tumors. Cell. 164, 681-694.

Hosios, A. M., Hecht, V. C., Danai, L. V., Johnson, M O., Rathmell, J. C., Steinhauser, M. L., Manalis, S. R., and Vander Heiden, M. G. (2016b). Amino Acids Rather than Glucose Account for the Majority of Cell Mass in Proliferating Mammalian Cells. Dev Cell. 36, 540-549.

Hu, J., Locasale, J. W., Bielas, J. H., O'Sullivan, J., Sheahan, K., Cantley, L. C., Vander Heiden, M G., and Vitkup, D. (2013). Heterogeneity of tumor-induced gene expression changes in the human metabolic network. Nat Biotechnol. 31, 522-529.

Ido, Y., Chang, K., and Williamson, J. R. (2004). NADH augments blood flow in physiologically activated retina and visual cortex. Proc Natl Acad Sci USA. 101, 653-658.

Jain, M., Nilsson, R., Sharma, S., Madhusudhan, N., Kitami, T., Souza, A. L., Kafri, R., Kirschner, M. W., Clish, C. B., and Mootha, V. K. (2012). Metabolite Profiling Identifies a Key Role for Glycine in Rapid Cancer Cell Proliferation. Science. 336, 1040-1044.

Jeha, S., Kantarjian, H., Irwin, D., Shen, V., Shenoy, S., Blaney, S., Camitta, B., and Pui, C.-H. (2004). Efficacy and safety of rasburicase, a recombinant urate oxidase (Elitek™), in the management of malignancy-associated hyperuricemia in pediatric and adult patients: final results of a multicenter compassionate use trial. Leukemia. 19, 34-38.

Jones, M. E. (1980). Pyrimidine nucleotide biosynthesis in animals: genes, enzymes, and regulation of UMP biosynthesis. Annu Rev Biochem. 49, 253-279.

Kamphorst, J. J., Nofal, M., Commisso, C., Hackett, S. R., Lu, W., Grabocka, E., Vander Heiden, M. G., Miller, G., Drebin, J. A., Bar-Sagi, D., et al. (2015). Human Pancreatic Cancer Tumors Are Nutrient Poor and Tumor Cells Actively Scavenge Extracellular Protein. Cancer Res. 75, 544-553.

Kand'ár, R., and Záková, P. (2008). Allantoin as a marker of oxidative stress in human erythrocytes. Clin Chem Lab Med. 46, 1270-1274.

Keibler, M.A., Wasylenko, T. M., Kelleher, J. K., Iliopoulos, o., Vander Heiden, M G., and Stephanopoulos, G. (2016). Metabolic requirements for cancer cell proliferation. Cancer Metab., 4:16.

Kelley, W. N., and Beardmore, T. D. (1970). Allopurinol: alteration in pyrimidine metabolism in man. Science. 169, 388-390.

Kratzer, J. T., Lanaspa, M. A., Murphy, M. N., Cicerchi, C., Graves, C. L., Tipton, P. A., Ortlund, E. A., Johnson, R. J., and Gaucher, E. A. (2014). Evolutionary history and metabolic insights of ancient mammalian uricases. Proc Natl Acad Sci USA. 111, 3763-3768.

Lehuede, C., Dupuy, F., Rabinovitch, R., Jones, R. G., and Siegel, P. M. (2016). Metabolic Plasticity as a Determinant of Tumor Growth and Metastasis. Cancer Res. 76, 5201-5208.

Longley, D. B., Harkin, D. P., and Johnston, P. G. (2003). 5-fluorouracil: mechanisms of action and clinical strategies. Nat Rev Cancer. 3, 330-338.

Lunt, S. Y., and Vander Heiden, M. G. (2011). Aerobic Glycolysis: Meeting the Metabolic Requirements of Cell Proliferation. Annu Rev Cell Dev Biol. 27, 441-464.

MacIver, N. J., Michalek, R. D., and Rathmell, J. C. (2013). Metabolic Regulation of T Lymphocytes. Annu Rev Immunol. 31, 259-283.

Maddocks, O. D. K., Berkers, C. R., Mason, S. M., Zheng, L., Blyth, K., Gottlieb, E., and Vousden, K. H. (2013). Serine starvation induces stress and p53-dependent metabolic remodelling in cancer cells. Nature. 493, 542-546.

Martignoni, M., Groothuis, G. M. M., and de Kanter, R. (2006). Species differences between mouse, rat, dog, monkey and human CYP-mediated drug metabolism, inhibition and induction. Expert Opin Drug Metab Toxicol. 2, 875-894.

Mashimo, T., Pichumani, K., Vemireddy, V., Hatanpaa, K. J., Singh, D. K., Sirasanagandla, S., Nannepaga, S., Piccirillo, S. G., Kovacs, Z., Foong, C., et al. (2014). Acetate Is a Bioenergetic Substrate for Human Glioblastoma and Brain Metastases. Cell. 159, 1603-1614.

Mayers, J. R., Torrence, M E., Danai, L. V., Papagiannakopoulos, T., Davidson, S. M., Bauer, M. R., Lau, A. N., Ji, B. W., Dixit, P. D., Hosios, A. M., et al. (2016). Tissue of origin dictates branched-chain amino acid metabolism in mutant Kras-driven cancers. Science. 353, 1161-1165.

Moore, G. E., Gerner, R E., and Franklin, H. A. (1967). Culture of normal human leukocytes. JAMA. 199, 519-524.

Murrell, G. A. C., and Rapeport, W. G. (1986). Clinical Pharmacokinetics of Allopurinol. Clin Pharmacokinet. 11, 343-353.

Oda, M., Satta, Y., Takenaka, O., and Takahata, N. (2002). Loss of urate oxidase activity in hominoids and its evolutionary implications. Mol Biol Evol. 19, 640-653.

Olson, K. A., Schell, J. C., and Rutter, J. (2016). Pyruvate and Metabolic Flexibility: Illuminating a Path Toward Selective Cancer Therapies. Trends Biochem Sci. 41, 219-230.

Pan, M., Reid, M. A., Lowman, X. H., Kulkarni, R. P., Tran, T. Q., Liu, X., Yang, Y., Hernandez-Davies, J. E., Rosales, K. K., Li, H., et al. (2016). Regional glutamine deficiency in tumours promotes dedifferentiation through inhibition of histone demethylation. Nat Cell Biol. 18, 1090-1101.

Pavlova, N. N., and Thompson, C. B. (2016). The Emerging Hallmarks of Cancer Metabolism. Cell Metab. 23, 27-47.

Pearce, E. L., Poffenberger, M. C., Chang, C. H., and Jones, R. G. (2013). Fueling Immunity: Insights into Metabolism and Lymphocyte Function. Science. 342, 1242454-1242454.

Psychogios, N., Hau, D. D., Peng, J., Guo, A. C., Mandal, R., Bouatra, S., Sinelnikov, I., Krishnamurthy, R., Eisner, R., Gautam, B., et al. (2011). The human serum metabolome. PLoS ONE. 6, e16957.

Reyes, P., and Guganig, M. E. (1975). Studies on a pyrimidine phosphoribosyltransferase from murine leukemia P1534J. Partial purification, substrate specificity, and evidence for its existence as a bifunctional complex with orotidine 5-phosphate decarboxylase. J Biol Chem. 250, 5097-5108.

Schug, Z. T., Peck, B., Jones, D. T., Zhang, Q., Grosskurth, S., Alam, I. S., Goodwin, L. M., Smethurst, E., Mason, S., Blyth, K., et al. (2015). Acetyl-CoA Synthetase 2 Promotes Acetate Utilization and Maintains Cancer Cell Growth under Metabolic Stress. Cancer Cell. 27, 57-71.

Schwartz, P. M., and Handschumacher, R. E. (1979). Selective antagonism of 5-fluorouracil cytotoxicity by 4-hydroxypyrazolopyrimidine (allopurinol) in vitro. Cancer Res. 39, 3095-3101.

Sellers, K., Fox, M. P., Bousamra, M., II, Slone, S. P., Higashi, R. M., Miller, D. M., Wang, Y., Yan, J., Yuneva, M. O., Deshpande, R., et al. (2015). Pyruvate carboxylase is critical for non-small-cell lung cancer proliferation. J Clin Invest. 125, 687-698.

Shaul, Y. D., Yuan, B., Thiru, P., Nutter-Upham, A., McCallum, S., Lanzkron, C., Bell, G. W., and Sabatini, D. M. (2016). MERAV: a tool for comparing gene expression across human tissues and cell types. Nucleic Acids Res. 44, D560-D566.

Shestov, A. A., Liu, X., Ser, Z., Cluntun, A. A., Hung, Y. P., Huang, L., Kim, D., Le, A., Yellen, G., Albeck, J. G., et al. (2014). Quantitative determinants of aerobic glycolysis identify flux through the enzyme GAPDH as a limiting step. Elife. 3, eLife.03342.

Smith, L. H., Jr., Sullivan, M., and Huguley, C. M., Jr. (1961). PYRIMIDINE METABOLISM IN MAN. IV. THE ENZYMATIC DEFECT OF OROTIC ACIDURIA. J Clin Invest. 40, 656-664.

Suchi, M., Mizuno, H., Kawai, Y., Tsuboi, T., Sumi, S., Okajima, K., Hodgson, M. E., Ogawa, H., and Wada, Y. (1997). Molecular cloning of the human UMP synthase gene and characterization of point mutations in two hereditary orotic aciduria families. Am J Hum Genet. 60, 525-539.

Tardito, S., Oudin, A., Ahmed, S. U., Fack, F., Keunen, O., Zheng, L., Miletic, H., Sakariassen, P. O., Weinstock, A., Wagner, A., et al. (2015). Glutamine synthetase activity fuels nucleotide biosynthesis and supports growth of glutamine-restricted glioblastoma. Nat Cell Biol. 17, 1556-1568.

Traut, T. W., and Jones, M. E. (1977). Kinetic and conformational studies of the orotate phosphoribosyltransferase: orotidine-5'-phosphate decarboxylase enzyme complex from mouse Ehrlich ascites cells. J Biol Chem. 252, 8374-8381.

Vander Heiden, M. G., Cantley, L. C., and Thompson, C. B. (2009). Understanding the Warburg Effect: The Metabolic Requirements of Cell Proliferation. Science. 324, 1029-1033.

Venneti, S., Dunphy, M. P., Zhang, H., Pitter, K. L., Zanzonico, P., Campos, C., Carlin, S. D., La Rocca, G., Lyashchenko, S., Ploessl, K., et al. (2015). Glutamine-based PET imaging facilitates enhanced metabolic evaluation of gliomas in vivo. Sci Transl Med. 7, 274ra17-274ra17.

Williamson, D. H., Lund, P., and Krebs, H. A. (1967). The redox state of free nicotinamide-adenine dinucleotide in the cytoplasm and mitochondria of rat liver. Biochem J. 103, 514-527.

Wishart, D. S., Jewison, T., Guo, A. C., Wilson, M., Knox, C., Liu, Y., Djoumbou, Y., Mandal, R., Aziat, F., Dong, E., et al. (2013). HMDB 3.0—The Human Metabolome Database in 2013. Nucleic Acids Res. 41, D801-D807.

Wu, X. W., Lee, C. C., Muzny, D. M., and Caskey, C. T. (1989). Urate oxidase: primary structure and evolutionary implications. Proc Natl Acad Sci USA. 86, 9412-9416.

Wu, X. W., Muzny, D. M., Lee, C. C., and Caskey, C. T. (1992). Two independent mutational events in the loss of urate oxidase during hominoid evolution. J. Mol Evol. 34, 78-84.

Wu, X., Wakamiya, M., Vaishnav, S., Geske, R., Montgomery C Jr., Jones, P., Bradley, A., and Caskey, C. T. (1994). Hyperuricemia and urate nephropathy in urate oxidase-deficient mice. Proc Natl Acad Sci USA. 91, 742-746.

Yao, C.-H., Fowle-Grider, R., Mahieu, N. G., Liu, G.-Y., Chen, Y.-J., Wang, R., Singh, M., Potter, G. S., Gross, R. W., Schaefer, J., et al. (2016). Exogenous Fatty Acids Are the Preferred Source of Membrane Lipids in Proliferating Fibroblasts. Cell Chem Biol. 23, 483-493.

Yuneva, M O., Fan, T. W. M., Allen, T. D., Higashi, R. M., Ferraris, D. V., Tsukamoto, T., Mates, J. M., Alonso, F. J., Wang, C., Seo, Y., et al. (2012). The Metabolic Profile of Tumors Depends on Both the Responsible Genetic Lesion and Tissue Type. Cell Metab. 15, 157-170.

Zhang, Q., Piston, D. W., and Goodman, R. H. (2002). Regulation of corepressor function by nuclear NADH. Science 295, 1895-1897.

Boussif, O., Lezoualc'h, F., Zanta, M A., Mergny, M. D., Scherman, D., Demeneix, B., and Behr, J. P. (1995). A versatile vector for gene and oligonucleotide transfer into cells in culture and in vivo: polyethylenimine. Proc Natl Acad Sci USA. 92, 7297-7301.

Han, B. D., Livingstone, L. R., Pasek, D. A., Yablonski, M. J., and Jones, M. E. (1995). Human uridine monophosphate synthase: baculovirus expression, immunoaffinity column purification and characterization of the acetylated amino terminus. Biochemistry 34, 10835-10843.

Smith, C. A., O'Maille, G., Want, E. J., Qin, C., Trauger, S. A., Brandon, T. R., Custodio, D. E., Abagyan, R., and Siuzdak, G. (2005). METLIN: a metabolite mass spectral database. Ther Drug Monit. 27, 747-751.

We claim:

1. A basal culture medium, comprising:
   at least 9 proteinogenic amino acids;
   one or more vitamins;
   one or more inorganic ions;
   glucose; and
   at least 10 small organic compounds selected from 4-hydroxyproline, acetylglycine, alpha-aminobutyrate, betaine, carnitine, citrulline, ornithine, taurine, 2-hydroxybutyrate, 3-hydroxybutyrate, acetate, citrate, formate, lactate, malonate, pyruvate, succinate, acetone, creatine, creatinine, glutathione, glycerol, urea, galactose, fructose, hypoxanthine, and uric acid.

2. The basal culture medium of claim 1, wherein the at least 10 small organic compounds comprise at least 4 amino acid derivatives or non-proteinogenic amino acids selected from 4-hydroxyproline, acetylglycine, alpha-aminobutyrate, betaine, carnitine, citrulline, ornithine, and taurine.

3. The basal culture medium of claim 1, wherein the at least 10 small organic compounds comprise at least 6 small organic compounds selected from 2-hydroxybutyrate, 3-hydroxybutyrate, acetate, citrate, formate, lactate, malonate, pyruvate, and succinate.

4. The basal culture medium of claim 1, wherein the at least 10 small organic compounds comprise at least 3 small organic compounds selected from acetone, creatine, creatinine, glutathione, glycerol, and urea.

5. The basal culture medium of claim 1, wherein the at least 10 small organic compounds comprise hypoxanthine, uric acid, or both.

6. The basal culture medium of claim 1, wherein the at least 10 small organic compounds comprise galactose, fructose, or both.

7. The basal culture medium of claim 1, wherein the at least 9 proteinogenic amino acids comprise at least 9 of the following amino acids: glycine, L-alanine, L-arginine, L-asparagine, L-aspartate, L-cysteine, L-glutamate, L-glutamine, L-histidine, L-isoleucine, L-leucine, L-lysine, L-methionine, L-phenylalanine, L-proline, L-serine, L-threonine, L-tryptophan, L-tyrosine, L-valine, and L-cystine.

8. The basal culture medium of claim 1, wherein the one or more vitamins comprise at least 8 of the following vitamins: D-biotin, choline, folic acid, myo-inositol, niacinamide, p-aminobenzoic acid, D-pantothenic acid, vitamin B6, riboflavin, thiamine, and vitamin B12.

9. The basal culture medium of claim 1, wherein the one or more inorganic ions comprise at least 8 of the following ions: $Na^+$, $K^+$, $Ca^{2+}$, $Mg^{2+}$, $NH_4^+$, $Cl^-$, $HCO_3^-$, $PO_4^{3-}$, $SO_4^{2-}$, and $NO_3^-$.

10. The basal culture medium of claim 1, wherein
    the at least 9 proteinogenic amino acids comprise glycine, L-alanine, L-arginine, L-asparagine, L-aspartate, L-cysteine, L-glutamate, L-glutamine, L-histidine, L-isoleucine, L-leucine, L-lysine, L-methionine, L-phenylalanine, L-proline, L-serine, L-threonine, L-tryptophan, L-tyrosine, L-valine, and L-cystine;
    the one or more vitamins comprise D-biotin, choline, folic acid, myo-inositol, niacinamide, p-aminobenzoic acid, D-pantothenic acid, vitamin B6, riboflavin, thiamine, and vitamin B12;
    the one or more inorganic ions are present as inorganic salts, and wherein the inorganic salts comprise $CaCl_2$, $KCl$, $MgCl_2$, $MgSO_4$, $NaCl$, $NaHCO_3$, $Na_2HPO_4$, $Ca(NO_3)_2 \cdot 4H_2O$, and $NH_4Cl$;
    the at least 10 small organic compounds comprise 2-hydroxybutyrate, 3-hydroxybutyrate, 4-hydroxyproline, acetate, acetone, acetylglycine, alpha-aminobutyrate, betaine, carnitine, citrate, citrulline, creatine, creatinine, formate, fructose, galactose, glutathione, glycerol, hypoxanthine, lactate, malonate, ornithine, pyruvate, succinate, taurine, urea, and uric acid; and
    the basal culture medium further comprises phenol red.

11. The basal culture medium of claim 1, further comprising one or more antibiotics, pH indicators, or both.

12. A culture medium comprising the basal culture medium of claim 1; and serum or a serum substitute.

13. The culture medium of claim 12, wherein the culture medium comprises from 1% to 20% serum, from 1% to 5% serum, from 5% to 10% serum, from 10% to 20% serum, or approximately 10% serum.

14. The culture medium of claim 12, wherein the serum is fetal bovine serum.

15. A method of preparing the basal culture medium of claim 1, comprising combining the respective components thereof.

16. A composition comprising the basal culture medium of claim 1; and one or more mammalian cells.

17. The composition of claim 16, wherein the mammalian cells comprise human cells.

18. The composition of claim 16, wherein the cells comprise blood cells.

19. The composition of claim 16, wherein the cells comprise cancer cells.

20. The composition of claim 16, further comprising a test agent.

21. The composition of claim 20, wherein the test agent is a chemotherapeutic agent.

22. A method of culturing one or more mammalian cells comprising providing the culture medium of claim 12; and culturing one or more mammalian cells in the culture medium.

23. The method of claim 22 wherein the one or more mammalian cells comprise human cells.

24. The method of claim 22, wherein the one or more mammalian cells comprise blood cells.

25. The method of claim 22, wherein the one or more mammalian cells comprise cancer cells.

26. The method of claim 22, further comprising adding a test agent to the culture medium.

* * * * *

```
                              SEQUENCE LISTING

<160> NUMBER OF SEQ ID NOS: 18

<210> SEQ ID NO 1
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcaccggttt aattaacgcc accatgggca ctgaatataa acttgtggta gttgg            55

<210> SEQ ID NO 2
<211> LENGTH: 77
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgcggatcct tattacttgt catcgtcatc cttgtaatca atgtcatgat ctttataatc      60
accgtcatgg tctttgt                                                     77

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agtcgcctgc ggccgccata attacacact ttgtctttga cttc                       44

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccaccgcaca gcaagcagca gctgatcttc agacc                                 35

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctgcttgat gccccagact gtgagttgca acag                                  34

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 6
cgagactagc ctcgagcagc agccccttc accgag                              36

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccgcatcacc atggtaatag cgatgactaa tacg                               34

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccgttaatta aagggacgat gcgcgagtac aaagtggtgg tgctg                   45

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cccttgcggc cgcgctgcct ccttgtatgt tacatgcaga acagc                   45

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgtacggtgg gaggtctata taag                                          24

<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cggcgggaat tcttattact tgtcatcgtc atccttgtaa tcaatgtcat g            51

<210> SEQ ID NO 12
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccgttaatta acgcgacaat ggcggtcgct cgtgcagctt tggggccatt ggtgac        56

<210> SEQ ID NO 13
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cccttgcggc cgcgctgcct ccaacaccaa gtctactcaa atacgcttcc caagc         55

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctttcctccc ccatcgccat cgatctgcgg ggc                                 33

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gccccgcaga tcgatggcga tggggagga aag                                  33

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtgctgttgg acgccgagca gggaggcaag                                     30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cttgcctccc tgctcggcgt ccaacagcac                                     30

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 18 ccctttctt ttaaaattgt ggatgaatac tgcc                                    34
```